(12) United States Patent
Payne et al.

(10) Patent No.: US 12,016,902 B2
(45) Date of Patent: Jun. 25, 2024

(54) BIOLOGIC FOR THE TREATMENT OF CANCER

(71) Applicant: LOMA LINDA UNIVERSITY, Loma Linda, CA (US)

(72) Inventors: Kimberly J. Payne, Loma Linda, CA (US); Olivia L. Francis-Boyle, Loma Linda, CA (US)

(73) Assignee: LOMA LINDA UNIVERSITY, Loma Linda, CA (US)

( * ) Notice: Subject to any disclaimer, the term of this patent is extended or adjusted under 35 U.S.C. 154(b) by 216 days.

(21) Appl. No.: 16/500,194

(22) PCT Filed: Apr. 4, 2018

(86) PCT No.: PCT/US2018/026087
§ 371 (c)(1),
(2) Date: Oct. 2, 2019

(87) PCT Pub. No.: WO2018/187471
PCT Pub. Date: Oct. 11, 2018

(65) Prior Publication Data
US 2021/0077581 A1 Mar. 18, 2021

Related U.S. Application Data

(60) Provisional application No. 62/481,559, filed on Apr. 4, 2017.

(51) Int. Cl.
| | | |
|---|---|---|
| *A61K 38/20* | (2006.01) | |
| *A61K 38/19* | (2006.01) | |
| *A61P 35/00* | (2006.01) | |
| *A61P 35/02* | (2006.01) | |
| *G01N 33/574* | (2006.01) | |
| *A61K 38/18* | (2006.01) | |
| *A61K 45/06* | (2006.01) | |

(52) U.S. Cl.
CPC .......... *A61K 38/2046* (2013.01); *A61K 38/19* (2013.01); *A61P 35/00* (2018.01); *A61P 35/02* (2018.01); *G01N 33/57426* (2013.01); *G01N 33/57492* (2013.01); *A61K 38/1808* (2013.01); *A61K 45/06* (2013.01); *G01N 33/57411* (2013.01); *G01N 33/57423* (2013.01); *G01N 33/57449* (2013.01)

(58) Field of Classification Search
None
See application file for complete search history.

(56) References Cited

U.S. PATENT DOCUMENTS

| | | |
|---|---|---|
| 2005/0084477 A1 | 4/2005 | Van Antwerp et al. |
| 2006/0014690 A1 | 1/2006 | Bishop et al. |
| 2012/0282258 A1 | 11/2012 | Weinstock et al. |
| 2014/0302061 A1 | 10/2014 | Beaumont et al. |
| 2014/0308281 A1 | 10/2014 | Brouard et al. |
| 2015/0010475 A1 | 1/2015 | Brinker et al. |
| 2015/0216886 A1 | 8/2015 | MacBeth et al. |
| 2015/0301032 A1 | 10/2015 | De |

FOREIGN PATENT DOCUMENTS

| | | | |
|---|---|---|---|
| WO | WO-2004050113 A1 * | 6/2004 | .............. A61P 17/06 |
| WO | 2005007186 | 1/2005 | |
| WO | 2004050113 | 6/2014 | |
| WO | 2015084513 | 6/2015 | |

OTHER PUBLICATIONS

Skolnick et al (Trends Biotechnol. Jan. 2000;18(1):34-9) (Year: 2000).*
Burgess et al. (J. Cell Biol. 111:2129-2138, 1990) (Year: 1990).*
Miosge (Proc Natl Acad Sci U S A. Sep. 15, 2015;112(37):E5189-98) (Year: 2015).*
Bork (Genome Research, 2000, 10:398-400) (Year: 2000).*
Guido et al (Curr Med Chem. 2008; 15(1):37-46) (Year: 2008).*
Clark et al (J. Med. Chem., 2014, 57 (12), pp. 5023-5038) (Year: 2014).*
Kulmanov et al (Bioinformatics, 34(4), 2018, 660-668) (Year: 2018).*
Demehri et al {: J Clin Invest. 2016;126(4):1458-1470) (Year: 2016).*
Yao et al (JCI Insight. 2022;7(21):e161438) (Year: 2022).*
Tsilingiri et al (Cell Mol Gastroenterol Hepatol 2017;3:174-182) (Year: 2017).*
Shochat et al (J Exp Med. May 9, 2011;208(5):901-8.) (Year: 2011).*
International Search Report and Written Opinion for PCT/US2018/026087, dated Aug. 28, 2018.
Francis, Olivia L., TSLP-induced Mechanisms and Potential Therapies for CRLF2 B-cell Acute Lymphoblastic Leukemia, Thesis, Loma Linda University, Jun. 2015.
Hambeck et al., Prestimulation of Head and Neck Cancer Cells with Growth Factors Enhances Treatment Efficacy, Anticancer Research 26: 1091-1096 (2006).

(Continued)

*Primary Examiner* — Brian Gangle
*Assistant Examiner* — Andrea K McCollum
(74) *Attorney, Agent, or Firm* — Womble Bond Dickinson (US) LLP

(57) ABSTRACT

In one aspect, methods of treating a subject having a cancer that expresses a cytokine receptor are provided. In some embodiments, the method comprises administering to the subject a biologic agent in an amount sufficient to induce loss of cytokine receptor signaling through increased expression of a Suppressor of Cytokine Signaling genes and/or loss of one or more cytokine receptor components from the cancer cell surface. In some embodiments, the biologic agent is a cytokine or cytokine mimetic.

4 Claims, 23 Drawing Sheets
Specification includes a Sequence Listing.

(56) References Cited

OTHER PUBLICATIONS

Jain et al., Ph-like acute lymphoblastic leukemia: a high-risk subtype in adults, Blood, Feb. 2, 2017, vol. 129, pp. 572-581.
Suzuki et al., Clinical Impact of Immune Microenvironment in Stage I Lung Adenocarcinoma: Tumor Interleukin-12 Receptor b2 (IL-12Rb2), IL-7R, and Stromal FoxP3/CD3 Ratio Are Independent Predictors of Recurrence, Journal of Clinical Oncology, Feb. 1, 2013, vol. 31, pp. 490-498.
EPO Extended Search Report for European Patent Application No. 18781174.0, dated Feb. 24, 2021.
Noa Tal et al., "Interleukin 7 and thymic stromal lymphopoietin: from immunity to leukemia," Cellular and Molecular Life Sciences, vol. 7, No. 3, Apr. 27, 2013.

* cited by examiner

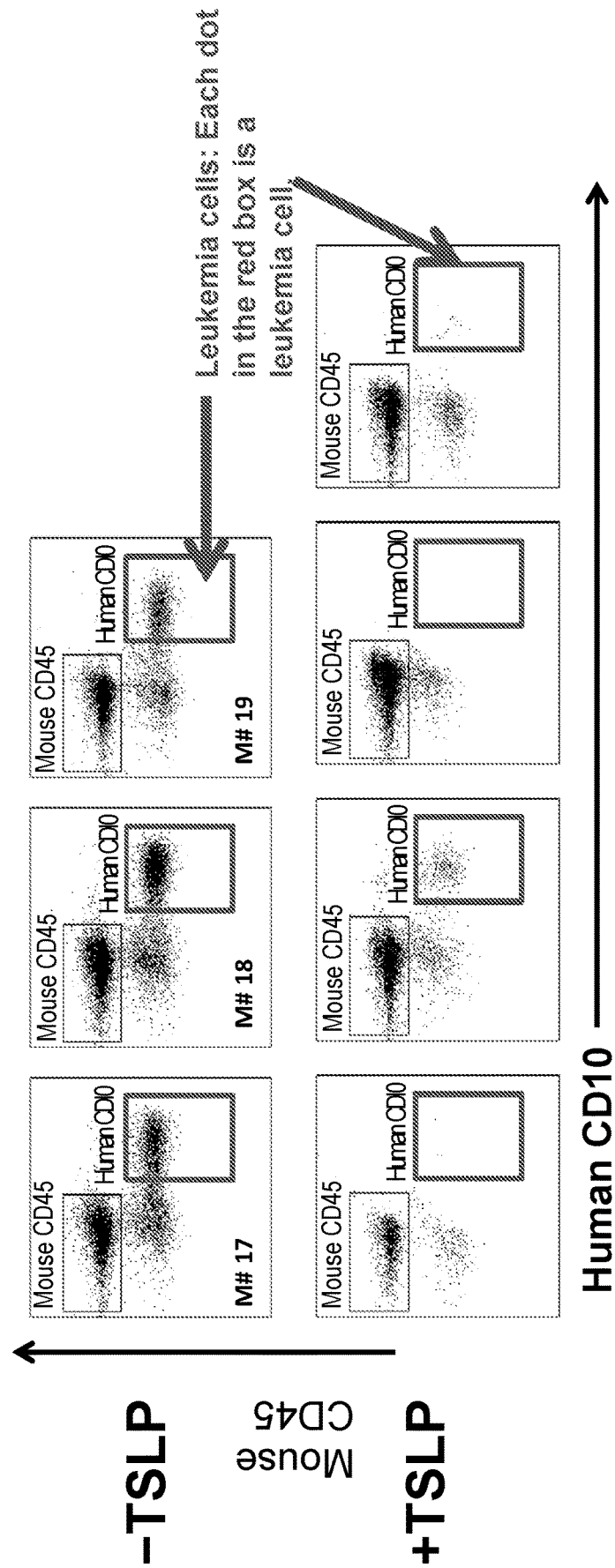

FIG. 8

| SOCS Gene | Fold Change | P Value | Adj. P Value | +TSLP (high dose) | | | −TSLP | | |
|---|---|---|---|---|---|---|---|---|---|
| | | | | Rep 1 | Rep 2 | Rep 3 | Rep 1 | Rep 2 | Rep 3 |
| CISH | 0.165 | 1.37E-03 | 1.27E-02 | 2.851 | 2.384 | 2.827 | 1.348 | 0.031 | -0.370 |
| SOCS1 | 4.271 | 2.26E-04 | 4.15E-03 | 1.854 | 1.662 | 1.391 | -0.433 | -0.247 | -0.559 |
| SOCS2 | 6.253 | 2.26E-06 | 5.67E-04 | 0.415 | 0.294 | 0.304 | 2.397 | 2.209 | -2.340 |
| SOCS3 | 52.593 | 5.42E-06 | 7.65E-04 | 3.932 | 3.726 | 3.370 | | | |
| SOCS4 | -1.092 | 2.94E-01 | 5.87E-01 | 0.000 | 0.123 | 0.000 | 0.127 | 0.042 | 0.139 |
| SOCS5 | 1.069 | 1.27E-01 | 3.55E-01 | 0.358 | 0.215 | 0.222 | 0.224 | 0.126 | 0.092 |
| SOCS6 | 1.008 | 6.76E-01 | 8.21E-01 | -0.026 | -0.011 | -0.044 | -0.027 | -0.009 | -0.006 |
| SOCS7 | -1.033 | 6.57E-01 | 8.09E-01 | 0.015 | -0.327 | -0.460 | -0.197 | -0.550 | -0.281 |

FIG. 13A-C

FIG. 15
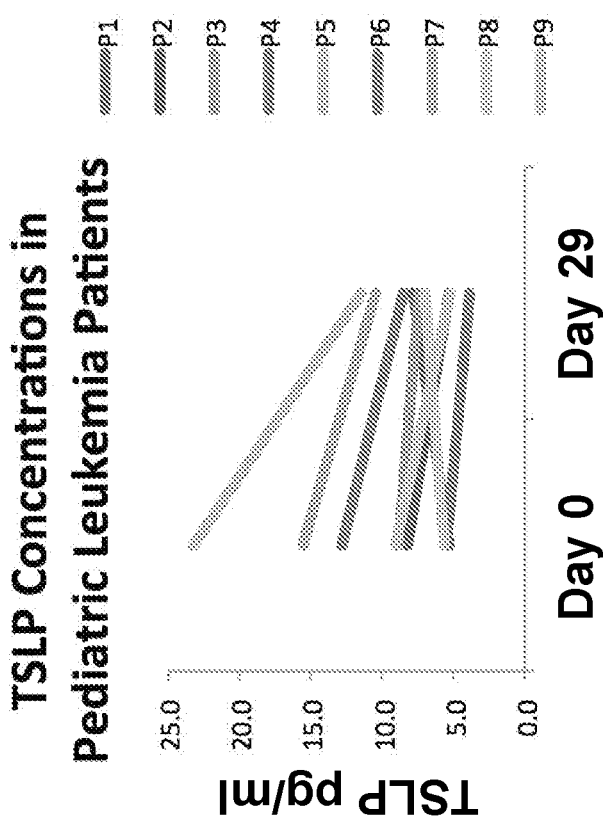
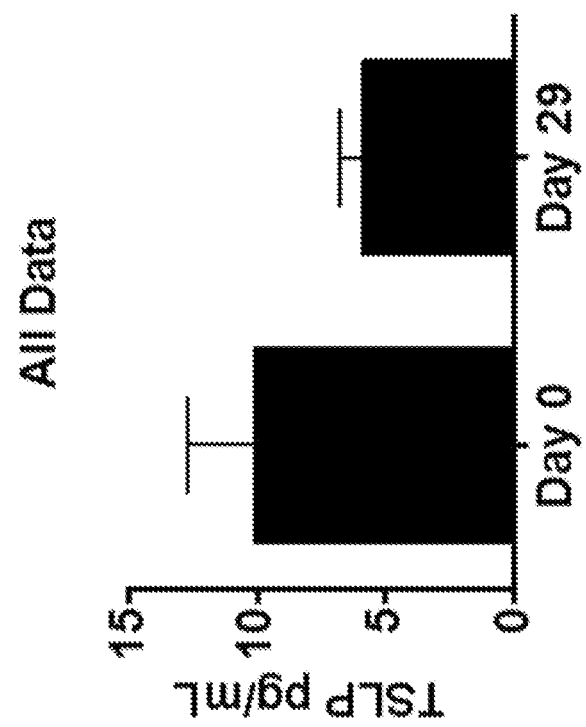

BIOLOGIC FOR THE TREATMENT OF CANCER

CROSS-REFERENCE TO RELATED APPLICATIONS

This application is a U.S. National Phase Under 35 U.S.C. § 371 of International Application No. PCT Application No. PCT/US18/26087, filed Apr. 4, 2018, titled "BIOLOGIC FOR THE TREATMENT OF CANCER", which claims priority to U.S. Provisional Application No. 62/481,559, filed Apr. 4, 2017, titled "BIOLOGIC FOR THE TREATMENT OF LEUKEMIA", the entire contents of which are incorporated by reference herein.

STATEMENT AS TO RIGHTS TO INVENTIONS MADE UNDER FEDERALLY SPONSORED RESEARCH AND DEVELOPMENT

This invention was made with government support under grant no. R21 CA162259, and grant no. 1R01CA209829 awarded by the National Institutes of Health. The government has certain rights in the invention.

SEQUENCE LISTING

The instant application contains a Sequence Listing which has been filed electronically in ASCII format and is hereby incorporated by reference in its entirety. Said ASCII copy, created on Oct. 11, 2019, is named 105781_0099_9_SL.txt and is 39,209 bytes in size.

BACKGROUND OF THE INVENTION

Acute lymphoblastic leukemia (ALL) is the most common cancer in children and adolescents, killing more pediatric patients every year than any other type of malignancy (DeSantis et al., *CA: A Cancer Journal for Clinicians*, 2014, 64:252-271). When children with ALL relapse, the survival rate is less than 50%, and this rate has not improved for more than 30 years (Nguyen et al., *Leukemia*, 2008, 22:2142-2150). Although ALL is less common in adults, it is more deadly, reaching 5-year survival rates of less than 12% in people over 65 who have poorer tolerance for toxic therapies (DeSantis et al).

The majority of ALL cases in children and adults are the B-cell type (B-ALL) (Pui et al., *N Engl J Med*, 2004, 350:1535-1548). In children, B-ALL with the poorest outcome is caused by genetic alterations of the cytokine receptor-like factor 2 (CRLF2) gene (CRLF2 B-ALL) (Harvey et al., *Blood*, 2010, 116:4874-4884). CRLF2 B-ALL is defined by a genetic alteration that causes overexpression of the cytokine receptor component, CRLF2. Activation of the CRLF2 receptor by the cytokine, TSLP, initiates downstream signaling pathways that are known to promote survival and proliferation of leukemia cells (Malin et al., *Curr Opin Immunol*, 2010:22-168-176; Brown et al., *Cancer Res*, 2007, 67:9963-9970). CRLF2 B-ALL is particularly devastating in Hispanic children, occurring five times more often than in other children. In adults, CRLF2 B-ALL makes up a third of all B-ALL cases and has similarly poor outcomes (Chiaretti et al., *Leukemia Research*, 2016, 41:36-42).

Accordingly, there remains a need for compositions and methods of treating cancer such as leukemias and solid tumors.

BRIEF SUMMARY OF THE INVENTION

In one aspect, methods for treating a subject having a cancer that expresses a cytokine receptor are provided. In some embodiments, the method comprises:
administering to the subject a biologic agent in an amount sufficient to induce the a loss of cytokine receptor signaling in a cancer cell in the subject. In some embodiments, the loss of cytokine receptor signaling can arise from expression of one or more Suppressor of Cytokine Signaling genes and/or loss of one or more of the cytokine receptor components from the cell surface.

In one aspect, methods for treating a subject having a cancer that expresses a cytokine receptor are provided. In some embodiments, the method comprises:
administering to the subject a biologic agent in an amount sufficient to increase expression of one or more Suppressor of Cytokine Signaling genes in a cancer cell in the subject.

In some embodiments, the cancer is a leukemia. In some embodiments, the leukemia is acute lymphoblastic leukemia (ALL). In some embodiments, the leukemia is B-cell type ALL. In some embodiments, the B-cell type ALL is Ph-like B-cell type ALL. In some embodiments, the leukemia is acute myeloid leukemia (AML) or acute lymphoblastic leukemia (ALL), T-cell type ALL. In some embodiments, the cancer is a solid tumor. In some embodiments, the solid tumor is cervical, lung or ovarian cancer. In some embodiments, the cytokine receptor is cytokine receptor-like factor 2 (CRLF2), interleukin-7 receptor-α (IL-7R-α) or epidermal growth factor receptor (EGFR) or their co-receptors in transmitting cytokine signals. In some embodiments, the cancer overexpresses CRLF2. In some embodiments, the biologic agent is a cytokine or a cytokine mimetic. In some embodiments, the biologic agent is human thymic stromal lymphopoietin (TSLP), epidermal growth factor (EGF), interleukin 7 (IL-7), or a mimetic thereof. In some embodiments, the cytokine or cytokine mimetic is recombinantly produced. In some embodiments, the subject is an adult or juvenile. In some embodiments, the biologic agent is administered intravenously or systemically. In some embodiments, the biologic agent is administered in combination with a second agent. In some embodiments, the second agent is a chemotherapeutic agent or a demethylation agent.

In some embodiments, methods for treating a subject having a cancer characterized by overexpression of cytokine receptor-like factor 2 (CRLF2) are provided. In some embodiments, the method comprises:
administering to the subject a biologic agent, in an amount sufficient to inhibit CRLF2 signaling and increase expression of one or more SOCS genes or reduce cell surface expression of CRLF2 and/or its co-receptor, IL-7R-α, in a cancer cell in the subject, thereby treating the cancer.

In some embodiments, methods for treating a subject having a cancer characterized by overexpression of cytokine receptor-like factor 2 (CRLF2) are provided. In some embodiments, the method comprises:
administering to the subject a biologic agent, in an amount sufficient to increase expression of one or more SOCS genes and inhibit CRLF2 signaling in a cancer cell in the subject, thereby treating the cancer.

In some embodiments, the cancer is a leukemia. In some embodiments, the leukemia is acute lymphoblastic leukemia (ALL). In some embodiments, the leukemia is acute myeloblastic leukemia (AML). In some embodiments, the leukemia is B-cell type ALL. In some embodiments, the B-cell type ALL is Ph-like B-cell type ALL. In some embodiments, the leukemia is acute lymphoblastic leukemia T cell type (T cell ALL). In some embodiments, the cancer is a solid tumor. In some embodiments, the biologic agent is human thymic stromal lymphopoietin (TSLP), EGF, interleukin 7 (IL-7), or a mimetic thereof. In some embodiments, the cytokine or cytokine mimetic is recombinantly produced. In some embodiments, the subject is an adult or juvenile. In some embodiments, the biologic agent is administered intravenously or systemically. In some embodiments, the biologic agent is administered in combination with a second agent or agents. In some embodiments, the second agent is a chemotherapeutic agent or a demethylation agent. In some embodiments, the biologic agent is administered at a dose that results in a serum level in the subject of at least 30 pg/mL. In some embodiments, the biologic agent is administered at a dose that results in a serum level in the subject that is at least as high as a control physiological level for the biological agent. In some embodiments, the biologic agent is administered at a dose that results in increased internalization of IL-7R-α and/or decreased IL-7R-α or CRLF2 downstream signaling (e.g., decreased STAT5 phosphorylation and/or decreased ribosomal protein S6 phosphorylation).

In one aspect, a pharmaceutical composition for the treatment of a cancer that expresses a cytokine receptor are provided. In some embodiments, the pharmaceutical composition for the treatment of a cancer that expresses a cytokine receptor comprises:
a biologic agent in an amount sufficient to induce the a loss of cytokine receptor signaling by increasing expression of one or more SOCS genes and/or loss of surface cytokine receptor in a cancer cell; and a pharmaceutically acceptable carrier.

In one aspect, a pharmaceutical composition for the treatment of a cancer that expresses a cytokine receptor are provided. In some embodiments, the pharmaceutical composition for the treatment of a cancer that expresses a cytokine receptor comprises:
a biologic agent in an amount sufficient to increase expression of one or more SOCS genes in a cancer cell; and a pharmaceutically acceptable carrier.

In some embodiments, the cancer is characterized by an overexpression of CRLF2 or EGFR. In some embodiments, the cancer is a solid tumor. In some embodiments, the solid tumor is cervical, lung or ovarian cancer or other solid tumor in which EGF is an oncogenic driver. In some embodiments, the cancer is a leukemia. In some embodiments, the leukemia is acute lymphoblastic leukemia (ALL), B-cell type ALL, Ph-like B-cell type ALL, acute myeloid leukemia, or T cell acute lymphoblastic leukemia (T cell ALL). In some embodiments, the cytokine receptor is CRLF2, EFGR or IL-7R-alpha. In some embodiments, the biologic agent is a cytokine or cytokine mimetic. In some embodiments, the biologic agent is human TSLP, EGF, IL-7 or a mimetic thereof. In some embodiments, the biologic agent is TSLP. In some embodiments, the biologic agent is EGF. In some embodiments, the biologic agent is IL-7. In some embodiments, the pharmaceutical composition comprises a chemotherapeutic agent or demethylation agent as the second agent.

In another aspect, a kit for the treatment of a cancer that expresses a cytokine receptor are provided. In some embodiments, the kit for the treatment of a cancer that expresses a cytokine receptor comprises:
a biologic agent in an amount sufficient to induce a loss of cytokine signaling in a cancer cell in the subject. This loss of receptor signaling can arise from expression of one or more Suppressor of Cytokine Signaling genes and/or loss of one or more of the cytokine receptor components from the cell surface; and
an additional agent or agents.

In another aspect, a kit for the treatment of a cancer that expresses a cytokine receptor are provided. In some embodiments, the kit for the treatment of a cancer that expresses a cytokine receptor comprises:
a biologic agent in an amount sufficient to increase expression of one or more SOCS genes in a cancer cell; and
an additional agent or agents.

In some embodiments, the kit comprises a biologic agent that is a cytokine or cytokine mimetic. In some embodiments, the kit comprises a biologic agent that is human TSLP, EGF, IL-7 or a mimetic thereof. In some embodiments, the kit comprises a chemotherapeutic agent as the second agent. In some embodiments, the kit comprises a demethylation agent as the second agent. In some embodiments, the kit for the treatment of cancer is for the treatment of leukemia or solid tumors. In some embodiments, the solid tumor is a cervical cancer. In some embodiments, the solid tumor is a lung cancer. In some embodiments, the solid tumor is an ovarian cancer. In some embodiments, the cancer overexpresses or expresses a mutated form of EGFR, CRLF2 or IL-7Rα. In some embodiments, the one or more SOCS genes is SOCS1, SOC2, SOCS3 and/or CISH.

In another aspect, a method of inhibiting CRLF2 signaling in a cancer cell is provided. In some embodiments, the method for inhibiting CRLF2 signaling in a cancer cell comprises administering to the cancer cell an effective amount of TSLP. In some embodiments, the cancer cell is from a leukemia. In some embodiments, the TSLP is human TSLP or a mimetic of human TSLP.

In another aspect, a method of inhibiting IL-7Rα signaling in a cancer cell is provided. In some embodiments, the method for inhibiting IL-7Rα signaling in a cancer cell comprises administering to the cancer cell an effective amount of IL-7. In some embodiments, the cancer cell is from a leukemia. In some embodiments, the IL-7 is human IL-7 or a mimetic of human IL-7.

In another aspect, a method of inhibiting EGFR signaling in a cancer cell is provided. In some embodiments, the method for inhibiting EGFR signaling in a cancer cell comprises administering to the cancer cell an effective amount of EGF. In some embodiments, the cancer cell is from a solid tumor. In some embodiments, the solid tumor is cervical, lung or ovarian cancer. In some embodiments, the EGF is human EGF or a mimetic of human EGF.

In another aspect, a method of predicting response of a cancer patient to TSLP treatment is provided. In some embodiments, a method of predicting response of a cancer patient to TSLP treatment comprises:
detecting a level of IL-7Rα expression on the surface of a cancer cell from the cancer patient;
detecting a level of CRLF2 expression on the surface of the cancer cell from the cancer patient; and
calculating a ratio of CRLF2 to IL-7Rα based on the detected levels of expression; wherein the cancer patient is predicted to respond to the TSLP treatment if the level of CRLF2 is higher than the level of IL-7Rα. In some embodiments, the ratio of CRLF2 to IL-7Rα is 2:1. In some embodiments, the ratio of CRLF2 to IL-7Rα is at least 2:1. In some embodiments, the ratio of CRLF2 to IL-7Rα is 2:1, 3:1, 5:1, 10:1, 20:1, 50:1, or 100:1. In some embodiments, the ratio of CRLF2 to IL-7Rα is 2:1, 3:1, 5:1, 10:1, 20:1, 50:1, 100:1, or more.

In some embodiments, the cancer cell is from leukemia. In some embodiments, the leukemia is acute lymphoblastic leukemia (ALL). In some embodiments, the leukemia is B-cell type ALL. In some embodiments, the B-cell type ALL is Ph-like B-cell type ALL. In some embodiments, the leukemia is acute myeloblastic leukemia (AML). In some embodiments, the leukemia is acute lymphoblastic leukemia T cell type (T cell ALL). In some embodiments, the cancer cell is from a solid tumor. In some embodiments, the method further comprises detecting a level of phosphorylation for STAT5 and/or level of phosphorylation for ribosomal S6 in the cancer cell from the cancer patient. In some embodiments, the detecting comprises flow cytometry.

In another aspect, a method of diagnosing a cancer subtype is provided. In some embodiments, the method of diagnosing cancer comprises:

contacting a cell sample with a labeled antibody that binds to CRLF2 that is expressed on a surface of a cell from the cell sample; and detecting CRLF2 in the cell sample, thereby diagnosing the subtype of cancer.

In some embodiments, the cancer subtype is a CRLF2-overexpressing subtype. In some embodiments, the method comprises detecting a level of a CRLF2 in the cell sample that is increased by at least 10%, 20%, 30%, 40%, 50%, 60%, 70%, 80%, 90%, or more relative to a control value; thereby diagnosing the CRLF2-overexpressing subtype. In some embodiments, the method comprises detecting a level of a CRLF2 in the cell sample that is increased by at least 1.5-fold, 2-fold, 3-fold, 4-fold, 5-fold, 6-fold, 7-fold, 8-fold, 9-fold, 10-fold or more relative to a control value; thereby diagnosing the CRLF2-overexpressing subtype.

In some embodiments, the method comprises contacting a cell sample with a labeled antibody that binds to CRLF2 that is expressed on a surface of a cell from the cell sample, and contacting the cell sample with one or more additional markers that are indicative of a cancer cell being evaluated. For example, markers useful for detecting B-cell type ALL cells in a cell sample include, but are not limited to, CD10, CD2 and CD34. Additionally, markers useful for detecting T cells in a cell sample include, but are not limited to, CD5 and CD7.

In some embodiments, the cell sample is from leukemia. In some embodiments, the leukemia is B-cell type ALL. In some embodiments, the B-cell type ALL is Ph-like-B-cell type ALL. In some embodiments, the leukemia is acute myeloid leukemia. In some embodiments, the leukemia is T cell type ALL. In some embodiments, the cell from the cell sample is from a solid tumor. In some embodiments, the method further comprises contacting the cell sample with a labeled antibody that binds to IL-7Rα that is expressed on the surface of the cell from the cell sample and detecting IL-7Rα expression in the cell sample.

BRIEF DESCRIPTION OF THE DRAWINGS

FIG. 5A-5B. High physiological levels of TSLP have an anti-leukemia effect. (A, B). PDX was established from two pediatric patients (Patient #1 and Patient #2), essentially as set forth in Example 1. Two weeks later, PDX mice were injected with control stroma or stroma that express hTSLP to produce +T mice with hTSLP serum levels of ~32-93 pg/ml and control −T PDX mice. After 10 weeks, bone marrow (BM) was harvested and stained for flow cytometry to detect human CRLF2 B-ALL cells (gated in red box). Human B-ALL cells were easily detectable by flow cytometry in bone marrow (BM) harvested from −T PDX mice (top rows). Leukemia cells were essentially absent from +T PDX (bottom rows).

FIG. 8. High-dose TSLP increases expression of multiple SOCS family genes in CRLF2 B-ALL cells from a Hispanic pediatric patient. CRLF2 B-ALL cells from a Hispanic pediatric patient were expanded in a PDX mouse and then harvested and cultured with or without recombinant human TSLP, (TSLP) (15 ng/ml) for 48 hours. Cells were then assayed by whole genome microarray to determine RNA expression. Plotted are the relative expression levels of all of the SOCs family mRNA in 3 technical replicates. All TSLP was $E.\ coli$-produced recombinant human TSLP.

FIG. 15. Serum Levels of TSLP in pediatric leukemia patients are low physiological levels which allows leukemia to develop. (A) Quantitation of median levels of hTSLP from nine pediatric leukemia patients collected at day 0 and day 29. (B) Quantitation of individual levels of hTSLP from nine pediatric leukemia patients (P1-P9) collected at day 0 and day 29. These data show that normal physiological doses of TSLP in patients are consistent with the subtherapeutic doses as predicted in FIG. 4.

DETAILED DESCRIPTION OF THE INVENTION

I. Introduction

The present disclosure relates to the surprising finding that, in cancer cells, increasing the levels of any of human thymic stromal lymphopoietin (TSLP), EGF or IL-7 induces mechanisms that result in the loss of signaling. A patient-derived xenograft model (produced by injecting leukemia cells from human patients into immune-deficient mice) was developed in which human TSLP (hTSLP) was expressed at physiological levels (Francis et al., *Haematologica*, 2016, 101:417-426). These models could also vary the amount of TSLP by injecting more or less of the stroma that produce TSLP. As described herein, it was surprisingly found that high physiological levels of hTSLP had a dramatic anti-leukemia effect, essentially curing early stage disease in PDX generated from two different Hispanic pediatric patients with CRLF2 B-ALL. Further, hTSLP expanded the production of normal human B cells at both low and high physiological levels with no reduction in other immune cells. Taken together, these data suggest the use of the hTSLP cytokine as a biologic therapy to target CRLF2 B-ALL cells while supporting the restoration of normal human B cells following chemotherapy. As described herein, production of high physiological levels of hTSLP (>30 pg/ml) in a xenograft mouse model caused an upregulation in SOCS gene expression and loss of IL-7Rα that resulted in shutting down the CRLF2 signaling pathway leading to a reduction in leukemia cells and expansion of normal B cell progenitors, which help restore the immune system. While TSLP has been proposed as a therapy in colon cancer to increase TSLP induced signaling (Yue et al., (2016) *Oncotarget*, 13:16840-54) and requires an active TSLP signaling pathway, the use of TSLP as proposed herein is to shut down or inhibit the CRLF2 signaling pathway.

Figure 7:
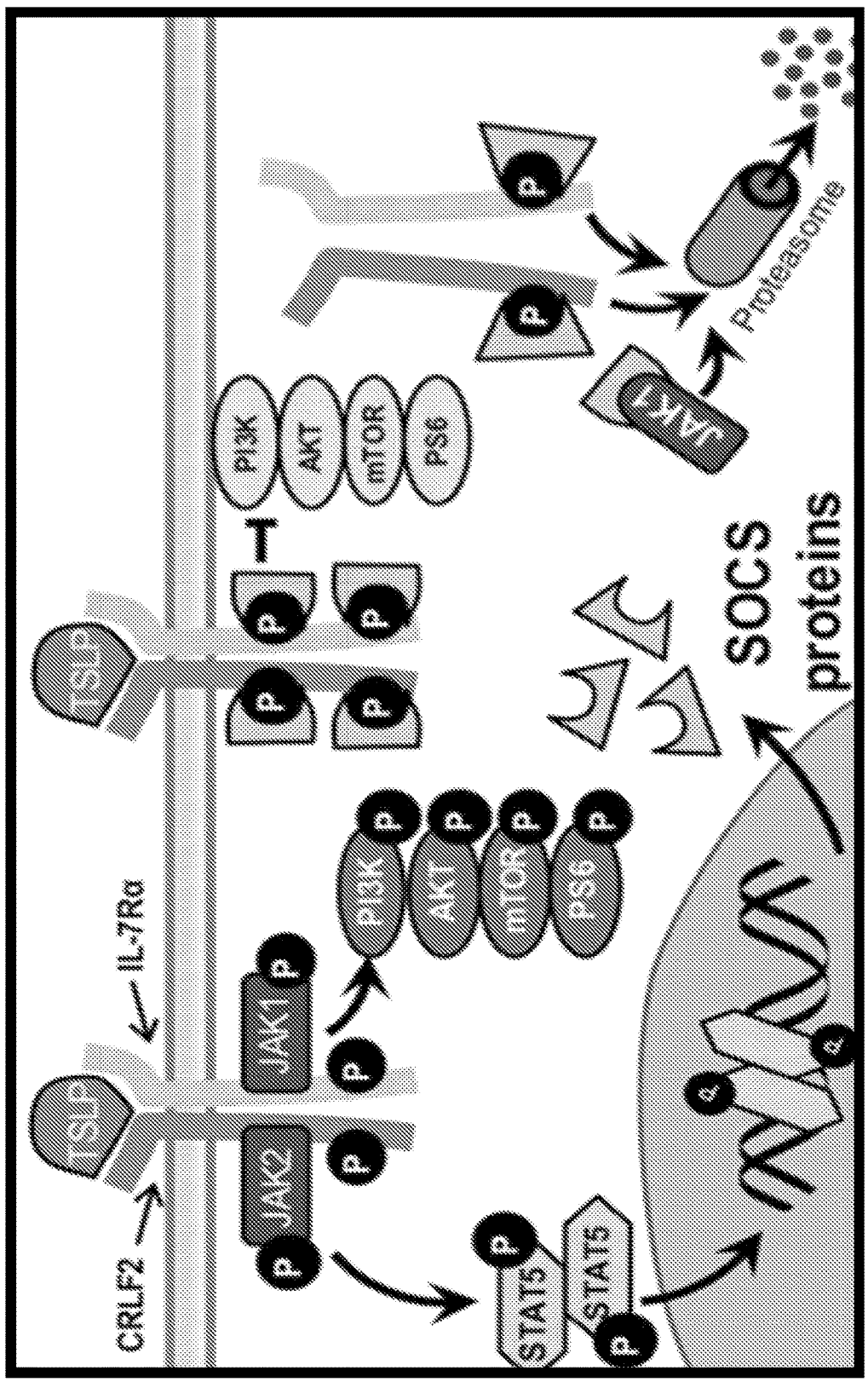
FIG. 7. SOCS proteins regulate JAK-STAT signaling via negative feedback. Schematic representing SOCS proteins regulating the JAK-STAT signaling pathway via negative feedback. Expression of SOCS genes is upregulated by JAK-STAT signals. SOCS proteins inhibit JAK-STAT signaling by directly interacting with JAKS or the JAK cytokine receptors to prevent JAK phosphorylation. SOCS proteins also target the JAK proteins for proteasomal degradation via ubiquitin ligase. In some cases, SOCS proteins also target the cytokine receptor for degradation.

Without being bound to a particular theory, it is believed that in cancer cells such as leukemia cells that overexpress CRLF2, low physiological levels of TSLP are present, which allows cancer cells to grow normally. However, increasing TSLP levels in the cancer cells upregulates the expression of Suppressor of Cytokine Signaling (SOCS) genes leading to a loss of cytokine receptor signaling through various mechanisms as shown in FIG. 7, including degradation of surface receptors following internalization as shown in leukemia cells treated with high-dose TSLP as in FIG. 12. It is believed that cancer cells overexpressing CRLF2 bind human TSLP to become primed receptor complexes. Once primed, these receptor complexes are capable of immediately binding new IL-7Rα molecules that are produced by the cell, thereby decreasing the presence of IL-7Rα on the surface of the cell but doing so one molecule at a time, thus precluding cancer cells, with high levels of primed CRLF2 from reaching a critical signaling threshold. Thus, increasing TSLP levels results in increased levels of primed CRLF2 and ultimately in the loss of CRLF2 signals that are needed for cancer cell survival and leads to a reduction of cancer cells, while also leading to the expansion of normal B cell progenitors which help to restore the immune system. These data are consistent with a scenario whereby normal B cell precursors respond to TSLP at early stages of development, but then differentiate to more mature B-lineage cells that respond to different signals. In contrast, CRLF2 B-ALL cells are locked in development at the B cell precursor stage where they remain dependent on CRLF2-mediated signals. Accordingly, in one aspect, the present disclosure provides for methods of killing cancer cells and treating cancers (e.g., leukemias or solid tumors that overexpress CRLF2) by administering a cytokine such as TSLP, or a cytokine mimic, in an amount sufficient to shutdown cytokine signaling.

Furthermore, without being bound to a particular theory, it is believed that in cancer cells such as solid tumors or leukemia cells that overexpress EGFR, when low physiological levels of EGF are present, cancer cells grow normally. However, increasing EGF levels shuts down cytokine signals potentially by upregulating SOCS proteins to block signaling and causing degradation of signaling components, including EGFR signaling components. Thus, increasing EGF levels results in the loss of EGFR signals that are needed for cancer cell survival and leads to a reduction of cancer cells. Accordingly, in one aspect, the present disclosure provides for methods of killing cancer cells and treating cancers (e.g., leukemias or solid tumors that express or overexpress EGFR) by administering a cytokine such as EGF or a cytokine mimic, in an amount sufficient to increase expression of SOCS genes or internalization of the EGF receptor.

Additionally, without being bound to a particular theory, it is believed that in cancer cells such as leukemia or lymphoma cells that require a signal from IL-7Rα present on the surface of the cell, increasing IL-7 levels will upregulate the expression of Suppressor of Cytokine Signaling (SOCS) genes. SOCS proteins shut down cytokine signals by blocking signaling and degrading signaling components, including IL-7Rα signaling components. Thus, increasing IL-7 levels results in the loss of IL-7Rα signals that are needed for cancer cell survival and leads to a reduction of cancer cells. Accordingly, in one aspect, the present disclosure provides for methods of killing cancer cells and treating cancers (e.g., leukemia or solid tumors that overexpress CRLF2) by administering a cytokine such as IL-7 or a cytokine mimic, in an amount sufficient to increase expression of SOCS genes and/or internalize the IL-7Rα.

II. Definitions

The terminology used herein is for the purpose of describing particular embodiments only, and is not intended to be limiting, because the scope of the present invention will be limited only by the appended claims. Unless defined otherwise, all technical and scientific terms used herein have the same meaning as commonly understood by one of ordinary skill in the art to which this invention belongs. In this specification and in the claims that follow, reference will be made to a number of terms that shall be defined to have the following meanings unless a contrary intention is apparent. In some cases, terms with commonly understood meanings are defined herein for clarity and/or for ready reference, and the inclusion of such definitions herein should not be construed as representing a substantial difference over the definition of the term as generally understood in the art.

All numerical designations, e.g., pH, temperature, time, concentration, and molecular weight, including ranges, are approximations which are varied (+) or (−) by increments of 0.1 or 1.0, as appropriate. It is to be understood, although not always explicitly stated that all numerical designations are preceded by the term "about."

The singular forms "a," "an," and "the" include plural referents unless the context clearly dictates otherwise. Thus, for example, reference to "a compound" includes a plurality of compounds.

The term "comprising" is intended to mean that the compounds, compositions and methods include the recited elements, but not excluding others. "Consisting essentially of" when used to define compounds, compositions and methods, shall mean excluding other elements that would materially affect the basic and novel characteristics of the claimed invention. "Consisting of" shall mean excluding any element, step, or ingredient not specified in the claim. Embodiments defined by each of these transition terms are within the scope of this invention.

As used herein, the term "biologic agent" refers to an agent or compound, such as a peptide, protein, aptamer, oligopeptide, peptidomimetic, oligonucleotide, or oligonucleotide. In some embodiments, a biologic agent is used to treat a cell or subject having a cancer. In some embodiments, the biologic agent is a cytokine or cytokine mimetic as defined herein. In some embodiments, a biologic agent is a cytokine such as, but not limited to, TSLP (e.g., human TSLP), IL-7 (e.g., human IL-7), and epidermal growth factor (EGF) (e.g., human EGF). In another embodiment, a biologic agent is a cytokine mimetic of human TSLP, EGF or IL-7. In one embodiment, the biologic agent is human TSLP. In another embodiment, the biological agent is human IL-7. In another embodiment, the biological agent is human EGF.

As used herein, the term "cytokine" refers to a class of endogenous immunoregulatory proteins (such as interleukins or interferons) produced by cells of the immune system (e.g., macrophages, B and T lymphocytes) that are important in cell signaling. Cytokines can mediate and regulate immune responses, inflammation and hematopoiesis through receptors. Subsequent cascades of intracellular signaling can then alter cell functions, which can include the upregulation or downregulation of genes and their transcription factors, which may result in the production of other cytokines, an increase in the number of surface receptors for other molecules, degradation of receptor components, or the suppression of their own effect by feedback inhibition. The effect of a particular cytokine on a given cell generally depends on the cytokine, its extracellular abundance, the presence or absence of the complementary receptor on the cell surface and downstream signals activated by receptor binding.

Hematopoietic growth factors are a special class of naturally occurring cytokines involved in the proliferation, differentiation, and survival of hematopoietic progenitor cells. Some of these cytokine growth factors have been developed into therapeutics using recombinant DNA technology including: bone morphogenic protein (BMP) to treat bone related conditions; erythropoietin (EPO) to treat anemia; IL-2 to treat some forms of cancer; granulocyte colony-stimulating factor (G-CSF) to treat acute myeloid leukemia; granulocyte macrophage colony-stimulating factor (GM-CSF) to treat fungal infection in cancer patients; and IL-11 to increase platelet production (reviewed in Tekewe, *Pharmacophore*, 2012, Vol. 3 (2), 81-108). Accordingly, the term cytokine as used herein includes naturally occurring "hematopoietic growth factors" such as, but not limited to, EGF, BMP, EPO, G-CSF, GM-CSF, TSLP, IL-2, IL-3, IL-7 and IL-11.

As used herein, the term "cytokine mimetic" refers to a compound or molecule, or class of compounds or molecules, that possess functional and/or structural characteristics typically attributed to a naturally occurring cytokine. In one aspect, the cytokine mimetic is a recombinant cytokine. In one embodiment, the cytokine mimetic is a modified, truncated or altered form of a naturally occurring cytokine. In another embodiment, a cytokine mimetic is a modified, truncated or altered form of a naturally occurring cytokine that retains at least 60%, 65%, 70%, 80%, 85%, 90%, 95%, 96%, 97%, 98%, or 99% of the corresponding naturally occurring cytokine function being measured (e.g., upregulation or downregulation of one or more genes). In some embodiments, a cytokine mimetic is a compound or molecule that is produced by means other than direct extraction from a native biological source (such as a T or B cell) that retains at least 60%, 65%, 70%, 80%, 90%, 95%, 96%, 97%, 98%, or 99% of the corresponding naturally occurring cytokine activity being measured (e.g., modulation of SOCS gene expression). In one embodiment, a cytokine mimetic can include a protein whose sequence is at least 50% equivalent to that of the naturally occurring cytokine, or at least 60% equivalent to that of the naturally occurring cytokine, or at least 70% equivalent to that of the naturally occurring cytokine, or at least 80% equivalent to that of the naturally occurring cytokine, or at least 90% equivalent to that of the naturally occurring cytokine, or at least 95% equivalent to that of the naturally occurring cytokine, or at least 97% equivalent to that of the naturally occurring cytokine, or at least 98% equivalent to that of the naturally occurring cytokine, or at least 99% equivalent to that of the naturally occurring cytokine. In one embodiment, the naturally occurring cytokine is TSLP. In another embodiment, the naturally occurring cytokine is human TSLP. In another embodiment, the naturally occurring cytokine is IL-7. In yet another embodiment, the naturally occurring cytokine is EGF. Accordingly, it is contemplated that a cytokine mimetic can include a recombinant form of IL-7, EGF or TSLP.

It is therefore contemplated that a recombinant compound or molecule (such as a protein, polynucleotide or nucleic acid encoding a polynucleotide) that maintains at least 80%, 85%, 90%, 91%, 92%, 93%, 94%, 95%, 96%, 97%, 98%, or 99% homology to a naturally occurring cytokine (such as, but not limited to, TLSP, EGF or IL-7) can function as a cytokine mimetic. In some embodiments, a cytokine mimetic can include a synthetically manufactured peptide that retains at least 50%, 60%, 70%, 80%, 85%, 90%, 91%, 92%, 93%, 94%, 95%, 96%, 97%, 98%, or 99% homology to a naturally occurring cytokine. In another embodiment, a cytokine mimetic can include a synthetically manufactured peptide that retains at least 50%, 60%, 70%, 80%, 85%, 90%, 91%, 92%, 93%, 94%, 95%, 96%, 97%, 98%, or 99% homology to a naturally occurring cytokine and maintains at least 60%, 70%, 80%, 85%, 90%, 91%, 92%, 93%, 94%, 95%, 96%, 97%, 98%, or 99% activity as compared to the naturally occurring cytokine, as measured by an appropriate in vitro or in vivo assay (e.g., modulation of one or more SOCS genes, phosphorylation of STAT5). In some embodiments, a cytokine mimetic can include one or more structural modifications as compared to the naturally occurring cytokine such as, but not limited to, amino acid sequence, protein folding, binding or receptor sites. In another embodiment, a cytokine mimetic can include modulation of one or more properties as compared to the naturally occurring cytokine such as, but not limited to, efficacy, stability, specificity, immunogenicity or pharmacokinetics. In one embodiment, a cytokine mimetic can include modulation of one or more properties as compared to the naturally occurring cytokine selected from the group consisting of efficacy, stability, specificity, immunogenicity or pharmacokinetics, and wherein the cytokine mimetic retains at least 60%, 70%, 80%, 85%, 90%, 95%, 99%, equivalent, or superior functionality to the corresponding naturally occurring cytokine under comparable conditions. In one embodiment, a cytokine mimetic can include a derivative of a naturally occurring cytokine such as IL-7 or TSLP. In another embodiment, a cytokine mimetic is a naturally occurring cytokine that is artificially manipulated such that its primary structure is altered, conjugated, and/or incorporated into a fusion partner such that a recombinant cytokine is formed. In some embodiments, a cytokine mimetic can include a full-length glycosylated cytokine molecule (e.g., glycosylated-TSLP). In another embodiment, a cytokine mimetic can include a truncated form of the naturally occurring cytokine bound to polyethylene glycol to form a truncated PEGylated cytokine mimetic (e.g., PEGylated-TSLP). In some embodiments, the cytokine mimetic is derived from human TSLP. In another embodiment, the cytokine mimetic is derived from IL-7.

As used herein, the term "thymic stromal lymphopoietin" or "TSLP" refers to a protein belonging to the cytokine family known to play a role in the maturation of T cell populations through activation of antigen presenting cells. TSLP is produced predominantly through non-hematopoietic cells such as fibroblasts, stromal cells and epithelial cells. The cytokine TSLP signals through a heterodimer receptor complex composed of TSLP and IL-7Rα. In humans, TSLP is encoded by the TSLP gene (NCBI Gene ID: 85480). The protein sequence for human TSLP is provided in Table 1 as SEQ ID NO:1 (UniProt: Q969D9). TSLP is known to occur in at least two isoforms (NCBI Reference Sequence: NP_149024.1 and NP_612561.2). The complete coding sequence of human TSLP is provided as BC040592.1 and CCCDS4101.1. Other transcript variants are provided as NM_033035.4 and NM_138551.4. In some embodiments, a CRLF2 gene or protein to be detected according to the methods described herein is a variant having at least 70%, at least 75% at least 80%, at least 85%, at least 90%, at least 91%, at least 92%, at least 93%, at least 94%, at least 95%, at least 96%, at least 97%, at least 98%, or at least 99% identity to a naturally occurring TSLP gene or protein set forth in any of NCBI GenBank Accession Nos. NP_149024.1, NP_612561.2, BC040592.1, CCCDS4101.1, NM_033035.4, NM_138551.4 or UniProt Q969D9.

As used herein, the term "epidermal growth factor" or "EGF" refers to a protein belonging to the EGF-family of proteins (including heparin-binding EGF-like growth factor, transforming growth factor, epigen, betacellulin and neuregulin's) known to play a role in cell growth and differentiation by binding to its receptor, epidermal growth factor receptor (EGFR). In humans, EGF is encoded by the EGF gene (NCBI Gene ID: 1950. The protein sequence for human EGF is provided in Table 1 as SEQ ID NO:2 (UniProt: P01133). EGF is known to occur in at least three isoforms (NCBI Reference Sequence: NP_001954.2 NP_001343950.1 NP_001171601.1 and NP_001171602.1). The complete coding sequence of human EGF is provided as CCCDS3689.1. Other transcript variants are provided as NM_001963.5, NM_001357021.1, NM_001178131.2 and NM_001178130.2. In some embodiments, a EGF gene or protein to be detected according to the methods described herein is a variant having at least 70%, at least 75% at least 80%, at least 85%, at least 90%, at least 91%, at least 92%, at least 93%, at least 94%, at least 95%, at least 96%, at least 97%, at least 98%, or at least 99% identity to a naturally occurring EGF gene or protein set forth in any of NCBI GenBank Accession Nos. NCBI Reference Sequence: NP_001954.2 NP_001343950.1 NP_001171601.1, NP_001171602.1, CCCDS3689.1, NM_001963.5, NM_001357021.1, NM_001178131.2, NM_001178130.2 or UniProt P01133.

As used herein, the term "Interleukin-7" or "IL-7" refers to a protein that is a hematopoietic growth factor secreted by stromal cells in the bone marrow and thymus. In humans, IL-7 is encoded by the IL-7 gene (NCBI Gene ID: 3574). The protein sequence for human IL-7 is provided in Table 1 as SEQ ID NO:3 (UniProt: P13232). IL-7 is known to occur in at least four isoforms (NCBI Reference Sequence: NP_000871.1, NP_01186815.1, NP_01186816,1 and NP_001186817.1). The complete coding sequence of human IL-7 is provided as CCDS6224.1. Other transcript variants are provided as NM_0008890.3, NM_001199886.1, NM_001199887.1 and NM_001199888.1. In some embodiments, a IL-7 gene or protein to be detected according to the methods described herein is a variant having at least 70%, at least 75% at least 80%, at least 85%, at least 90%, at least 91%, at least 92%, at least 93%, at least 94%, at least 95%, at least 96%, at least 97%, at least 98%, or at least 99% identity to a naturally occurring IL-7 gene or protein set forth in any of NCBI GenBank Accession Nos.: NP_000871.1, NP_01186815.1, NP_01186816,1, NP_001186817.1, CCCDS4101.1, CCDS6224.1, NM_0008890.3, NM_001199886.1, NM_001199887.1, NM_001199888.1 or UniProt P13232.

As used herein, the term "cytokine receptor-like factor 2" or "CRLF2" refers to a protein that in humans is encoded by the gene CRLF2 (NCBI Gene ID: 64109) and is a receptor for TSLP. CRLF2 forms a functional complex with TSLP and IL-7R alpha which is capable of stimulating cell proliferation through activation of STAT3 and STAT5. CRLF2 also activates JAK2. The protein sequence for CRLF2 is provided in Table 1 as SEQ ID NO:4 (UniProt: Q9HC73). CRLF2 is known to occur in at least two isoforms (NCBI Reference Sequence: NP_001012288.2 and NP_071431.2). The complete coding sequence of CRLF2 is provided as CCCDS75945.1. Other transcript variants are provided as NM_001012288.2 and NM_022148.3 In some embodiments, a CRLF2 gene or protein to be detected according to the methods described herein is a variant having at least 70%, at least 75% at least 80%, at least 85%, at least 90%, at least 91%, at least 92%, at least 93%, at least 94%, at least 95%, at least 96%, at least 97%, at least 98%, or at least 99% identity to a naturally occurring CRLF2 gene or protein set forth in any of NCBI GenBank Accession Nos NP_001012288.2, NP_071431.2, CCCDS75945.1, NM_001012288.2, NM_022148.3, NCBI Gene ID: 64109 or UniProt: Q9HC73.

As used herein, the term "interleukin 7 receptor alpha" or "IL-7Rα" refers to a protein that in humans is encoded by the gene IL-7Rα (NCBI Gene ID: 3575) and is a receptor for IL-7. IL-7Rα forms a functional complex with TSLP and CRLF2 which is capable of stimulating cell proliferation through activation of STAT3 and STAT5. CRLF2 also activates JAK1. The protein sequence for IL-7Rα is provided in Table 1 as SEQ ID NO:5. Uniprot: P16871). IL-7Rα is known to occur in at least one isoform (NCBI Reference Sequence: NCBI NP_002176.2). The complete coding sequence of IL-7Rα is provided as CCCDS3911.1. Other transcript variants are provided as NM_002185.4. In some embodiments, a IL-7Rα gene or protein to be detected according to the methods described herein is a variant having at least 70%, at least 75% at least 80%, at least 85%, at least 90%, at least 91%, at least 92%, at least 93%, at least 94%, at least 95%, at least 96%, at least 97%, at least 98%, or at least 99% identity to a naturally occurring IL-7Rα gene or protein set forth in any of NCBI GenBank Accession Nos NCBI NP_002176.2, CCCDS3911.1, NM_002185.4, NCBI Gene ID: 3575 or UniProt: P16871.

As used herein, the term "epidermal growth factor receptor" or "EGFR" refers to a protein that in humans is encoded by the gene EGFR (NCBI Gene ID: 1956) and is a receptor for EGF. The gene sequence for EGFR is provided in Table 1 as SEQ ID NO:6 (UniProt: P00533). EGFR is known to occur in at least eight isoforms (NCBI Reference Sequences: NCBI NP_001333826.1, NP_00133827.1, NP_00133828.1, NP_00133829.1, NP_00133870.1, NP_005219.2, NP_958439.1, NP_958440.1, and NP_958441.1). The complete coding sequence of EGFR is provided as CCCDS5514.1. Other transcript variants are provided as NM_005228.4, NM_001346897.1, NM_001346898.1, NM_001346899.1, NM_001346900.1, NM_001346941.1, NM_201282.1, NM_201283.1 and NM_201284.1. In some embodiments, an EGFR gene or protein to be detected according to the methods described herein is a variant having at least 70%, at least 75% at least 80%, at least 85%, at least 90%, at least 91%, at least 92%, at least 93%, at least 94%, at least 95%, at least 96%, at least 97%, at least 98%, or at least 99% identity to a naturally occurring EGFR gene or protein set forth in any of NCBI GenBank Accession Nos NP_001333826.1, NP_00133827.1, NP_00133828.1, NP_00133829.1, NP_00133870.1, NP_005219.2, NP_958439.1, NP_958440.1, NP_958441.1, CCCDS5514.1., NM_005228.4, NM_001346897.1, NM_001346898.1, NM_001346899.1, NM_001346900.1, NM_001346941.1, NM_201282.1, NM_201283.1, NM_201284.1, NCBI Gene ID: 1956 or UniProt: P00533.

As used herein, the term "Suppressors of Cytokine Signaling" or "SOCS" refers to a family of eight (8) genes involved in inhibiting the JAK-STAT signaling pathway. Disrupted or dysregulated JAK-STAT functionality can result in immune deficiency syndromes and cancers (Aaronson and Horvath, Science, 296, 5573:1653-5 (2002)). The SOCS genes are: suppressor of cytokine signaling 1 (SOCS1), suppressor of cytokine signaling 2 (S0052), suppressor of cytokine signaling 3 (S0053), suppressor of cytokine signaling 4 (S0054), suppressor of cytokine signaling 5 (S0055), suppressor of cytokine signaling 6 (S0056), suppressor of cytokine signaling 7 (S0057), and cytokine inducible SH2 containing protein (CISH, also known as CIS, G18 and CIS-1). As demonstrated herein, the SOCS genes can shut down cytokine signals (e.g., TSLP) by blocking signaling (e.g., CRLF2 or EGFR pathways) and degradation of signaling components.

The expression of SOCS1 (NCBI Gene ID: 8651) is known to be induced by cytokines IL-2, IL-3 and TSLP (See, Trengove and Ward, Am. J. Clin. Exp. Immunol, 2013, February 27; 2(1):1-29 and Qiu et al, Neoplasia, 2012, June; 14(6):547-58). The protein sequence of human SOCS1 is provided in Table 1 as SEQ ID NO: 7 (Uniprot: 015524).

The expression of SOCS2 (NCBI Gene ID: 9021) is known to be induced by cytokines GM-CSF and IL-10. The SOCS2 protein interacts with the cytoplasmic domain of insulin-like growth factor-1 receptor and is thought to be involved in the regulation of IGF1R mediated cell signaling. The gene sequence of human SOCS2 is provided in Table 1 as SEQ ID NO:8 (UnitProt: 014508).

The expression of SOCS3 (NCBI Gene ID: 9021) is known to be induced by cytokines IL-6 and IL-10. The SOCS3 protein can bind to JAK2 kinase and inhibits its activity. The gene sequence of human SOCS3 is provided in Table 1 as SEQ ID NO:9 (UnitProt: 014543).

The expression of CISH (NCBI Gene ID: 1154) is known to be induced by cytokines IL-2, IL-3, GM-CSF and EPO in hematopoietic cells. The CISH protein is a cytokine-inducible negative regulator of cytokine signaling. The gene sequence of human CISH is provided in Table 1 as SEQ ID NO:10 (UnitProt: 014543).

As used herein, the term "cancer" refers to a disease characterized by the uncontrolled growth of aberrant cells. The term includes all known cancers and neoplastic conditions, whether characterized as malignant, benign, and includes cancers of all stages and grades including pre- and post-metastatic cancers. Examples of different types of cancers include, but are not limited to, digestive and gastrointestinal cancers such as gastric cancer (e.g., stomach cancer), colorectal cancer, gastrointestinal stromal tumors, gastrointestinal carcinoid tumors, colon cancer, rectal cancer, anal cancer, bile duct cancer, small intestine cancer, and esophageal cancer; breast cancer; lung cancer; gallbladder cancer; liver cancer; pancreatic cancer; appendix cancer; prostate cancer, ovarian cancer; renal cancer; cancer of the central nervous system; skin cancer (e.g., melanoma); lymphomas; gliomas; choriocarcinomas; head and neck cancers; osteogenic sarcomas; and blood cancers. As used herein, a "tumor" comprises one or more cancerous cells.

As used herein, the term "cancer that expresses a cytokine receptor" refers to a cancer that produces, releases, expresses or causes the expression, production or release (e.g., on the surface of cancer cells) of a cytokine receptor (or a mutated form thereof). In one embodiment, a cancer that expresses a cytokine receptor is a cancer cell that produces, releases or expresses a cytokine receptor (or a mutated form) from the surface of the cancer cell. In another embodiment, a cancer that expresses a cytokine receptor refers to a cancer cell that causes the production, release or expression of a cytokine receptor (or a mutated form) from a non-cancerous cell. In one embodiment, a cancer that expresses a cytokine receptor refers to a cancer cell that spontaneously releases, produces or expresses a cytokine receptor (or a mutated form) from the cancer cell. In another embodiment, a cancer that expresses a cytokine receptor refers to a cancer cell that produces, releases or expresses a cytokine receptor (or a mutated form) during metastasis, cell division or cell repair. In another embodiment, a cancer that expresses a cytokine receptor refers to a cancer cell that produces, releases or expresses a cytokine receptor (or a mutated form) as a result of stimulation, infection or inflammation. In some embodiments, the cancer that expresses a cytokine receptor is selected from the following cancers: carcinoma, leukemia, lymphoma, myeloma, sarcoma or mesothelioma. In some embodiments, the cancer that expresses a cytokine receptor is a bladder cancer, breast cancer, uterine cancer, cervical cancer, ovarian cancer, prostate cancer, testicular cancer, esophageal cancer, gastrointestinal cancer, pancreatic cancer, colorectal cancer, colon cancer, kidney cancer, head and neck cancer, lung cancer, stomach cancer, germ cell cancer, bone cancer, liver cancer, thyroid cancer, skin cancer (e.g., melanoma), neoplasm of the central nervous system, lymphoma, leukemia, myeloma, or sarcoma. In some embodiments, the cancer that expresses a cytokine receptor is a solid tumor (e.g., a lung, cervical or ovarian solid tumor). In some embodiments, the cancer that expresses a cytokine receptor is a blood cancer, e.g., a leukemia, a lymphoma, or a myeloma. In one embodiment, a cancer that expresses a cytokine receptor is a leukemia. In some embodiments, a cancer that expresses a cytokine receptor includes an acute lymphoblastic leukemia (ALL). In one embodiment, a cancer that expresses a cytokine receptor is a B-cell type ALL, Philadelphia chromosome-like acute lymphoblastic leukemia (Ph-like B-cell type ALL), T cell type ALL, or acute myeloid leukemia. In one embodiment, a cancer that express a cytokine receptor is a leukemia cell present in the bone marrow or lymphatic system of a human adult or juvenile. In some embodiments, a cancer that express a cytokine receptor is a leukemia cell present in the bone marrow or lymphatic system of a Hispanic human adult or juvenile. In some embodiments, a cancer that expresses a cytokine receptor is associated with the JAK-STAT pathway. In one embodiment, a cancer that expresses a cytokine receptor expresses the cytokine receptor IL-7R alpha (IL-7Rα) or a mutated form thereof. In another embodiment, a cancer that expresses a cytokine receptor expresses the cytokine receptor CRLF2 or a mutated form thereof. In another embodiment, a cancer that expresses a cytokine receptor expresses the cytokine receptor EGFR or a mutated form thereof.

In some embodiments, a cancer that expresses a cytokine receptor can be determined by measuring the level of cytokine receptor released from one or more cancer cells. In some embodiments, the amount of cytokine receptor expressed by a cancer cell can be measured in vitro using plasma or sera samples (See., Ho et al., *Cancer Epidermiol. Biomarkers Prev.* 2014 January:23(1):179-188). In one embodiment, the amount of cytokine receptor expressed by a cancer cell can be measured in vitro using flow cytometry. In yet other embodiments, the amount of cytokine receptor expressed by a cancer cell can be measured using a cytokine detection assay, ELISA assay (e.g., for human interleukins), ELISpot assay (e.g., for rat interferons), antibody array, bead-based array, or cytokine array for mouse (e.g., using cell culture or sera samples).

As used herein, the term "cancer that expresses CRLF2" refers to a cancer that has a detectable level of expression of the cytokine receptor, cytokine receptor-like factor-2 (CRLF2) (either wild-type or a mutated form). In some embodiments, a cancer has a detectable level of expression of CRLF2 when at least 0.1% of cells in a sample of the cancer tissue are positive for CRLF2 expression. In some embodiments, a cancer that expresses CRLF2 has a level of expression of CRLF2 that is at least 5%, 10%, 15%, 20%, 30%, 40%, 50%, 60%, 70%, 80%, 90%, 100%, 150%, or 200% greater than the level of CRLF2 expression in a control (e.g., a non-diseased cell or tissue that does not express CRLF2 or a cancer type that is known not to express CRLF2).

As used herein, the term "cancer characterized by overexpression of CRLF2" refers to a cancer (e.g., one or more cancer cells) that overexpresses CRLF2 by at least 4-fold as compared to CRLF2 expression of a control sample or cell (e.g., one or more non-cancerous cells) (See., Harvey et al., *Blood,* 2010 Jul. 1:115(26):5312-21 and Ge et al., *Oncotarget,* 2016 Aug. 2; 7(31):49722-49732). In some embodiments, the overexpression of CRLF2 is at least 4-, 5-, 10-, 15-, 20-, 25-, 50-, 75-, 100-fold, or greater than as compared to CRLF2 expression of a control sample or cell (e.g., one or more non-cancerous cells). In one embodiment, a cancer characterized by overexpression of CRLF2 is a cancer that expresses CRLF2 or a mutated form of CRLF2 on the surface of the cancer cell. Overexpression of CRLF2 (e.g., a >4-fold increase in mRNA expression of CRLF2 as compared to the mean mRNA expression of CRLF2 from a control sample of normal tissue of the same type) (See., Harvey et al., *Blood,* 2010 Jul. 1:115(26):5312-21 and Ge et al., *Oncotarget,* 2016 Aug. 2; 7(31):49722-49732) is associated with distinct clinico-biological features and unfavorable prognosis. CRLF2 is therefore a relevant prognostic marker, particularly in acute lymphoblastic leukemia's (see., Chiaretti et al., *Leukemia Research,* 41, February 2016: 36-42). Quantitation of CRLF2 mRNA or protein expression can be detected by various methods known in the art including, but not limited to, quantitative RT-PCR and flow cytometry (see Russell et al., *Blood.* 2009; 114(13):2693).

In one embodiment, a cancer that expresses CRLF2 is a cancer cell that expresses CRLF2 or a mutated form of CRLF2 from the surface of the cancer cell. In some embodiments, a cancer that expresses CRLF2 or a mutated form of CRLF2 is selected from: carcinoma, leukemia, lymphoma, myeloma, sarcoma or mesothelioma. In some embodiments, a cancer that expresses CRLF2 is a bladder cancer, breast cancer, uterine cancer, cervical cancer, ovarian cancer, prostate cancer, testicular cancer, esophageal cancer, gastrointestinal cancer, pancreatic cancer, colorectal cancer, colon cancer, kidney cancer, head and neck cancer, lung cancer, stomach cancer, germ cell cancer, bone cancer, liver cancer, thyroid cancer, skin cancer (e.g., melanoma), neoplasm of the central nervous system, lymphoma, leukemia, myeloma, or sarcoma. In some embodiments, a cancer that expresses CRLF2 is a solid tumor (e.g., a lung, cervical or ovarian solid tumor). In some embodiments, a cancer that expresses CRLF2 is a blood cancer, e.g., a leukemia, a lymphoma, or a myeloma. In one embodiment, a cancer that expresses CRLF2 is a leukemia. In some embodiments, a cancer that expresses CRLF2 is acute lymphoblastic leukemia (ALL). In one embodiment, a cancer that expresses CRLF2 is a B-cell type ALL, Philadelphia chromosome-like acute lymphoblastic leukemia (Ph-like B-cell type ALL), T cell type ALL, or acute myeloid leukemia. High levels (e.g., several-fold increase in mRNA or protein expression) of CRLF2 are associated with distinct clinico-biological features and unfavorable prognosis. CRLF2 appears to be overexpressed at difference frequencies in B-ALLs depending on the subtype (Russell et al., *Blood.* 2009; 114(13):2688-98). Additionally, overexpression of CRLF2 has been especially linked to carcinogenesis in patients with trisomy 21 (Mulligan et al., *Nat. Genet.* 2009; 41(11):1243-6). CRLF2 is therefore a relevant prognostic marker, particularly in acute lymphoblastic leukemia's (see., Chiaretti et al., *Leukemia Research,* 41, February 2016: 36-42). Quantitation of CRLF2 can be detected by various methods in the art including, but not limited to, measuring CRLF2 mRNA expression by quantitative RT-PCR or flow cytometry (see Russell et al., *Blood.* 2009; 114(13):2693).

As used herein, the term "cancer that expresses EGFR" refers to a cancer that has a detectable level of expression of the cytokine receptor, epidermal growth factor receptor (EGFR) (either wild-type or a mutated form). In some embodiments, a cancer has a detectable level of expression of EFGR when at least 0.1% of cells in a sample of the cancer tissue are positive for EGFR expression. In some embodiments, a cancer that expresses EGFR has a level of expression of EGFR that is at least 5%, 10%, 15%, 20%, 30%, 40%, 50%, 60%, 70%, 80%, 90%, 100%, 150%, or 200% greater than the level of EGFR expression in a control (e.g., a non-diseased cell or tissue that does not express EGFR or a cancer type that is known not to express EGFR.

As used herein, the term "cancer characterized by overexpression of EGFR" refers to a cancer (e.g., one or more cancer cells) that overexpresses EGFR as compared to EGFR expression of a control sample or cell (e.g., one or more non-cancerous cells). In some embodiments, the overexpression of EGFR is at least 2-, 3-, 4-, 5-, 10-, 15-, 20-, 25-, 50-, 75-, 100-fold, or greater than as compared to EGFR expression of a control sample or cell (e.g., one or more non-cancerous cells). In one embodiment, a cancer characterized by overexpression of EGFR is a cancer that expresses EGFR at a level higher than normal (non-cancerous) tissue (e.g., statistically significant) or a mutated form of EGFR on the surface of the cancer cell. Quantitation of EGFR mRNA or protein expression can be detected by various methods known in the art including, but not limited to, quantitative RT-PCR, immunohistochemistry and flow cytometry (see Mitsuhashi et al., *Gynecologic Oncology*, 2003, 89:480-485 and Dennis et al., *Cancer Research*, 2004, 64:2047-53).

In one embodiment, a cancer that expresses EGFR is a cancer cell that expresses EGFR or a mutated form of EGFR from the surface of the cancer cell. In some embodiments, a cancer that expresses EGFR or a mutated form of EGFR is selected from: carcinoma, leukemia, lymphoma, myeloma, sarcoma or mesothelioma. In some embodiments, a cancer that expresses EGFR is a bladder cancer, breast cancer, uterine cancer, cervical cancer, ovarian cancer, prostate cancer, testicular cancer, esophageal cancer, gastrointestinal cancer, pancreatic cancer, colorectal cancer, colon cancer, kidney cancer, head and neck cancer, lung cancer, stomach cancer, germ cell cancer, bone cancer, liver cancer, thyroid cancer, skin cancer (e.g., melanoma), neoplasm of the central nervous system, lymphoma, leukemia, myeloma, or sarcoma. In some embodiments, a cancer that expresses EGFR is a solid tumor (e.g., a lung, cervical or ovarian solid tumor). In some embodiments, a cancer that expresses EGFR is a blood cancer, e.g., a leukemia, a lymphoma, or a myeloma. In one embodiment, a cancer that expresses EGFR is a leukemia.

As used herein, the term "cancer that expresses IL-7Rα" refers to a cancer that has a detectable level of expression of the cytokine receptor, interleukin 7 receptor alpha (IL-7Rα) (either wild-type or a mutated form). In some embodiments, a cancer has a detectable level of expression of IL-7Rα when at least 0.1% of cells in a sample of the cancer tissue are positive for IL-7Rα expression. In some embodiments, a cancer that expresses IL-7Rα has a level of expression of IL-7Rα that is at least 5%, 10%, 15%, 20%, 30%, 40%, 50%, 60%, 70%, 80%, 90%, 100%, 150%, or 200% greater than the level of IL-7Rα expression in a control (e.g., a non-diseased cell or tissue that does not express IL-7Rα or a cancer type that is known not to express IL-7Rα.

As used herein, the term "cancer characterized by overexpression of IL-7Rα" refers to a cancer (e.g., one or more cancer cells) that overexpresses IL-7Rα at a higher level (e.g., statistically significant) as compared to IL-7Rα expression of a control sample or cell (e.g., one or more non-cancerous cells) or mutant IL-7Rα. In some embodiments, the overexpression of IL-7Rα is at least 2-, 3-, 4-, 5-, 10-, 15-, 20-, 25-, 50-, 75-, 100-fold, or greater than as compared to IL-7Rα expression of a control sample or cell (e.g., one or more non-cancerous cells). In one embodiment, a cancer characterized by overexpression of IL-7Rα is a cancer that expresses IL-7Rα or a mutated form of IL-7Rα on the surface of the cancer cell. Quantitation of IL-7Rα mRNA or protein expression can be detected by various methods known in the art including, but not limited to, flow cytometry (see Ryan et al., *Blood*. 1997; 89:929-940).

In one embodiment, a cancer that expresses IL-7Rα is a cancer cell that expresses IL-7Rα or a mutated form of IL-7Rα from the surface of the cancer cell. In some embodiments, a cancer that expresses IL-7Rα or a mutated form of IL-7Rα is selected from: carcinoma, leukemia, lymphoma, myeloma, sarcoma or mesothelioma. In some embodiments, a cancer that expresses IL-7Rα is a bladder cancer, breast cancer, uterine cancer, cervical cancer, ovarian cancer, prostate cancer, testicular cancer, esophageal cancer, gastrointestinal cancer, pancreatic cancer, colorectal cancer, colon cancer, kidney cancer, head and neck cancer, lung cancer, stomach cancer, germ cell cancer, bone cancer, liver cancer, thyroid cancer, skin cancer (e.g., melanoma), neoplasm of the central nervous system, lymphoma, leukemia, myeloma, or sarcoma. In some embodiments, a cancer that expresses IL-7Rα is a solid tumor (e.g., a lung, cervical or ovarian solid tumor). In some embodiments, a cancer that expresses IL-7Rα is a blood cancer, e.g., a leukemia, a lymphoma, or a myeloma. In one embodiment, a cancer that expresses IL-7Rα is a leukemia. In some embodiments, a cancer that expresses IL-7Rα is acute lymphoblastic leukemia (ALL). In one embodiment, a cancer that expresses IL-7Rα is a B-cell type ALL, Philadelphia chromosome-like acute lymphoblastic leukemia (Ph-like B-cell type ALL), T cell type ALL, or acute myeloid leukemia.

The terms "identical" or "percent identity," in the context of two or more polynucleotide or polypeptide sequences, refer to two or more sequences that are the same or have a specified percentage of amino acid residues or nucleotides that are the same (e.g., about 60% identity, preferably 65%, 70%, 75%, 80%, 85%, 90%, 91%, 92%, 93%, 94%, 95%, 96%, 97%, 98%, 99%, or higher identity) over a specified region. Methods for comparing polynucleotide or polypeptide sequences and determining percent identity are described in the art. See, e.g., Roberts et al., *BMC Bioinformatics*, 7:382, 2006, incorporated by reference herein.

The terms "protein" and "polypeptide" are used interchangeably herein and refer to a polymer of amino acid residues. As used herein, the terms encompass amino acid chains of any length, including full-length proteins and truncated proteins.

As used herein, the term "compound" refers to any molecule, either naturally occurring or synthetic, e.g., peptide, protein, oligopeptide (e.g., from about 5 to about 300 amino acids in length, preferably from about 10 to 200 or 20 to 100 amino acids in length, preferably 12, 15, or 18 amino acids in length), small organic molecule, polysaccharide, peptide, circular peptide, peptidomimetic, lipid, fatty acid, siRNA, polynucleotide, oligonucleotide, etc.

As used herein, an "analog" refers to a compound that is a structural derivative of a parent compound, in which one or more atoms or functional groups is different from the parent compound. In some embodiments, an analog has comparable or superior stability, solubility, efficacy, half-life, and the like as compared to the parent compound.

As used herein, a "subject" is a mammal, in some embodiments, a human. Mammals can also include, but are not limited to, farm animals (e.g., cows, pigs, horses, chickens, etc.), sport animals, pets, primates, horses, dogs, cats, mice and rats.

As used herein, a "sample" refers to a bodily tissue or fluid obtained from a human or non-human mammalian subject. In some embodiments, a sample comprises blood, blood fractions, or blood products (e.g., serum, plasma, platelets, red blood cells, peripheral blood mononuclear cells, and the like), sputum or saliva, stool, urine, other biological fluids (e.g., lymph, saliva, prostatic fluid, gastric fluid, intestinal fluid, renal fluid, lung fluid, cerebrospinal fluid, and the like), tissue (e.g., kidney, lung, liver, heart, brain, nervous tissue, thyroid, eye, skeletal muscle, cartilage, or bone tissue), or cultured cells (e.g., primary cultures, explants, transformed cells, or stem cells). In some embodiments, a sample comprises blood.

As used herein, the terms "treatment," "treating," and "treat" refer to any indicia of success in the treatment or amelioration of an injury, disease, or condition, including any objective or subjective parameter such as abatement; remission; diminishing of symptoms or making the injury, disease, or condition more tolerable to the subject; slowing in the rate of degeneration or decline; making the final point of degeneration less debilitating; and/or improving a subject's physical or mental well-being.

As used herein, the term "pharmaceutical composition" refers to a composition suitable for administration to a subject. In general, a pharmaceutical composition is sterile, and preferably free of contaminants that are capable of eliciting an undesirable response with the subject. Pharmaceutical compositions can be designed for administration to subjects in need thereof via a number of different routes of administration, including oral, intravenous, buccal, rectal, parenteral, intraperitoneal, intradermal, intratracheal, intramuscular, subcutaneous, inhalational, and the like.

III. Diagnostic & Detection Methods

In one aspect, methods of diagnosing a subject as having cancer or detecting cancer in a subject are provided. In some embodiments, the methods described herein relate to diagnosing or detecting cancer such as leukemias and solid tumors. In some embodiments, the methods described herein relate to diagnosing or detecting cancers that expresses a cytokine receptor, such as EGFR, CRLF2 and/or IL-7Rα. In another aspect, methods of diagnosing or detecting cancer in a sample from a subject have been found to be associated with the overexpression of CRLF2, EGFR and/or IL-7Rα in the sample.

As described herein, it has been found that the expression of CRLF2, EGFR and/or IL-7Rα are dysregulated in cancer cells such as leukemias and solid tumors. Thus, in one aspect, the disclosure provides methods of diagnosing cancer in a subject by contacting a sample from the subject with an antibody that binds to CRLF2 that is expressed on a surface of a cell from the sample, and detecting CRLF2 in the sample, thereby diagnosing the cancer in the subject. In some embodiments, the method further comprises comparing the binding of CRLF2 in the sample to a control sample (e.g., a sample from a healthy subject known not to have cancer), wherein an increase in the binding of CRLF2 in the sample as compared to the control sample, identifies the subject from whom the sample was obtained as having cancer.

In another aspect, the disclosure provides methods of diagnosing cancer in a subject by contacting a sample from the subject with an antibody that binds to IL-7Rα that is expressed on a surface of a cell from the sample, and detecting IL-7Rα in the sample, thereby diagnosing the cancer in the subject. In some embodiments, the method further comprises comparing the binding of IL-7Rα in the sample to a control sample (e.g., a sample from a healthy subject known not to have cancer), wherein an increase in the binding of IL-7Rα in the sample as compared to the control sample, identifies the subject from whom the sample was obtained as having cancer.

As described herein, it has been found that the expression of CRLF2 and IL-7Rα is dysregulated in certain forms of cancer including leukemias and solid tumors. Thus, in one aspect, the disclosure provided methods of diagnosing a cancer subtype that expresses one or more of these cytokine receptors by detecting, in a sample from a subject, changes in levels of expression of one or both of the CRLF2 and IL-7Rα proteins as measured by the binding of the CRLF2 and IL-7Rα proteins to anti-CRLF2 and anti-IL-7Rα antibodies, respectively. In some embodiments, the method comprises:

contacting a sample from the subject with an anti-CRLF2 and/or anti-IL-7Rα antibody; and detecting CRLF2 and IL-7Rα proteins in the sample, thereby diagnosing the cancer in the subject.

In some embodiments, the detecting includes, but is not limited to, measuring in the sample from the subject the level of binding of CRLF2 and/or IL-7Rα proteins on the surface of cells in the sample to anti-CRLF2 and/or anti-IL-7Rα antibodies; and comparing the level of binding of CRLF2 and/or IL-7Rα proteins to anti-CRLF2 and/or anti-IL-7Rα antibodies in the sample from the subject to a control sample (e.g., a healthy subject known to not have cancer);

wherein increased binding of CRLF2 and/or IL-7Rα proteins to anti-CRLF2 and/or anti-IL-7Rα antibodies in the sample from the subject, as compared to the control sample, identifies the subject as having cancer.

In some embodiments, once a subject has been identified as having increased binding of binding of CRLF2 and/or IL-7Rα proteins to anti-CRLF2 and/or anti-IL-7Rα antibodies, and has been identified as having cancer, the method further comprises administering one or more therapeutic interventions to the subject. In some embodiments, the therapeutic intervention is an intervention described in Section V below.

In another aspect, methods of detecting the level of expression of CRLF2 and/or IL-7Rα and the level of activity of CRLF2 and/or IL-7Rα in a sample from a subject are provided. In some embodiments, methods of detecting the level of expression of CRLF2 and/or IL-7Rα are provided. In some embodiments, the method comprises:

obtaining a sample from the subject; and measuring in the sample from the subject one or both of (i) the level of expression of a CRLF2 polynucleotide (e.g., mRNA) or protein, and (ii) the level of expression of a IL-7Rα polynucleotide (e.g., mRNA) or protein. In some embodiments, the measuring step comprises detecting the level of cell surface expression of CRLF2 and/or IL-7Rα.

In some embodiments, methods of detecting the level of activity of CRLF2 and/or IL-7Rα are provided. In some embodiments, the method comprises:

obtaining a sample from the subject; and measuring in the sample from the subject one or more of (i) a level of phosphorylation of STAT5; and (ii) a level of phosphorylation of ribosomal protein S6.

In some embodiments, the methods comprise measuring the level of CRLF2 polynucleotide, e.g., mRNA. In some embodiments, the methods comprise measuring the level of CRLF2 protein. In some embodiments, a subject (also referred to herein as a "test subject") is diagnosed as having cancer (e.g., leukemia or solid tumor) if the subject has a level of expression of CRLF2 mRNA or protein that is above a reference value, e.g., a reference value that is determined from the level of expression of CRLF2 mRNA or protein for a population of healthy subjects who are age-matched to the test subject. In some embodiments, a subject is diagnosed as having cancer if the level of CRLF2 mRNA or protein in the sample from the subject is increased by at least 10%, at least 20%, at least 30%, at least 40%, at least 50%, at least 60%, at least 70%, at least 80%, at least 90% or more as compared to the reference value. In some embodiments, a subject is diagnosed as having cancer if the level of CRLF2 mRNA or protein in the sample from the subject is increased by at least 2-fold, 3-fold, 4-fold, 5-fold, 6-fold, 7-fold, 8-fold, 9-fold, 10-fold or more as compared to the reference value.

In some embodiments, the methods comprise measuring the level of IL-7Rα polynucleotide, e.g., mRNA. In some embodiments, the methods comprise measuring the level of IL-7Rα protein. In some embodiments, a subject (also referred to herein as a "test subject") is diagnosed as having cancer (e.g., leukemia or solid tumor) if the subject has a level of expression of IL-7Rα mRNA or protein that is above a reference value, e.g., a reference value that is determined from the level of expression of IL-7Rα mRNA or protein for a population of healthy subjects who are age-matched to the test subject. In some embodiments, a subject is diagnosed as having cancer if the level of IL-7Rα mRNA or protein in the sample from the subject is increased by at least 10%, at least 20%, at least 30%, at least 40%, at least 50%, at least 60%, at least 70%, at least 80%, at least 90% or more as compared to the reference value. In some embodiments, a subject is diagnosed as having cancer if the level of IL-7Rα mRNA or protein in the sample from the subject is increased by at least 2-fold, 3-fold, 4-fold, 5-fold, 6-fold, 7-fold, 8-fold, 9-fold, 10-fold or more as compared to the reference value.

Measuring Polynucleotide Expression

In some embodiments, the level of polynucleotide (e.g., mRNA) expression is determined for one or both of CRLF2 and IL-7Rα. Polynucleotide (e.g., mRNA) expression can be analyzed using routine techniques such as reverse transcription polymerase chain reaction (RT-PCR), Real-Time reverse transcription polymerase chain reaction (Real-Time RT-PCR), semi-quantitative RT-PCR, quantitative polymerase chain reaction (qPCR), quantitative RT-PCR (qRT-PCR), multiplexed branched DNA (bDNA) assay, microarray hybridization, or sequence analysis (e.g., RNA sequencing ("RNA-Seq")). Methods of quantifying polynucleotide expression are described, e.g., in Fassbinder-Orth, *Integrative and Comparative Biology*, 2014, 54:396-406; Thellin et al., *Biotechnology Advances*, 2009, 27:323-333; and Zheng et al., *Clinical Chemistry*, 2006, 52:7 (doi: 10/1373/clinchem.2005.065078).

In some embodiments, real-time or quantitative PCR or RT-PCR is used to measure the level of a polynucleotide (e.g., mRNA) in a biological sample. See, e.g., Nolan et al., *Nat. Protoc*, 2006, 1:1559-1582; Wong et al., *BioTechniques*, 2005, 39:75-75. Quantitative PCR and RT-PCR assays for measuring gene expression are also commercially available (e.g., TaqMan® Gene Expression Assays, ThermoFisher Scientific).

In some embodiments, polynucleotide (e.g., mRNA) expression is measured by sequencing. Non-limiting examples of sequence analysis include Sanger sequencing, capillary array sequencing, thermal cycle sequencing (Sears et al., *Biotechniques*, 13:626-633 (1992)), solid-phase sequencing (Zimmerman et al., *Methods Mol. Cell Biol.*, 3:39-42 (1992)), sequencing with mass spectrometry such as matrix-assisted laser desorption/ionization time-of-flight mass spectrometry (MALDI-TOF/MS; Fu et al., *Nature Biotech.*, 16:381-384 (1998)), sequencing by hybridization (Drmanac et al., *Nature Biotech.*, 16:54-58 (1998), and "next generation sequencing" methods, including but not limited to sequencing by synthesis (e.g., HiSeq™, MiSeq™, or Genome Analyzer, each available from Illumina), sequencing by ligation (e.g., SOLiD™, Life Technologies), ion semiconductor sequencing (e.g., Ion Torrent™, Life Technologies), and pyrosequencing (e.g., 454™ sequencing, Roche Diagnostics). See, e.g., Liu et al., *J. Biomed Biotechnol*, 2012, 2012:251364, incorporated by reference herein. In some embodiments, polynucleotide expression is measuring using RNA-Seq technology. See, e.g., Finotello et al., *Briefings in Functional Genomics*, 2014, doi:10.1093/bfgp/elu035; and Mortazavi et al., *Nat Methods*, 2008, 5:621-628.

A detectable moiety can be used in the assays described herein (direct or indirect detection). A wide variety of detectable moieties can be used, with the choice of label depending on the sensitivity required, ease of conjugation with the probe, stability requirements, and available instrumentation and disposal provisions. Suitable detectable moieties include, but are not limited to, radionuclides, fluorescent dyes (e.g., fluorescein, fluorescein isothiocyanate (FITC), Oregon Green™, rhodamine, Texas red, tetrarhodimine isothiocynate (TRITC), Cy3, Cy5, etc.), fluorescent markers (e.g., green fluorescent protein (GFP), phycoerythrin, etc.), autoquenched fluorescent compounds that are activated by tumor-associated proteases, enzymes (e.g., luciferase, horseradish peroxidase, alkaline phosphatase, etc.), nanoparticles, biotin, digoxigenin, metals, and the like.

Measuring Protein Expression

In some embodiments, the level of protein expression is determined for one or more of CRLF2, IL-7Rα, phosphorylated STAT5, and phosphorylated ribosomal protein S6. Protein expression can be detected and quantified in a sample using routine techniques such as immunoassays, two-dimensional gel electrophoresis, and quantitative mass spectrometry that are known to those skilled in the art. Protein quantification techniques are generally described in "Strategies for Protein Quantitation," *Principles of Proteomics*, 2nd Edition, R. Twyman, ed., Garland Science, 2013. In some embodiments, protein expression is detected by immunoassay, such as but not limited to enzyme immunoassays (EIA) such as enzyme multiplied immunoassay technique (EMIT), enzyme-linked immunosorbent assay (ELISA), IgM antibody capture ELISA (MAC ELISA), and microparticle enzyme immunoassay (MEIA); capillary electrophoresis immunoassays (CEIA); radioimmunoassays (RIA); immunoradiometric assays (IRMA); immunofluorescence (IF); fluorescence polarization immunoassays (FPIA); and chemiluminescence assays (CL). If desired, such immunoassays can be automated. Immunoassays can also be used in conjunction with laser induced fluorescence (see, e.g., Schmalzing et al., *Electrophoresis*, 18:2184-93 (1997); Bao, *J. Chromatogr. B. Biomed. Sci.*, 699:463-80 (1997)).

Specific immunological binding of an antibody to a protein can be detected directly or indirectly. Direct labels include fluorescent or luminescent tags, metals, dyes, radionuclides, and the like, attached to the antibody. An antibody labeled with iodine-125 ($^{125}$I) can be used. A chemiluminescence assay using a chemiluminescent antibody specific for the protein marker is suitable for sensitive, non-radioactive detection of protein levels. An antibody labeled with fluorochrome is also suitable. Examples of fluorochromes include, without limitation, DAPI, fluorescein, Hoechst 33258, R-phycocyanin, B-phycoerythrin, R-phycoerythrin, rhodamine, Texas red, and lissamine. Indirect labels include various enzymes well known in the art, such as horseradish peroxidase (HRP), alkaline phosphatase (AP), (3-galactosidase, urease, and the like. A horseradish-peroxidase detection system can be used, for example, with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, for example, which yields a soluble product readily detectable at 405 nm. Similarly, a β-galactosidase detection system can be used with the chromogenic substrate o-nitrophenyl-β-D-galactopyranoside (ONPG), which yields a soluble product detectable at 410 nm. A urease detection system can be used with a substrate such as urea-bromocresol purple (Sigma Immunochemicals; St. Louis, MO).

A signal from the direct or indirect label can be analyzed, for example, using a spectrophotometer to detect color from a chromogenic substrate; a radiation counter to detect radiation such as a gamma counter for detection of $^{125}$I; or a fluorometer to detect fluorescence in the presence of light of a certain wavelength. For detection of enzyme-linked antibodies, a quantitative analysis can be made using a spectrophotometer such as an EMAX Microplate Reader (Molecular Devices; Menlo Park, CA) in accordance with the manufacturer's instructions. If desired, the assays can be automated or performed robotically, and the signal from multiple samples can be detected simultaneously. In some embodiments, the amount of signal can be quantified using an automated high-content imaging system. High-content imaging systems are commercially available (e.g., ImageXpress, Molecular Devices Inc., Sunnyvale, CA).

Antibodies can be immobilized onto a variety of solid supports, such as magnetic or chromatographic matrix particles, the surface of an assay plate (e.g., microtiter wells), pieces of a solid substrate material or membrane (e.g., plastic, nylon, paper), and the like. Useful physical formats comprise surfaces having a plurality of discrete, addressable locations, such as protein microarrays, or "protein chips" (see, e.g., Ng et al., *J. Cell Mol. Med.*, 6:329-340 (2002)) and certain capillary devices (see, e.g., U.S. Pat. No. 6,019,944). In these embodiments, each discrete surface location may comprise antibodies to immobilize one or more protein markers for detection at each location. Surfaces may alternatively comprise one or more discrete particles (e.g., microparticles or nanoparticles) immobilized at discrete locations of a surface, where the microparticles comprise antibodies to immobilize one or more protein markers for detection.

The analysis can be carried out in a variety of physical formats. For example, the use of microtiter plates or automation could be used to facilitate the processing of large numbers of test samples.

In some embodiments, protein expression is detected by quantitative mass spectrometry, for example but not limited to, spectral count MS, ion intensities MS, metabolic labeling (e.g., stable-isotope labeling with amino acids in cell culture (SILAC), enzymatic labeling, isotopic labeling (e.g., isotope-coded protein labeling (ICPL) or isotope-coded affinity tags (ICAT)), and isobaric labeling (e.g., tandem mass tag (TMT) or isobaric tags for absolute and relative quantification (iTRAQ)). See, e.g., Bantscheff et al., *Anal Bioanal Chem*, 2012, 404:949 (doi:10.1007/s00216-012-6203-4); and Nikolov et al., *Methods in Molecular Biology*, 2012, 893:85-100.

In some embodiments, the diagnostic and detection methods disclosed herein comprise detecting for an increased amount of CRLF2 and/or IL-7Rα in a cell sample from the subject. In some embodiments, the method comprises performing flow cytometry on a sample (e.g., a blood sample, e.g., a sample comprising peripheral blood mononuclear cells) to quantify the levels of CRLF2 and/or IL-7Rα fluorescence. In some embodiments, a patient is diagnosed as having cancer if an increased number of cells in the sample from the subject exhibit CRLF2 and/or IL-7Rα fluorescence, relative to a reference value (e.g., a value determined for a population of healthy subjects) or as compared to sample from a control (e.g., a healthy subject known to not have cancer). In some embodiments, a patient is diagnosed as having cancer if at least about 25%, at least about 40%, at least about 50%, at least about 60%, at least about 70% or more of cells in the sample from the subject exhibit CRLF2 and/or IL-7Rα fluorescence.

In some embodiments, the methods of diagnosing a subject as having cancer further comprise detecting the level of CRLF2 that binds to an anti-CRLF2 antibody in the sample from the subject. CRLF2 protein binding can be measured, for example, by immunoassays such as Western blotting, immunoprecipitation, immunofluorescence microscopy, ELISA, flow cytometry, and the like with an antibody that is specific for CRLF2. In some embodiments, CRLF2 binding is measured by flow cytometry (See, e.g., FIG. 13C). Antibodies against CRLF2 are known in the art and are commercially available, e.g., from BioLegend (San Diego, CA), such as Catalog Nos. 660203, 660202, and 651101 and Novus Biologicals (Littleton, CO), such as Catalog Nos. AF981, MAB981, NBP2-29613 and NBP1-76794). In some embodiments, a patient is diagnosed as having cancer if the level of CRLF2 is increased by at least 10%, at least 20%, at least 30%, at least 40%, at least 50%, at least 60%, at least 70%, at least 80%, at least 90% or more as compared to a reference value (e.g., a value determined for a population of healthy subjects) or as compared to the level of CRLF2 binding in a control sample (e.g., a healthy subject known to not have cancer).

Figure 14:
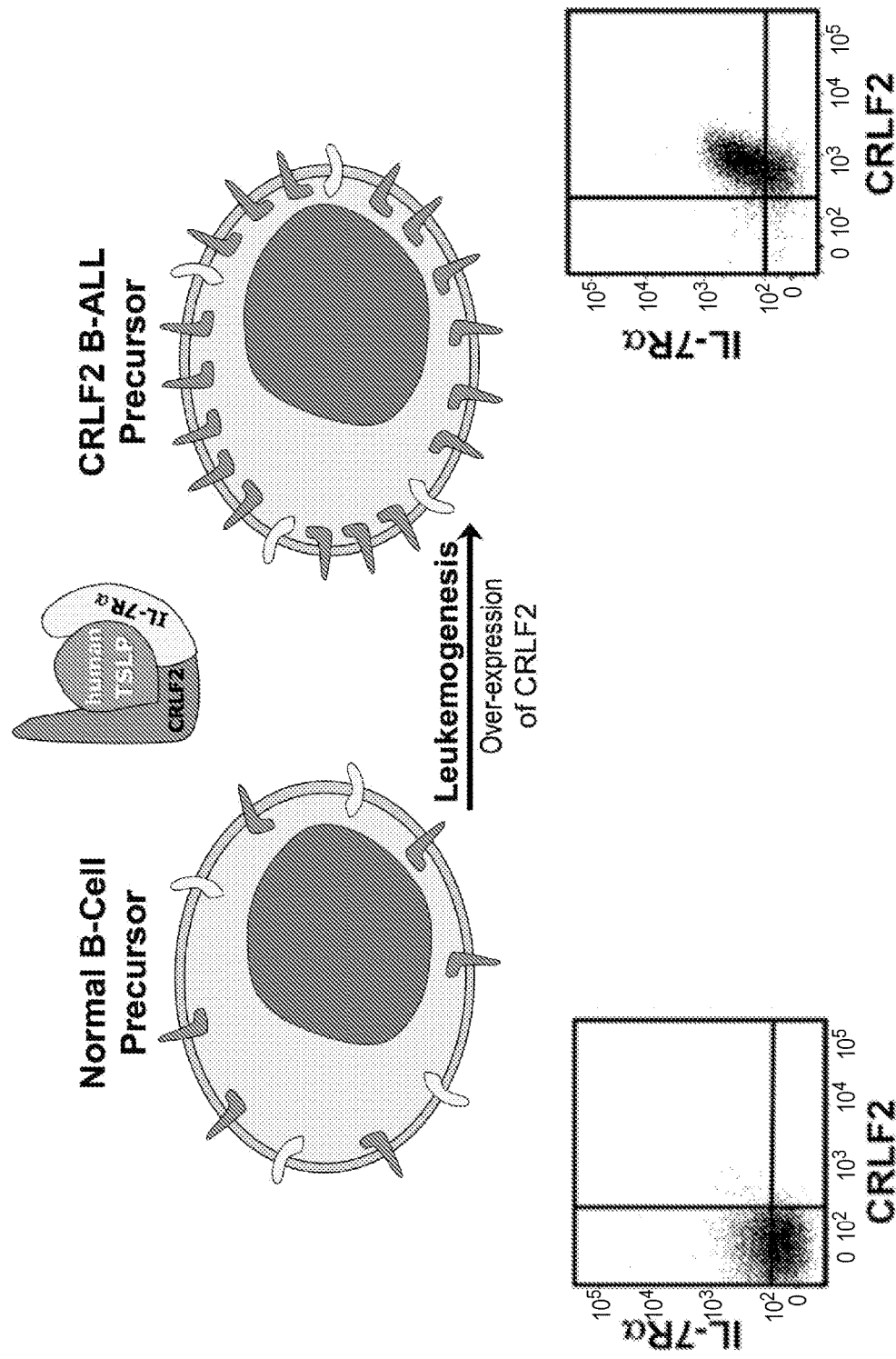
FIG. 14. CRLF2 B-ALL is characterized by CRLF2 expression that is 4-200 fold higher than normal B cell precursors. Schematic depicting CRLF2, IL-7R alpha and TSLP interactions and expression in normal B cell precursors (left) and CRLF2 B-ALL (right). Bottom panels show flow cytometry plots of IL-7R alpha and CRLF2 expression on normal B cell precursors (left panel) and patient CRLF2 B-ALL cells (right panel).

In some embodiments, the methods of diagnosing a subject as having cancer further comprise detecting the level of IL-7Rα that binds to an anti-IL-7Rα antibody in the sample from the subject. IL-7Rα protein binding can be measured, for example, by immunoassays such as Western blotting, immunoprecipitation, immunofluorescence microscopy, ELISA, flow cytometry, and the like with an antibody that is specific for IL-7Rα. In some embodiments, IL-7Rα binding is measured by flow cytometry (See, e.g., FIG. 14). Antibodies against IL-7Rα are known in the art and are commercially available, e.g., from BioLegend (San Diego, CA), such as Catalog Nos. 351315, 351347, 351311, 351346, 351323, and Novus Biologicals (Littleton, CO), such as Catalog Nos. DDX0700P-100, NBP2-22376, AF5607, and MAB4774). In some embodiments, a patient is diagnosed as having cancer if the level of IL-7Rα is increased by at least 10%, at least 20%, at least 30%, at least 40%, at least 50%, at least 60%, at least 70%, at least 80%, at least 90% or more as compared to a reference value (e.g., a value determined for a population of healthy subjects) or as compared to the level of CRLF2 binding in a control sample (e.g., a healthy subject known to not have cancer).

In some embodiments, the methods of diagnosing a subject as having cancer further comprise measuring for the level of STAT5 phosphorylation in the sample from the subject. STAT5 phosphorylation can be measured, for example, by immunoassays such as Western blotting, immunoprecipitation, immunofluorescence microscopy, ELISA, and the like with a phospho-specific antibody that is specific for one or more phosphorylated residues of STAT5. In some embodiments, STAT5 phosphorylation is measured by phosphoprotein analysis with flow cytometry (See, e.g., FIG. 13C). Phospho-specific antibodies against STAT5 are known in the art and are commercially available, e.g., from BioLegend (San Diego, CA), such as Catalog No. 660203, 660202, and 651101. In some embodiments, a patient is diagnosed as having cancer if the level of STAT5 phosphorylation is increased by at least 10%, at least 20%, at least 30%, at least 40%, at least 50%, at least 60%, at least 70%, at least 80%, at least 90% or more as compared to a reference value (e.g., a value determined for a population of healthy subjects) or as compared to the level of STAT5 phosphorylation in a control sample (e.g., a healthy subject known to not have cancer).

In some embodiments, the methods of diagnosing a subject as having cancer further comprise measuring for the level of ribosomal S6 phosphorylation in the sample from the subject. Ribosomal S6 phosphorylation can be measured, for example, by immunoassays such as Western blotting, ELISA, and the like with a phospho-specific antibody that is specific for one or more phosphorylated residues of ribosomal S6. In some embodiments, ribosomal S6 phosphorylation is measured by phosphoprotein analysis with flow cytometry (See, e.g., FIG. 11B). Phospho-specific antibodies against ribosomal S6 are known in the art and are commercially available, e.g., from BioLegend (San Diego, CA), such as Catalog No. 691802. In some embodiments, a patient is diagnosed as having cancer if the level of ribosomal S6 phosphorylation is increased by at least 10%, at least 20%, at least 30%, at least 40%, at least 50%, at least 60%, at least 70%, at least 80%, at least 90% or more as compared to a reference value (e.g., a value determined for a population of healthy subjects) or as compared to the level of ribosomal S6 phosphorylation in a control sample (e.g., a healthy subject known to not have cancer).

Patent Populations and Cancers

In some embodiments, methods of treating a subject having a cancer are provided. In some embodiments, the subject having a cancer is a human. In some embodiments, the subject is an adult human of at least 18 years of age, e.g., at least 30 years of age, at least 50 years of age, or at least 65 years of age. In some embodiments, the subject is a juvenile human under the age of 18. In some embodiments, the subject is a juvenile human between the ages of 0-17, e.g., between the ages of 1 month-24 months, between the ages of 0-6, or between the ages of 2-12, or between the ages of 12-17. In some embodiments, the subject is a Hispanic juvenile human between the ages of 0-17.

In some embodiments, the cancer is bladder cancer, breast cancer, uterine cancer, cervical cancer, ovarian cancer, prostate cancer, testicular cancer, esophageal cancer, gastrointestinal cancer, pancreatic cancer, colorectal cancer, colon cancer, kidney cancer, head and neck cancer, lung cancer, stomach cancer, germ cell cancer, bone cancer, liver cancer, thyroid cancer, skin cancer (e.g., melanoma), neoplasm of the central nervous system, lymphoma, leukemia, myeloma, or sarcoma. In some embodiments, the cancer is a solid tumor. In some embodiments, the solid tumor is a solid tumor selected from ovarian, lung and cervical cancer. In some embodiments, the solid tumor is cervical cancer. In some embodiments, the solid tumor is lung cancer, In some embodiments, the solid tumor is ovarian cancer. In some embodiments, the cancer is a blood cancer, e.g., a leukemia, a lymphoma, or a myeloma. In some embodiments, the cancer is a leukemia. In some embodiments, the leukemia is an acute form. In some embodiments, the leukemia is acute lymphoblastic leukemia (ALL), e.g., B cell acute lymphoblastic leukemia (B-ALL or B-cell type ALL) or Philadelphia chromosome-like (Ph-like) B-cell type ALL. In some embodiments, the leukemia is acute myelogenous leukemia (AML). In some embodiments, the leukemia is a chronic form. In some embodiments, the leukemia is chronic lymphoblastic leukemia (CLL). In some embodiments, the leukemia is chronic myelogenous leukemia (CML).

In some embodiments, the cancer is a cancer that expresses a cytokine receptor, e.g., on the surface of cancer cells. In some embodiments, the cytokine receptor is cytokine receptor-like factor 2 (CRLF2), epidermal growth factor receptor (EGFR) or interleukin-7 receptor-α (IL-7R-α). In some embodiments, the cancer expresses a mutated form of a cytokine receptor (e.g., having one or more genetic alterations, such as point mutations, deletions, additions, or rearrangements), e.g., a mutated form of CRLF2, EGFR or IL-7R-α.

In some embodiments, the cancer is a cancer that overexpresses a cytokine receptor, e.g., CRLF2, EGFR or IL-7R-α, or a mutated form of CRLF2 or IL-7R-α, EGF, Flt ligand receptor, CD117, the receptor for stem cell factor or another receptor that provides a signal required for cancer cell survival.

In some embodiments, the cancer is a cancer that overexpresses CRLF2 and a patient having the cancer is treated with an effective amount of TSLP or a mimetic of TSLP. In some embodiments, the TSLP is human TSLP or a mimetic of human TSLP. In some embodiments, the cancer is a cancer that overexpresses EGFR and a patient having the cancer is treated with an effective amount of EGF or a mimetic of EGF. In some embodiments, the EGF is human EGF or a mimetic of human EGF. In some embodiments, the cancer is a cancer that overexpresses IL-7Rα and a patient having the cancer is treated with an effective amount of IL-7 or a mimetic of IL-7. In some embodiments, the IL-7 is human IL-7 or a mimetic of human IL-7.

In some embodiments, the cancer is a leukemia that expresses or overexpresses CRLF2 (e.g., a wild-type form or a mutated form). In some embodiments, the cancer is an acute lymphoblastic leukemia or acute myelogenous leukemia in which a wild-type or mutated form of CRLF2 is expressed or overexpressed. For example, in some embodiments, the cancer is a B cell acute lymphoblastic leukemia (B-ALL or B-cell type ALL) in which a wild-type or mutated form of CRLF2 is expressed or overexpressed. In some embodiments, the leukemia is Philadelphia chromosome-like (Ph-like) B-cell type ALL in which a wild-type or mutated form of CRLF2 is expressed or overexpressed.

In some embodiments, methods of killing cancer cells are provided. In some embodiments, the cancer cell is a cell from a cancer as described herein (e.g., a leukemia, e.g., ALL or AML). In some embodiments, the cancer cell expresses or overexpresses a cytokine receptor (e.g., CRLF2, EGFR or IL-7R-α) on the surface of the cell. In some embodiments, the cells are primary cells. In some embodiments, the cells are from a transformed cell line.

Reference Values

In one embodiment, the level of expression of a CRLF2 or IL-7Rα polynucleotide (e.g., mRNA) or protein, the level of activity of CRLF2 protein or IL-7Rα protein (e.g., as assessed by the level of binding of CRLF2 to an anti-CRLF2 antibody or the level of binding of IL-7Rα to an anti-IL-7Rα antibody, the level of phosphorylation of STAT5 protein, and/or the level of phosphorylation of ribosomal protein S6 in a sample from a test subject are compared to a reference value in order to determine whether the test subject has cancer. A variety of methods can be used to determine the reference value. In one embodiment, a reference value for a particular biomarker (e.g., CRLF2, STAT5, ribosomal S6, and IL-7Rα) is determined by assessing the level of that particular biomarker in samples from a population of subjects that is known not to have cancer. As a non-limiting example, in one embodiment, the population of subjects (e.g., 10, 20, 50, 100, 200, 500 subjects or more) all are known not to have cancer and all are analyzed for the level of a particular biomarker (e.g., level of expression of CRLF2). In another embodiment, a reference value for a particular biomarker (e.g., level of expression of CRLF2) is determined by assessing the level of that particular biomarker in samples from a population of subjects having a solid tumor or a particular form of leukemia (e.g., B-cell type ALL). As a non-limiting example, in one embodiment, the population of subjects (e.g., 10, 20, 50, 100, 200, 500 subjects or more) all have a cervical or ovarian solid tumor and all are analyzed for the level of a particular biomarker (e.g., level of expression of CRLF2). In some embodiments, the population of subjects is matched to a test subject according to one or more patient characteristics such as age, sex, ethnicity, or other criteria. In some embodiments, the reference value is established using the same type of sample from the population of subjects (e.g., sample comprising blood or histology tissue) as is used for assessing the level of the biomarker in the test subject.

The reference value may be determined using routine methods (e.g., collecting samples from subjects and determining biomarker values). Determination of particular threshold values for identifying a test subject as having cancer, selection of appropriate ranges, categories, types of leukemia, and the like, are within the skill of those in the art guided by this disclosure. It will be understood that standard statistical methods may be employed by the practitioner in making such determinations. See, e.g., Principles of Biostatistics by Marcello Pagano et al. (Brook Cole; 2000); and Fundamentals of Biostatistics by Bernard Rosner (Duxbury Press, 5th Ed, 1999).

In another embodiment, the level of expression of a CRLF2 or IL-7Rα polynucleotide (e.g., mRNA) or protein, the level of activity of CRLF2 protein or IL-7Rα protein (e.g., as assessed by the level of binding of CRLF2 to an anti-CRLF2 antibody or the level of binding of IL-7Rα to and anti-IL-7Rα antibody), the level of phosphorylation of STAT5 protein, and/or the level of phosphorylation of ribosomal S6 in a sample from a test subject are compared to a control sample in order to determine whether the test subject has cancer. In some embodiments, a control sample is a sample from a subject who does not exhibit any clinical symptoms of cancer. In some embodiments, a control sample is a sample from a subject who has been clinically diagnosed as having cancer (e.g., a particular stage of cancer). In some embodiments, a control sample is a sample from a subject who has been clinically diagnosed as having the same stage and/or form of cancer (e.g., B-cell type ALL) as the subject from whom the sample for testing was obtained. In some embodiments, the subject from whom the control sample is obtained is the same age or about the same age as the test subject.

IV. Prognostic Methods

In another aspect, methods of identifying a subject suitable for TSLP treatment or predicting response of a cancer patient to TSLP treatment are provided. In some embodiments, the subject has cancer (e.g., leukemia or solid tumor). In some embodiments, the method comprises detecting a level of CRLF2 protein expression and detecting a level of IL-7Rα expression in a sample from the subject.

In some embodiments, a method for identifying a subject suitable for TSLP treatment comprises:
(a) detecting a level of CRLF2 protein expression on the surface of a cell from a subject,
(b) detecting a level of IL-7Rα protein expression on the surface of a cell from a subject; and
(c) calculating a ratio of CRLF2 to IL-7Rα based on the detected levels of protein expression; whereby the subject is predicted to respond to TSLP treatment if the level of CRLF2 protein expression is greater than the level of IL-7Rα protein expression. In some embodiments, the subject is predicted to respond to TSLP treatment if the ratio of CRLF2 to IL-7Rα is above 2:1 (e.g., 3:1, 4:1, 5:1, 10:1, 20:1, 50:1, 100:1, or more). In some embodiments, the subject has cancer (e.g., leukemia or solid tumor). In some embodiments, the subject has acute lymphoblastic leukemia. In some embodiments, the subject has B-cell type ALL. In some embodiments, the subject has Ph-like B-cell type ALL. In some embodiments, the subject has T-cell type ALL. In some embodiments, the subject has acute myeloid leukemia. In some embodiments, the subject has a solid tumor. In some embodiments, the subject has a solid tumor of the lungs, cervix, or ovaries.

In another embodiment, a method for predicting response of a cancer patient to TSLP treatment comprises:
(a) detecting a level of CRLF2 protein expression on the surface of a cancer cell from the cancer patient,
(b) detecting a level of IL-7Rα protein expression on the surface of a cancer cell from the cancer patient; and
(c) calculating a ratio of CRLF2 to IL-7Rα based on the detected levels of protein expression; whereby the cancer patient is predicted to respond to TSLP treatment if the level of CRLF2 protein expression is greater than the level of IL-7Rα protein expression on the surface of a cancer cell. In some embodiments, the cancer patient is predicted to respond to TSLP treatment if the ratio of CRLF2 to IL-7Rα is above 2:1 (e.g., 3:1, 4:1, 5:1, 10:1, 20:1, 50:1, 100:1, or more). In some embodiments, the cancer patient has leukemia or a solid tumor. In some embodiments, the cancer patient has acute lymphoblastic leukemia. In some embodiments, the cancer patient has B-cell type ALL. In some embodiments, the cancer patient has Ph-like B-cell type ALL. In some embodiments, the cancer patient has T-cell type ALL. In some embodiments, the cancer patient has acute myeloid leukemia. In some embodiments, the cancer patient has a solid tumor. In some embodiments, the cancer patient has a solid tumor of the lungs, cervix, or ovaries.

In some embodiments, the ratio of CRLF2 to IL-7Rα obtained from the subject or cancer patient is compared to a reference value (e.g., a ratio of CRLF2 to IL-7Rα obtained from a subject known not to have cancer). In some embodiments, a subject is identified as being predicted to respond to TSLP treatment if the ratio of CRLF2 to IL-7Rα is increased by at least 10%, at least 20%, at least 30%, at least 40%, at least 50%, at least 60%, at least 70%, at least 80%, at least 90% or more as compared to the reference value. In some embodiments, a subject is identified as being predicted to respond to TSLP treatment if the ratio of CRLF2 to IL-7Rα is increased by at least 2-fold, at least 3-fold, at least 4-fold, at least 5-fold, at least 10-fold, at least 20-fold, or more as compared to the reference value.

In some embodiments, the method further comprises:
(a) detecting a level of STAT5 phosphorylation in the sample from the subject, and/or
(b) detecting a level of ribosomal S6 phosphorylation in the sample from the subject.

In some embodiments, the method further comprises:
(a) detecting a level of STAT5 phosphorylation in the sample from the cancer patient, and/or
(b) detecting a level of ribosomal S6 phosphorylation in the sample from the cancer patient.

In some embodiments, the sample comprises whole blood, serum, plasma, saliva, urine, cerebrospinal fluid, or a tissue sample (e.g., cervical or lung tissue). In some embodiments, the sample is a blood or plasma sample.

In some embodiments, for a subject (e.g., a subject having leukemia) who is identified as being responsive to TSLP treatment, therapeutic interventions are provided. In some embodiments, the therapeutic intervention is a therapeutic intervention described in Section V below. In some embodiments, the therapeutic intervention comprises administering a biologic agent that increases SOCS1, SOCS2, SOCS3, and/or CISH expression in the subject.

V. Therapeutic Methods

In one aspect, methods of treating a subject having a cancer are provided. In some embodiments, the cancer expresses a cytokine receptor (e.g., on the surface of cancer cells). In some embodiments, the method comprises administering to the subject having a cancer that expresses a cytokine receptor a biologic agent in an amount sufficient to increase expression of one or more Suppressor of Cytokine Signaling (SOCS) gene in a cancer cell in the subject. In some embodiments, the SOCS gene is Suppressor of Cytokine Signaling-1 (SOCS-1), Suppressor of Cytokine Signaling-2 (SOCS-2), Suppressor of Cytokine Signaling-3 (SOCS-3), and/or cytokine-inducible SH2-containing protein (CISH). In some embodiments, the SOCS gene is one or both of Suppressor of Cytokine Signaling-1 (SOCS-1) and Suppressor of Cytokine Signaling-3 (SOCS-3).

In another aspect, methods of killing cancer cells are provided. In some embodiments, the cancer cell expresses a cytokine receptor (e.g., on the surface of the cell). In some embodiments, the method comprises contacting the cancer cell with a biologic agent in an amount sufficient to increase expression of one or more Suppressor of Cytokine Signaling (SOCS) genes in the cancer cell. In some embodiments, the SOCS gene is Suppressor of Cytokine Signaling-1 (SOCS-1), Suppressor of Cytokine Signaling-2 (SOCS-2), Suppressor of Cytokine Signaling-3 (SOCS-3), and/or cytokine-inducible SH2-containing protein (CISH). In some embodiments, the SOCS gene is one or both of Suppressor of Cytokine Signaling-1 (SOCS-1) and Suppressor of Cytokine Signaling-3 (SOCS-3). In some embodiments, the methods are performed in vitro. In some embodiments, the methods are performed ex vivo. In some embodiments, the methods are performed in vivo.

In some embodiments, a biologic agent, e.g., as described herein, is administered in an amount sufficient to increase expression of the one or more SOCS genes by at least 20%, at least 30%, at least 40%, at least 50%, at least 60%, at least 70%, at least 80%, at least 90% or more as compared to a reference value (e.g., a reference value that is determined from the level of expression of a cancer cell that is not treated with the biologic agent). In some embodiments, the biologic agent is administered in an amount sufficient to increase expression of the one or more SOCS genes by at least 2-fold, 3-fold, 4-fold, 5-fold, 6-fold, 7-fold, 8-fold, 9-fold, 10-fold or more as compared to the reference value. In some embodiments, the biologic agent is administered in an amount sufficient to increase expression of the one or more SOCS genes by at least 20%, at least 30%, at least 40%, at least 50%, at least 60%, at least 70%, at least 80%, at least 90% or more as compared to the level of expression of the SOCS gene in the cell prior to the onset of treatment. In some embodiments, the biologic agent is administered in an amount sufficient to increase expression of the one or more SOCS genes by at least 2-fold, 3-fold, 4-fold, 5-fold, 6-fold, 7-fold, 8-fold, 9-fold, 10-fold or more as compared to the level of expression of the SOCS gene in the cell(s) prior to the onset of treatment. In some embodiments, the level of expression of the SOCS gene is measured by quantitative PCR, e.g., RT-PCR.

In one aspect, methods for inhibiting cytokine receptor cell signaling in a cancer expressing or overexpressing one or more cytokine receptors is provided. In some embodiments, the cancer expresses a cytokine receptor on the surface of one or more cancer cells of the cancer. In some embodiments, the cancer overexpresses a cytokine receptor on the surface of one or more cancer cells of the cancer. In some embodiments, the cytokine receptor is selected from EGFR, IL-7Rα and CRLF2. In some embodiments, the method comprises administering to the cancer a therapeutically effective amount of a biologic agent. In some embodiments, the biologic agent is TSLP or a mimetic thereof. In some embodiments, the biologic agent is EGF or a mimetic thereof. In some embodiments, the biologic agent is IL-7 or a mimetic thereof. In some embodiments, inhibiting cytokine receptor cell signaling in the cancer expressing or overexpressing the cytokine receptor is measured by detecting a reduction in cell signaling pathway components in one or more cancer cells of the cancer. In some embodiments, the reduction in cell signaling pathway components comprises measuring the level of phosphorylated STAT6 and/or phosphorylated ribosomal S6 in the cancer cells exposed to the effective amount of the biologic agent. In some embodiments, the reduction in cell signaling pathway components comprises a reduction in the level of phosphorylated STAT6 and/or phosphorylated ribosomal S6 of at least 10%, at least 20%, at least 30%, at least 40%, at least 50%, at least 60%, at least 70%, at least 80%, at least 90% or more, as compared to a reference value (e.g., level of phosphorylated STAT6 and/or phosphorylated ribosomal S6 in non-cancerous cells).

In one embodiment, a method for inhibiting CRLF2 cell signaling in a cancer cell expressing or overexpressing CRLF2 is provided. In some embodiments, the cancer cell expresses CRLF2 on the surface of the cancer cells. In some embodiments, the method comprises administering to the cancer cell a therapeutically effective amount of TSLP or TSLP mimetic.

In another embodiment, a method for inhibiting EGFR cell signaling in a cancer cell expressing or overexpressing EGFR is provided. In some embodiments, the cancer cell expresses EGFR on the surface of the cancer cells. In some embodiments, the method comprises administering to the cancer cell a therapeutically effective amount of EGF or EGF mimetic.

In another embodiment, a method for inhibiting IL-7Rα cell signaling in a cancer cell expressing or overexpressing IL-7Rα is provided. In some embodiments, the cancer cell expresses IL-7Rα on the surface of the cancer cells. In some embodiments, the method comprises administering to the cancer cell a therapeutically effective amount of IL-7 or IL-7 mimetic.

In some embodiments, the cancer expressing or overexpressing a cytokine receptor (e.g., a wild-type form or a mutated form) is a leukemia or solid tumor. In some embodiments, the cancer is an acute lymphoblastic leukemia or acute myelogenous leukemia in which a wild-type or mutated form of CRLF2 is expressed or overexpressed. For example, in some embodiments, the cancer is a B cell acute lymphoblastic leukemia (B-ALL or B-cell type ALL) in which a wild-type or mutated form of CRLF2 is expressed or overexpressed. In some embodiments, the leukemia is Philadelphia chromosome-like (Ph-like) B-cell type ALL in which a wild-type or mutated form of CRLF2 is expressed or overexpressed. In some embodiments, the cancer is a solid tumor in which a wild-type or mutated form of CRLF2 is expressed or overexpressed.

In some embodiments, the cancer expressing or overexpressing a cytokine receptor (e.g., a wild-type form or a mutated form) is a leukemia or solid tumor. In some embodiments, the cancer is an acute lymphoblastic leukemia or acute myelogenous leukemia in which a wild-type or mutated form of EGFR is expressed or overexpressed. For example, in some embodiments, the cancer is a B cell acute lymphoblastic leukemia (B-ALL or B-cell type ALL) in which a wild-type or mutated form of EGFR is expressed or overexpressed. In some embodiments, the leukemia is Philadelphia chromosome-like (Ph-like) B-cell type ALL in which a wild-type or mutated form of EGFR is expressed or overexpressed. In some embodiments, the cancer is a solid tumor in which a wild-type or mutated form of EGFR is expressed or overexpressed.

In some embodiments, the cancer expressing or overexpressing a cytokine receptor (e.g., a wild-type form or a mutated form) is a leukemia or solid tumor. In some embodiments, the cancer is an acute lymphoblastic leukemia or acute myelogenous leukemia in which a wild-type or mutated form of IL-7Rα is expressed or overexpressed. For example, in some embodiments, the cancer is a B cell acute lymphoblastic leukemia (B-ALL or B-cell type ALL) in which a wild-type or mutated form of IL-7Rα is expressed or overexpressed. In some embodiments, the leukemia is Philadelphia chromosome-like (Ph-like) B-cell type ALL in which a wild-type or mutated form of IL-7Rα is expressed or overexpressed. In some embodiments, the cancer is a solid tumor in which a wild-type or mutated form of IL-7Rα is expressed or overexpressed.

Biologic Agents

In some embodiments, the biologic agent is a cytokine or a cytokine mimetic. In some embodiments, the biologic agent is thymic stromal lymphopoietin (TSLP), epidermal growth factor (EGF), interleukin 7 (IL-7), or a mimetic thereof, stem cell factor (SCF), Flt ligand, or any other cytokine that induces signals required for cancer cell survival. In some embodiments, the biologic agent is human TSLP, human EGF, human IL-7, or a mimetic thereof. In some embodiments, the biologic agent is human TSLP. In some embodiments, the biologic agent is a mimetic of TSLP. In some embodiments, the biologic agent is EGF or a mimetic thereof.

In one embodiment, the biologic agent is human TSLP (hTSLP) (SEQ ID NO:1). The amino acid sequence for human TSLP is represented by NCBI Gene ID: 85480. The complete coding sequence of human TSLP is provided as GenBank BC040592.1, both of which are incorporated herein by reference in their entirety, for all purposes.

In one embodiment, the biologic agent is a TSLP mimetic. In one embodiment, a TSLP mimetic can include a modified, truncated or altered form of human TSLP that retains at least 60%, 70%, 80%, 85%, 90%, 95%, 96%, 97%, 98%, or 99% percent identity to SEQ ID NO:1. In one embodiment, a TSLP mimetic can include a modified, truncated or altered form of human TSLP that retains at least 60%, 70%, 80%, 85%, 90%, 95%, 96%, 97%, 98%, or 99% of the corresponding hTSLP function being measured (e.g., upregulation or downregulation of one or more SOCS genes). In another aspect, a TSLP mimetic can include a protein whose sequence is at least 50% equivalent to that of naturally occurring hTSLP (SEQ ID NO:1), or at least 60% equivalent to that of the naturally occurring hTSLP, or at least 70% equivalent to that of the naturally occurring hTSLP, or at least 80% equivalent to that of the naturally occurring hTSLP, or at least 90% equivalent to that of the naturally occurring hTSLP, or at least 95% equivalent to that of the naturally occurring hTSLP, or at least 97% equivalent to that of the naturally occurring hTSLP, or at least 99% equivalent to that of the naturally occurring hTSLP. In yet another embodiment, the biologic agent is a TSLP mimetic that has at least 60%, 70%, 80%, 85%, 90%, 95%, 96%, 97%, 98%, or 99% homology (i.e., percent identity) to SEQ ID NO:1 and retains at least 60%, 70%, 80%, 85%, 90%, 95%, 96%, 97%, 98%, or 99% of the corresponding hTSLP function being measured (e.g., modulation of one or more SOCS genes, internalization of IL-7R-α, or inhibition of IL-7R-α signaling). In some embodiments, the biologic agent is a TSLP mimetic that has at least 60%, 70%, 80%, 85%, 90%, 95%, 96%, 97%, 98%, or 99% homology (i.e., percent identity) to a naturally occurring TSLP (e.g., hTSLP having the sequence of SEQ ID NO:1) and exhibits at least comparable activity to the naturally occurring TSLP for a function being measured (e.g., modulation of one or more SOCS genes, internalization of IL-7R-α, or inhibition of IL-7R-α signaling).

In one embodiment, the biologic agent is human EGF (hEGF) (SEQ ID NO:2). The amino acid sequence for human EGF is represented by NCBI Gene ID: 1950. The complete coding sequence of human EGF is provided as GenBank BC093731.1, both of which are incorporated herein by reference in their entirety, for all purposes.

In one embodiment, the biologic agent is an EGF mimetic. In one embodiment, an EGF mimetic can include a modified, truncated or altered form of human EGF that retains at least 60%, 70%, 80%, 85%, 90%, 95%, 96%, 97%, 98%, or 99% percent identity to SEQ ID NO:2. In one embodiment, a TSLP mimetic can include a modified, truncated or altered form of human TSLP that retains at least 60%, 70%, 80%, 85%, 90%, 95%, 96%, 97%, 98%, or 99% of the corresponding hEGF function being measured (e.g., upregulation or downregulation of one or more SOCS genes). In another aspect, an EGF mimetic can include a protein whose sequence is at least 50% equivalent to that of naturally occurring hEGF (SEQ ID NO:2), or at least 60% equivalent to that of the naturally occurring hEGF, or at least 70% equivalent to that of the naturally occurring hEGF, or at least 80% equivalent to that of the naturally occurring hEGF, or at least 90% equivalent to that of the naturally occurring hEGF, or at least 95% equivalent to that of the naturally occurring hEGF, or at least 97% equivalent to that of the naturally occurring hEGF, or at least 99% equivalent to that of the naturally occurring hEGF. In yet another embodiment, the biologic agent is an EGF mimetic that has at least 60%, 70%, 80%, 85%, 90%, 95%, 96%, 97%, 98%, or 99% homology to SEQ ID NO:2 (hEGF) and retains at least 60%, 70%, 80%, 85%, 90%, 95%, 96%, 97%, 98%, or 99% of the corresponding hEGF function being measured (e.g., modulation of one or more SOCS genes, internalization of IL-7R-α, or inhibition of IL-7R-α signaling). In some embodiments, the biologic agent is an EGF mimetic that has at least 60%, 70%, 80%, 85%, 90%, 95%, 96%, 97%, 98%, or 99% homology (i.e., percent identity) to a naturally occurring EGF (e.g., hEGF having the sequence of SEQ ID NO:2) and exhibits at least comparable activity to the naturally occurring EGF for a function being measured (e.g., modulation of one or more SOCS genes, internalization of IL-7R-α, or inhibition of IL-7R-α signaling).

In one embodiment, the biologic agent is human IL-7 (hIL-7) (SEQ ID NO:3). The amino acid sequence for human IL-7 is represented by NCBI Gene ID: 3574. The complete coding sequence of human IL-7 is provided as GenBank BC047698.1, both of which are incorporated herein by reference in their entirety, for all purposes.

In one embodiment, the biologic agent is an IL-7 mimetic. In one embodiment, an IL-7 mimetic can include a modified, truncated or altered form of human IL-7 that retains at least 60%, 70%, 80%, 85%, 90%, 95%, 96%, 97%, 98%, or 99% percent identity to SEQ ID NO:3. In one embodiment, an IL-7 mimetic can include a modified, truncated or altered form of human IL-7 that retains at least 60%, 70%, 80%, 85%, 90%, 95%, 96%, 97%, 98%, or 99% of the corresponding hIL-7 function being measured (e.g., upregulation or downregulation of one or more SOCS genes). In another aspect, an IL-7 mimetic can include a protein whose sequence is at least 50% equivalent to that of naturally occurring hIL-7 (SEQ ID NO:3), or at least 60% equivalent to that of the naturally occurring hIL-7, or at least 70% equivalent to that of the naturally occurring hIL-7, or at least 80% equivalent to that of the naturally occurring hIL-7, or at least 90% equivalent to that of the naturally occurring hIL-7, or at least 95% equivalent to that of the naturally occurring hIL-7, or at least 97% equivalent to that of the naturally occurring hIL-7, or at least 99% equivalent to that of the naturally occurring hIL-7. In yet another embodiment, the biologic agent is an IL-7 mimetic that has at least 60%, 70%, 80%, 85%, 90%, 95%, 96%, 97%, 98%, or 99% homology to SEQ ID NO:3 (hIL-7) and retains at least 60%, 70%, 80%, 85%, 90%, 95%, 96%, 97%, 98%, or 99% of the corresponding hIL-7 function being measured (e.g., modulation of one or more SOCS genes, internalization of IL-7R-α, or inhibition of IL-7R-α signaling). In some embodiments, the biologic agent is a TSLP mimetic that has at least 60%, 70%, 80%, 85%, 90%, 95%, 96%, 97%, 98%, or 99% homology (i.e., percent identity) to a naturally occurring IL-7 (e.g., hIL-7 having the sequence of SEQ ID NO:3) and exhibits at least comparable activity to the naturally occurring IL-7 for a function being measured (e.g., modulation of one or more SOCS genes, internalization of IL-7R-α, or inhibition of IL-7R-α signaling).

In some embodiments, the biologic agent is a recombinant protein or peptide (e.g., a recombinant form of a TSLP, EGF, or IL-7 protein or peptide or a mimetic thereof). In some embodiments, the biologic agent is a synthetic protein or peptide (e.g., a synthetic form of a TSLP, EGF, or IL-7 protein or peptide or a mimetic thereof).

Administration of Biologic Agents

In some embodiments, the biologic agent (e.g., TSLP, EGF, IL-7 or a mimetic thereof) can be administered intravenously, intrathecally, intraspinally, intraperitoneally, intramuscularly, intranasally, subcutaneously, orally, topically, and/or by inhalation.

The biologic agent is administered in a manner compatible with the dosage formulation, and in such amount as will be therapeutically effective. The term "therapeutically effective amount" refers to that amount of an agent (e.g., a biologic agent as described herein) being administered that will treat to some extent a disease, disorder, or condition, e.g., relieve one or more of the symptoms of the disease being treated, and/or that amount that will prevent, to some extent, one or more of the symptoms of the disease that the subject being treated has or is at risk of developing. In some embodiments, a daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied depending upon the requirements of the patient, the severity of the condition being treated, and the compound being employed. The size of the dose will also be determined by the existence, nature, and extent of any adverse side-effects that accompany the administration of a particular compound in a particular patient. Determination of the proper dosage for a particular situation is within the skill of the practitioner. Frequently, treatment is initiated with smaller dosages which are less than the optimum dose of the compound. Thereafter, the dosage is increased by small increments until the optimum effect under circumstances is reached. For convenience, the total daily dosage may be divided and administered in portions during the day, if desired.

In some embodiments, the biologic agent is administered in "high" physiological dose. A "high" physiological dose as used herein refers to the amount of biologic agent need to achieve a serum level greater than the physiological range of the biologic agent found in a control sample (e.g., the physiological range of the biologic agent existing in a subject who does not have cancer). In one embodiment, a high physiological dose of the biologic agent refers to the amount of biologic agent needed to achieve a TSLP serum level of at least 30 pg/ml in the subject. In another embodiment, a high physiological dose of the biologic agent refers to the amount of biologic agent needed to achieve a TSLP serum level of at least 30 pg/ml, preferably at least 35 pg/ml, at least 40 mg/ml, at least 45 pg/ml, at least 50 pg/ml, or more in the subject. In some embodiments, the biologic agent is administered in a single dose so as to achieve a TSLP serum level of at least 30 pg/ml in the subject. In another embodiment, the biologic agent is administered in multiple doses, for example over several days or weeks, so as to achieve a TSLP serum level of at least 30 pg/ml in the subject. In yet another embodiment, the biologic agent can be administered on an on-going basis to maintain a TSLP serum level of at least 30 pg/ml in the subject. In another embodiment, the biologic agent can be administered when the TSLP serum level of a subject falls below at least 30 pg/ml. In some embodiments, the amount of biologic agent administered is measured by reference to the resulting TSLP serum level of the subject. In one embodiment, the amount of biologic agent administered is measured by reference to the resulting TSLP serum level of the subject as measured by ELISA.

In another embodiment, a high physiological dose of the biologic agent refers to the amount of biologic agent needed to achieve an EGF serum level of at least 39 pg/ml in the subject. In another embodiment, a high physiological dose of the biologic agent refers to the amount of biologic agent needed to achieve an EGF serum level of at least 39 pg/ml, preferably at least 40 mg/ml, at least 45 pg/ml, at least 50 pg/ml, or more in the subject. In some embodiments, the biologic agent is administered in a single dose so as to achieve an EGF serum level of at least 39 pg/ml in the subject. In another embodiment, the biologic agent is administered in multiple doses, for example over several days or weeks, so as to achieve an EGF serum level of at least 39 pg/ml in the subject. In yet another embodiment, the biologic agent can be administered on an on-going basis to maintain an EGF serum level of at least 39 pg/ml in the subject. In another embodiment, the biologic agent can be administered when the EGF serum level of a subject falls below at least 39 pg/ml. In some embodiments, the amount of biologic agent administered is measured by reference to the resulting EGF serum level of the subject. In one embodiment, the amount of biologic agent administered is measured by reference to the resulting EGF serum level of the subject as measured by ELISA.

In one embodiment, a high physiological dose of the biologic agent refers to the amount of biologic agent needed to achieve an IL-7 serum level of at least 20 pg/ml in the subject. In another embodiment, a high physiological dose of the biologic agent refers to the amount of biologic agent needed to achieve an IL-7 serum level of at least 20 pg/ml, preferably at least 50 pg/ml, at least 100 pg/ml, at least 200 pg/ml, at least 500 pg/ml, or more in the subject. In some embodiments, the biologic agent is administered in a single dose so as to achieve an IL-7 serum level of at least 20 pg/ml in the subject. In another embodiment, the biologic agent is administered in multiple doses, for example over several days or weeks, so as to achieve an IL-7 serum level of at least 20 pg/ml in the subject. In yet another embodiment, the biologic agent can be administered on an on-going basis to maintain an IL-7 serum level of at least 20 pg/ml, preferably at least 50 pg/ml in the subject. In another embodiment, the biologic agent can be administered when the IL-7 serum level of a subject falls below 20 pg/ml. In some embodiments, the amount of biologic agent administered is measured by reference to the resulting IL-7 serum level of the subject. In one embodiment, the amount of biologic agent administered is measured by reference to the resulting IL-7 serum level of the subject as measured by ELISA.

In some embodiments, a high physiological dose of a biologic agent refers to the amount needed to achieve a serum level of the biologic agent (e.g., TSLP, EGF, or IL-7) that is at least as high as the physiological level for that biologic agent in a population of normal, healthy subjects (e.g., subjects known not to have cancer).

In some embodiments, the high physiological level of the biologic agent will vary depending on the biologic agent. For example, as discussed above, the normal physiological levels of TSLP in human plasma serum is at least 20 pg/ml; while the normal physiological levels of EGF in human plasma serum is at least 39 pg/ml. In some embodiments, the biologic agent administered to a human subject or cancer patient to achieve serum levels of the biologic agent, is preferably above the normal human physiological level. In some embodiments, the biologic agent administered to a subject or cancer patient is in excess of normal physiological levels found in eukaryotes. In one embodiment, when the biologic agent is a human biologic agent (e.g., hTSLP or hEGF) the amount of biologic agent administered to the subject can be significantly above (e.g., at least 30%, at least 40%, at least 50%, at least 60%, at least 80%, at least 90%, at least 100%, or greater than) the normal physiological levels discussed herein (e.g., 20 pg/ml and 39 pg/ml, respectively). In another embodiment, when the biologic agent is a recombinant biologic agent (e.g., recombinant EGF or recombinant IL-7) or where the biologic agent is produced from a non-human source (e.g., produced by *E. coli*) the amount of biologic agent administered to the subject may be in excess of at least 10-fold, at least 50-fold, at least 100-fold, at least 150-fold, at least 200-fold, at least 250-fold, or greater than 300-fold of the physiological level of the biologic agent in a control sample (e.g., a sample from a subject known not to have cancer).

In some embodiments, the amount of biologic agent administered to a subject can be determined by an appropriate assay. For example, an appropriate assay can include administering an effective amount of the biologic agent, whereby EGFR cell signaling and/or CRLF2 cell signaling pathway is inhibited. In some embodiments, the cell signaling pathway (e.g., EGFR or CRLF2 cell signaling) is inhibited by at least 10%, at least 20%, at least 30%, at least 40%, at least 50%, at least 60%, at least 70%, at least 80%, at least 90%, at least 95%, at least 100%, at least 150%, at least 200%, or more, as compared to cell signaling in a control sample in the absence of the biologic agent. In some embodiments, the biologic agent is administered in an amount that results in IL-7Rα internalization and/or IL-7Rα cell signaling inhibition. Appropriate assays to monitor CRLF2 and IL-7Rα cell signaling includes detecting a level of CRLF2 expression on the surface of a cancer cell from a cancer patient, detecting a level of IL-7Rα expression on the surface of a cancer cell from a subject, and calculating a ratio of CRLF2 to IL-7Rα based on the detected levels of expression, where the cancer patient is predicted to respond to the biologic agent if the level of CRLF2 is higher than the level of IL-7Rα and/or the ratio of CRLF2 to IL-7Rα is above 2:1.

In some embodiments, loss of CRLF2 cell signaling can be determined by detecting a level of phosphorylation for STAT5 and/or a level of phosphorylation for ribosomal protein S6 in a sample (e.g., a cancer cell) and detecting a level of phosphorylation for STAT5 and/or a level of phosphorylation for ribosomal S6 in an untreated or non-cancerous sample.

In some embodiments, the biologic agent is administered on the basis of disease status or disease progression. Disease progression as used herein, refers to the time, generally measured in weeks, or months, from the time of initial treatment until a later time point, such as when the disease worsens or improves. Disease status as used herein, refers to a patients clinical diagnosis, such as remission, re-lapse or cure. In one embodiment, the biologic agent is administered to a subject in need thereof until the subject is determined to be in remission or cured. In one aspect, disease progression can be measured by determining the number or presence of cancerous cells in a sample obtained from the subject. For example, a blood sample from a leukemia patient can be analyzed to determine CRLF2 overexpression. In another embodiment, a blood sample from a leukemia patient can be evaluated for the presence of leukemia cells by detecting expression of one or more cytokine receptors (e.g., IL-7Rα or CRLF2) using flow cytometry.

Combination Therapy

In some embodiments, a biologic agent as described herein (e.g., a cytokine or cytokine mimetic) is administered in combination with one or more additional therapies. In some embodiments, a biologic agent is administered in combination therapy with one or more chemotherapeutic agents. In some embodiments, a biologic agent is administered in combination therapy with one or more demethylation agents. In some embodiments, a biologic agent is administered in combination therapy with one or more chemotherapeutic agents and one or more demethylation agents, one or more radiation therapies, or immunotherapies. In some embodiments, a biologic agent is described herein is administered in combination with radiation therapy.

In some embodiments, a biologic agent as described herein (e.g., a cytokine or cytokine mimetic) is administered in combination with a chemotherapeutic agent. In some embodiments, the chemotherapeutic agent is an alkylating agent (e.g., cyclophosphamide, ifosfamide, chlorambucil, busulfan, melphalan, mechlorethamine, uramustine, thiotepa, nitrosoureas, or temozolomide), an anthracycline (e.g., doxorubicin, adriamycin, daunorubicin, epirubicin, or mitoxantrone), a cytoskeletal disruptor (e.g., paclitaxel or docetaxel), a histone deacetylase inhibitor (e.g., vorinostat or romidepsin), an inhibitor of topoisomerase (e.g., irinotecan, topotecan, amsacrine, etoposide, or teniposide), a kinase inhibitor (e.g., bortezomib, erlotinib, gefitinib, imatinib, vemurafenib, or vismodegib), a nucleoside analog or precursor analog (e.g., azacitidine, azathioprine, capecitabine, cytarabine, fluorouracil, gemcitabine, hydroxyurea, mercaptopurine, methotrexate, or thioguanine), a peptide antibiotic (e.g., actinomycin or bleomycin), a platinum-based agent (e.g., cisplatin, oxaloplatin, or carboplatin), or a plant alkaloid (e.g., vincristine, vinblastine, vinorelbine, vindesine, podophyllotoxin, paclitaxel, or docetaxel).

In some embodiments, a biologic agent as described herein (e.g., a cytokine or cytokine mimetic) is administered in combination with a demethylation agent. Without being bound to a particular theory, it is believed that in certain cancers, methylation of SOCS genes prevents their expression. Thus, administration of a demethylation agent in combination with a biological agent can reverse the shutdown of SOCS gene expression and allow induction of SOCS gene expression by a biologic agent as described herein. In some embodiments, the demethylation agent is a cytidine analog (e.g., azacitidine or decitabine).

Co-administered therapies or therapeutic agents (e.g., a biologic agent as described herein, such as a cytokine or cytokine mimetic, and a second therapy, e.g, a second agent as described herein, such as a chemotherapeutic agent and/or a demethylation agent) can be administered together or separately, simultaneously or at different times. When administered, the therapies or therapeutic agents independently can be administered once, twice, three, four times daily or more or less often, as needed. In some embodiments, the therapies or therapeutic agents are administered once daily. In some embodiments, the therapies or therapeutic agents are administered at the same time or times, for instance as an admixture. In some embodiments, one or more of the therapeutic agents is administered in a sustained-release formulation.

In some embodiments, the biologic agent, e.g., a cytokine or cytokine mimetic, and a second therapy or therapeutic agent, e.g., radiation therapy or a chemotherapeutic agent and/or a demethylation agent, are administered concurrently. In some embodiments, the biologic agent is administered first, for example for about 1, 2, 3, 4, 5, 6, 7, 8, 9, 10, 15, 20, 25, 30, 40, 50, 60, 70, 80, 90, 100 days or more prior to administering the second therapy or therapeutic agent (e.g., chemotherapeutic agent or demethylation agent). In some embodiments, the second therapy or therapeutic agent (e.g., radiation therapy or a chemotherapeutic agent or demethylation agent) is administered first, for example for about 1, 2, 3, 4, 5, 6, 7, 8, 9, 10, 15, 20, 25, 30, 40, 50, 60, 70, 80, 90, 100 days or more prior to administering the biologic agent.

In some embodiments, the biologic agent, e.g., a cytokine or cytokine mimetic, and a second therapy or therapeutic agent, e.g., radiation therapy or a chemotherapeutic agent and/or a demethylation agent, are administered to the subject over an extended period of time, e.g., for at least 30, 40, 50, 60, 70, 80, 90, 100, 150, 200, 250, 300, 350 days or longer.

VI. Pharmaceutical Compositions and Kits

In another aspect, compositions and kits for use in killing cancer cells or treating a cancer (e.g., a cancer that expresses a cytokine receptor) are provided. In some embodiments, the compositions and kits provided herein are for use in killing cancer cells or treating a cancer expresses or overexpresses a cytokine receptor selected from cytokine receptor-like factor 2 (CRLF2), epidermal growth factor receptor (EGFR) or interleukin-7 receptor-α (IL-7R-α). In some embodiments, the compositions and kits provided herein are for use in killing cancer cells or treating a cancer as described in Section V above. In some embodiments, the cancer is a leukemia, e.g., lymphoblastic leukemia (ALL) such as B cell acute lymphoblastic leukemia or Ph-like B-cell type ALL, or acute myelogenous leukemia (e.g., a leukemia that expresses or overexpresses CRLF2, IL-7Rα or EGFR).

Pharmaceutical Compositions

In some embodiments, pharmaceutical compositions are provided that comprise a biologic agent in an amount sufficient to increase expression of one or more SOCS genes (e.g., a SOCS-1 gene and/or a SOCS-3 gene) in a cancer cell, and a pharmaceutically acceptable carrier. In some embodiments, the biologic agent is a cytokine or cytokine mimetic, e.g., as described in Section V above. In some embodiments, the biologic agent is thymic stromal lymphopoietin (TSLP) or a mimetic thereof (e.g., human TSLP or a mimetic thereof). In some embodiments, the biologic agent is interleukin 7 (IL-7) or a mimetic thereof (e.g., human IL-7 or a mimetic thereof). In some embodiments, the biologic agent is epidermal growth factor (EGF) or a mimetic thereof (e.g., human EGF or a mimetic thereof).

In some embodiments, the pharmaceutical composition further comprises one or more additional agents, e.g., one or more therapeutic agents as described in Section V above. In some embodiments, the pharmaceutical composition comprises a biologic agent as described herein and further comprises a chemotherapeutic agent and/or a demethylation agent.

In some embodiments, the pharmaceutical composition comprises human thymic stromal lymphopoietin (TSLP) or a mimetic thereof and further comprises a chemotherapeutic agent, e.g., an alkylating agent (such as, cyclophosphamide, ifosfamide, chlorambucil, busulfan, melphalan, mechlorethamine, uramustine, thiotepa, nitrosoureas, or temozolomide), an anthracycline (such as, doxorubicin, adriamycin, daunorubicin, epirubicin, or mitoxantrone), a cytoskeletal disruptor (such as, paclitaxel or docetaxel), a histone deacetylase inhibitor (such as, vorinostat or romidepsin), an inhibitor of topoisomerase (such as, irinotecan, topotecan, amsacrine, etoposide, or teniposide), a kinase inhibitor (such as, bortezomib, erlotinib, gefitinib, imatinib, vemurafenib, or vismodegib), a nucleoside analog or precursor analog (such as, azacitidine, azathioprine, capecitabine, cytarabine, fluorouracil, gemcitabine, hydroxyurea, mercaptopurine, methotrexate, or thioguanine), a peptide antibiotic (such as, actinomycin or bleomycin), a platinum-based agent (such as cisplatin, oxaloplatin, or carboplatin), or a plant alkaloid (such as, vincristine, vinblastine, vinorelbine, vindesine, podophyllotoxin, paclitaxel, or docetaxel).

In some embodiments, the pharmaceutical composition comprises human thymic stromal lymphopoietin (TSLP) or a mimetic thereof and further comprises a demethylation agent, e.g., a cytidine analog (such as azacitidine or decitabine).

In some embodiments, the pharmaceutical composition comprises human IL-7 or a mimetic thereof and further comprises a chemotherapeutic agent, e.g., an alkylating agent (such as, cyclophosphamide, ifosfamide, chlorambucil, busulfan, melphalan, mechlorethamine, uramustine, thiotepa, nitrosoureas, or temozolomide), an anthracycline (such as, doxorubicin, adriamycin, daunorubicin, epirubicin, or mitoxantrone), a cytoskeletal disruptor (such as, paclitaxel or docetaxel), a histone deacetylase inhibitor (such as, vorinostat or romidepsin), an inhibitor of topoisomerase (such as, irinotecan, topotecan, amsacrine, etoposide, or teniposide), a kinase inhibitor (such as, bortezomib, erlotinib, gefitinib, imatinib, vemurafenib, or vismodegib), a nucleoside analog or precursor analog (such as, azacitidine, azathioprine, capecitabine, cytarabine, fluorouracil, gemcitabine, hydroxyurea, mercaptopurine, methotrexate, or thioguanine), a peptide antibiotic (such as, actinomycin or bleomycin), a platinum-based agent (such as cisplatin, oxaloplatin, or carboplatin), or a plant alkaloid (such as, vincristine, vinblastine, vinorelbine, vindesine, podophyllotoxin, paclitaxel, or docetaxel).

In some embodiments, the pharmaceutical composition comprises human IL-7 or a mimetic thereof and further comprises a demethylation agent, e.g., a cytidine analog (such as azacitidine or decitabine).

In some embodiments, the pharmaceutical composition comprises epidermal growth factor (EGF) or a mimetic thereof and further comprises a chemotherapeutic agent, e.g., an alkylating agent (such as, cyclophosphamide, ifosfamide, chlorambucil, busulfan, melphalan, mechlorethamine, uramustine, thiotepa, nitrosoureas, or temozolomide), an anthracycline (such as, doxorubicin, adriamycin, daunorubicin, epirubicin, or mitoxantrone), a cytoskeletal disruptor (such as, paclitaxel or docetaxel), a histone deacetylase inhibitor (such as, vorinostat or romidepsin), an inhibitor of topoisomerase (such as, irinotecan, topotecan, amsacrine, etoposide, or teniposide), a kinase inhibitor (such as, bortezomib, erlotinib, gefitinib, imatinib, vemurafenib, or vismodegib), a nucleoside analog or precursor analog (such as, azacitidine, azathioprine, capecitabine, cytarabine, fluorouracil, gemcitabine, hydroxyurea, mercaptopurine, methotrexate, or thioguanine), a peptide antibiotic (such as, actinomycin or bleomycin), a platinum-based agent (such as cisplatin, oxaloplatin, or carboplatin), or a plant alkaloid (such as, vincristine, vinblastine, vinorelbine, vindesine, podophyllotoxin, paclitaxel, or docetaxel).

In some embodiments, the pharmaceutical composition comprises epidermal growth factor (EGF) or a mimetic thereof and further comprises a demethylation agent, e.g., a cytidine analog (such as azacitidine or decitabine).

In some embodiments, the pharmaceutical composition comprises a biologic agent as described herein (e.g., TSLP, EGF, IL-7, or a mimetic thereof) in an amount sufficient to increase expression of the one or more SOCS genes (e.g., in a subject or in a cell sample) by at least 20%, at least 30%, at least 40%, at least 50%, at least 60%, at least 70%, at least 80%, at least 90% or more, or by at least 2-fold, 3-fold, 4-fold, 5-fold, 6-fold, 7-fold, 8-fold, 9-fold, 10-fold or more as compared to a reference value.

In some embodiments, the pharmaceutical composition comprises a biologic agent as described herein (e.g., TSLP, EGF, IL-7, or a mimetic thereof) in an amount sufficient to increase internalization of IL-7R-α (e.g., in a subject or in a cell sample) by at least 20%, at least 30%, at least 40%, at least 50%, at least 60%, at least 70%, at least 80%, at least 90% or more, or by at least 2-fold, 3-fold, 4-fold, 5-fold, 6-fold, 7-fold, 8-fold, 9-fold, 10-fold or more as compared to a reference value.

In some embodiments, the pharmaceutical composition comprises a biologic agent as described herein (e.g., TSLP, EGF, IL-7, or a mimetic thereof) in an amount sufficient to decrease downstream IL-7R-α signaling (e.g., in a subject or in a cell sample) by at least 20%, at least 30%, at least 40%, at least 50%, at least 60%, at least 70%, at least 80%, at least 90% or more, or by at least 2-fold, 3-fold, 4-fold, 5-fold, 6-fold, 7-fold, 8-fold, 9-fold, 10-fold or more as compared to a reference value. In some embodiments, the downstream IL-7R-α signaling is STAT5 phosphorylation. In some embodiments, the downstream IL-7R-α signaling is S6 phosphorylation.

In some embodiments, a biologic agent as described herein and optionally one or more additional therapeutic agent (e.g., a chemotherapeutic agent and/or a demethylation agent) is formulated into a pharmaceutical composition by formulation with appropriate pharmaceutically acceptable carriers or diluents, and can be formulated into preparations in solid, semi-solid, liquid or gaseous forms, such as tablets, capsules, pills, powders, granules, dragees, gels, slurries, ointments, solutions, suppositories, injections, inhalants and aerosols.

Guidance for preparing formulations for use in the present disclosure is found in, for example, in *Remington: The Science and Practice of Pharmacy*, 21' Ed., 2006, supra; *Martindale: The Complete Drug Reference*, Sweetman, 2005, London: Pharmaceutical Press; Niazi, *Handbook of Pharmaceutical Manufacturing Formulations,* 2004, CRC Press; and Gibson, *Pharmaceutical Preformulation and Formulation: A Practical Guide from Candidate Drug Selection to Commercial Dosage Form,* 2001, Interpharm Press, which are hereby incorporated herein by reference. The pharmaceutical compositions described herein can be manufactured in a manner that is known to those of skill in the art, i.e., by means of conventional mixing, dissolving, granulating, dragee-making, levigating, emulsifying, encapsulating, entrapping or lyophilizing processes. The following methods and excipients are merely exemplary and are in no way limiting.

In some embodiments, a pharmaceutical composition comprises an acceptable carrier and/or excipients. A pharmaceutically acceptable carrier includes any solvents, dispersion media, or coatings that are physiologically compatible and that preferably does not interfere with or otherwise inhibit the activity of the therapeutic agent. In some embodiments, the carrier is suitable for intravenous, intramuscular, oral, intraperitoneal, transdermal, topical, or subcutaneous administration. Pharmaceutically acceptable carriers can contain one or more physiologically acceptable compound(s) that act, for example, to stabilize the composition or to increase or decrease the absorption of the active agent(s). Physiologically acceptable compounds can include, for example, carbohydrates, such as glucose, sucrose, or dextrans, antioxidants, such as ascorbic acid or glutathione, chelating agents, low molecular weight proteins, compositions that reduce the clearance or hydrolysis of the active agents, or excipients or other stabilizers and/or buffers. Other pharmaceutically acceptable carriers and their formulations are well-known and generally described in, for example, *Remington: The Science and Practice of Pharmacy*, 21st Edition, Philadelphia, PA Lippincott Williams & Wilkins, 2005. Various pharmaceutically acceptable excipients are well-known in the art and can be found in, for example, Handbook of Pharmaceutical Excipients ($5^{th}$ ed., Ed. Rowe et al., Pharmaceutical Press, Washington, D.C.).

In some embodiments, a biologic agent as described herein (and optionally one or more additional therapeutic agents, e.g., a chemotherapeutic agent and/or a demethylation agent) is formulated for oral administration by combining with pharmaceutically acceptable carriers that are well known in the art. Such carriers enable the agents to be formulated as tablets, pills, dragees, capsules, emulsions, lipophilic and hydrophilic suspensions, liquids, gels, syrups, slurries, suspensions and the like, for oral ingestion by a patient to be treated. Pharmaceutical preparations for oral use can be obtained by mixing the agents with a solid excipient, optionally grinding a resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents can be added, such as a cross-linked polyvinyl pyrrolidone, agar, or alginic acid or a salt thereof such as sodium alginate.

In some embodiments, a biologic agent as described herein (and optionally one or more additional therapeutic agents, e.g., a chemotherapeutic agent and/or a demethylation agent) is formulated for parenteral administration by injection, e.g., by bolus injection or continuous infusion. For injection, the agent or agents can be formulated into preparations by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. In some embodiments, agents can be formulated in aqueous solutions, preferably in physiologically compatible buffers such as Hanks's solution, Ringer's solution, or physiological saline buffer. Formulations for injection can be presented in unit dosage form, e.g., in ampules or in multi-dose containers, with an added preservative. The compositions can take such forms as suspensions, solutions or emulsions in oily or aqueous vehicles, and can contain agents such as suspending, stabilizing and/or dispersing agents.

In some embodiments, a biologic agent as described herein (and optionally one or more additional therapeutic agents, e.g., a chemotherapeutic agent and/or a demethylation agent) is prepared for delivery in a sustained-release, controlled release, extended-release, timed-release or delayed-release formulation, for example, in semi-permeable matrices of solid hydrophobic polymers containing the therapeutic agent. Various types of sustained-release materials have been established and are well known by those skilled in the art. Sustained-release delivery systems can, depending on their design, release the agents over the course of hours or days, for instance, over 4, 6, 8, 10, 12, 16, 20, 24 hours or more. Usually, sustained release formulations can be prepared using naturally-occurring or synthetic polymers, for instance, polymeric vinyl pyrrolidones, such as polyvinyl pyrrolidone (PVP); carboxyvinyl hydrophilic polymers; hydrophobic and/or hydrophilic hydrocolloids, such as methylcellulose, ethylcellulose, hydroxypropylcellulose, and hydroxypropylmethylcellulose; and carboxypolymethylene.

Therapeutic Kits

In some embodiments, kits for use in killing cancer cells or treating a cancer (e.g., a cancer that expresses a cytokine receptor) are provided. In some embodiments, the kit comprises:
  a biologic agent in an amount sufficient to increase expression of one or more SOCS genes (e.g., a SOCS-1 gene and/or a SOCS-3 gene) in a cancer cell; and
  one or more additional agents.

In some embodiments, the biologic agent is a cytokine or cytokine mimetic, e.g., as described in Section III above. In some embodiments, the biologic agent is thymic stromal lymphopoietin (TSLP) or a mimetic thereof (e.g., human TSLP or a mimetic thereof). In some embodiments, the biologic agent is interleukin 7 (IL-7) or a mimetic thereof (e.g., human IL-7 or a mimetic thereof). In some embodiments, the biologic agent is epidermal growth factor (EGF) or a mimetic thereof (e.g., human EGF or a mimetic thereof).

In some embodiments, the one or more additional agents are one or more therapeutic agents, e.g., as described in Section III above. In some embodiments, the kit comprises a biologic agent as described herein and further comprises a chemotherapeutic agent and/or a demethylation agent.

In some embodiments, the kit comprises human thymic stromal lymphopoietin (TSLP) or a mimetic thereof and further comprises a chemotherapeutic agent, e.g., an alkylating agent (such as, cyclophosphamide, ifosfamide, chlorambucil, busulfan, melphalan, mechlorethamine, uramustine, thiotepa, nitrosoureas, or temozolomide), an anthracycline (such as, doxorubicin, adriamycin, daunorubicin, epirubicin, or mitoxantrone), a cytoskeletal disruptor (such as, paclitaxel or docetaxel), a histone deacetylase inhibitor (such as, vorinostat or romidepsin), an inhibitor of topoisomerase (such as, irinotecan, topotecan, amsacrine, etoposide, or teniposide), a kinase inhibitor (such as, bortezomib, erlotinib, gefitinib, imatinib, vemurafenib, or vismodegib), a nucleoside analog or precursor analog (such as, azacitidine, azathioprine, capecitabine, cytarabine, fluorouracil, gemcitabine, hydroxyurea, mercaptopurine, methotrexate, or thioguanine), a peptide antibiotic (such as, actinomycin or bleomycin), a platinum-based agent (such as cisplatin, oxaloplatin, or carboplatin), or a plant alkaloid (such as, vincristine, vinblastine, vinorelbine, vindesine, podophyllotoxin, paclitaxel, or docetaxel).

In some embodiments, the kit comprises human thymic stromal lymphopoietin (TSLP) or a mimetic thereof and further comprises a demethylation agent, e.g., a cytidine analog (such as azacitidine or decitabine).

In some embodiments, the kit comprises human IL-7 or a mimetic thereof and further comprises a chemotherapeutic agent, e.g., an alkylating agent (such as, cyclophosphamide, ifosfamide, chlorambucil, busulfan, melphalan, mechlorethamine, uramustine, thiotepa, nitrosoureas, or temozolomide), an anthracycline (such as, doxorubicin, adriamycin, daunorubicin, epirubicin, or mitoxantrone), a cytoskeletal disruptor (such as, paclitaxel or docetaxel), a histone deacetylase inhibitor (such as, vorinostat or romidepsin), an inhibitor of topoisomerase (such as, irinotecan, topotecan, amsacrine, etoposide, or teniposide), a kinase inhibitor (such as, bortezomib, erlotinib, gefitinib, imatinib, vemurafenib, or vismodegib), a nucleoside analog or precursor analog (such as, azacitidine, azathioprine, capecitabine, cytarabine, fluorouracil, gemcitabine, hydroxyurea, mercaptopurine, methotrexate, or thioguanine), a peptide antibiotic (such as, actinomycin or bleomycin), a platinum-based agent (such as cisplatin, oxaloplatin, or carboplatin), or a plant alkaloid (such as, vincristine, vinblastine, vinorelbine, vindesine, podophyllotoxin, paclitaxel, or docetaxel).

In some embodiments, the kit comprises human IL-7 or a mimetic thereof and further comprises a demethylation agent, e.g., a cytidine analog (such as azacitidine or decitabine).

In some embodiments, the kit comprises human epidermal growth factor or a mimetic thereof and further comprises a chemotherapeutic agent, e.g., an alkylating agent (such as, cyclophosphamide, ifosfamide, chlorambucil, busulfan, melphalan, mechlorethamine, uramustine, thiotepa, nitrosoureas, or temozolomide), an anthracycline (such as, doxorubicin, adriamycin, daunorubicin, epirubicin, or mitoxantrone), a cytoskeletal disruptor (such as, paclitaxel or docetaxel), a histone deacetylase inhibitor (such as, vorinostat or romidepsin), an inhibitor of topoisomerase (such as, irinotecan, topotecan, amsacrine, etoposide, or teniposide), a kinase inhibitor (such as, bortezomib, erlotinib, gefitinib, imatinib, vemurafenib, or vismodegib), a nucleoside analog or precursor analog (such as, azacitidine, azathioprine, capecitabine, cytarabine, fluorouracil, gemcitabine, hydroxyurea, mercaptopurine, methotrexate, or thioguanine), a peptide antibiotic (such as, actinomycin or bleomycin), a platinum-based agent (such as cisplatin, oxaloplatin, or carboplatin), or a plant alkaloid (such as, vincristine, vinblastine, vinorelbine, vindesine, podophyllotoxin, paclitaxel, or docetaxel).

In some embodiments, the kit comprises human EGF or a mimetic thereof and further comprises a demethylation agent, e.g., a cytidine analog (such as azacitidine or decitabine).

Diagnostic Kits

In another aspect, kits for use in diagnosing cancers that express or overexpress a cytokine receptor are provided. In some embodiments, the kit comprises an antibody that is immunologically specific for the cytokine receptor expressed or overexpressed by the cancer (e.g., anti-CRLF2 antibody, anti-IL-7Rα antibody or anti-EGFR antibody); and one or more additional reagents.

In some embodiments, the kit comprises an antibody immunologically specific for the overexpression of CRLF2 (e.g., an anti-CRLF2antibody). In some embodiments, the kit comprises an antibody immunologically specific for the overexpression of EGFR (e.g., an anti-EGFR antibody). In some embodiments, the kit comprises an antibody immunologically specific for the overexpression of IL-7Rα (e.g., an anti-IL-7Rα antibody).

Specific immunological binding of an antibody to a cytokine receptor can be detected directly or indirectly (for example, attaching a label to the antibody). Direct labels include fluorescent or luminescent tags, metals, dyes, radionuclides, and the like, attached to the antibody. For example, an antibody labeled with iodine-125 ($^{125}$I) can be used. A chemiluminescence assay using a chemiluminescent antibody specific for the cytokine receptor is suitable for sensitive, non-radioactive detection of cytokine receptor levels. An antibody labeled with fluorochrome is also suitable. Examples of fluorochromes include, without limitation, DAPI, fluorescein, Hoechst 33258, R-phycocyanin, B-phycoerythrin, R-phycoerythrin, rhodamine, Texas red, and lissamine. Indirect labels include various enzymes well known in the art, such as horseradish peroxidase (HRP), alkaline phosphatase (AP), β-galactosidase, urease, and the like. A horseradish-peroxidase detection system can be used, for example, with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, for example, which yields a soluble product readily detectable at 405 nm. Similarly, a β-galactosidase detection system can be used with the chromogenic substrate o-nitrophenyl-β-D-galactopyranoside (ONPG), which yields a soluble product detectable at 410 nm. A urease detection system can be used with a substrate such as urea-bromocresol purple (Sigma Immunochemicals; St. Louis, MO).

In some embodiments, the antibody immunologically specific for detecting overexpression of a cytokine receptor is fluorescently labeled. In some embodiments, the fluorescently labeled antibody is bound or conjugated to a cytokine receptor on a cancer cell and can be detected by flow cytometry. Biotinylated, fluorescently labeled, or other labeled antibodies immunologically specific for cytokine receptors are commercially available (See, e.g., BioLegend, San Diego, CA). In some embodiments, the antibody is a monoclonal antibody. In some embodiments, the antibody is a polyclonal antibody.

In some embodiments, a method of detecting a cancer cell expressing or overexpressing a cytokine receptor comprises contacting the cancer cell with an antibody having immunological specificity for the cytokine receptor and detecting binding of the antibody to the cytokine receptor. In some embodiments, the binding is detected by flow cytometry.

In some embodiments, a method of detecting a cell expressing a cytokine receptor comprises contacting the cell from a cell sample with an antibody having immunological specificity for the cytokine receptor and detecting binding of the antibody to the cytokine receptor. In some embodiments, the method further comprises contacting the cell sample with one or more markers prior to contacting the cell with the antibody having immunological specificity for the cytokine receptor. In some embodiments, the antibody having immunological specificity for the cytokine receptor is an anti-CRLF2 antibody. In some embodiments, the antibody having immunological specificity for the cytokine receptor is an anti-EGFR antibody. In some embodiments, the antibody having immunological specificity for the cytokine receptor is an anti-IL-7Rα antibody. In some embodiments, the one or more markers is selected from the group consisting of CD2, CD3, CD5, CD7, CD10, CD34 and TDT. In some embodiments, where the cell is from B-cell type ALL, the one or more markers is selected from CD10, CD2, CD34 and TDT. In some embodiments, where the cell is from a T-cell, the one or more markers is selected from CD3, CD5, and CD7. In some embodiments, the contacting of the cell to the one or more markers comprises binding the cell to the one or more markers. In some embodiments, the binding is detected by flow cytometry. In some embodiments, the cells bound to the one or more markers are separated from the remainder of the cell sample prior to contacting with the antibody having immunological specificity for the cytokine receptor. In some embodiments, the separated cells bound to the one or more markers are contacted with the antibody having immunological specificity for the cytokine receptor. In some embodiments, binding of the antibody having immunological specificity for the cytokine receptor is detected in one or more of the separated cells from the cell sample.

In some embodiments, the one or more markers can be used in combination with the antibody having immunological specificity for the cytokine receptor to form a kit (e.g., a panel) for detecting cancer cells in the cell sample. In some embodiments, the panel can be used to identify cancer cells in the cell sample by contacting the cell sample with the one or more markers, the antibody having having immunological specificity for the cytokine receptor, detecting binding of the one or more markers to cells in the cell sample, and detecting binding of the antibody to the cytokine receptor in the cells having one or more bound markers. In some embodiments, the one or more markers are contacted with the cell sample and binding of the one or more markers to cells in the cell sample is detected prior to the contacting of the antibody having immunological specificity for the cytokine receptor.

In some embodiments, the one or more additional reagents are enzymes, substrates, cofactors, stabliziers, buffers, washing solutions, staining solutions, and the like, e.g., as described in Section III above. The relative amounts of the various reagents may be varied widely to provide for concentrations in solution of the reagents that substantially optimize the sensitivity of the kit.

In some embodiments, the kits can further comprise instructional materials containing directions (i.e., protocols) for the practice of the methods of this invention (e.g., instructions for using the kit for treating a cancer). While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

VII. Methods of Identifying Therapeutic Compositions

In another aspect, methods of identifying therapeutic agents for the treatment of a cancer as described herein are provided. In some embodiments, the therapeutic agents that are identified can be used for treating a cancer that expresses or overexpresses a cytokine receptor (e.g., CRLF2, EGFR, or IL-7R-α).

Using the assays described herein, one can identify lead compounds that are suitable for further testing to identify those compounds that are therapeutically effective in treating a cancer as described herein. Compounds of interest can be either synthetic or naturally-occurring.

The screening assays described herein can be carried out in vitro, such as by using cell-based assays, or in vivo, such as by using animal models. The screening methods are designed to screen large chemical or polymer libraries comprising, e.g., small organic molecules, peptides, peptidomimetics, peptoids, proteins, polypeptides, glycoproteins, oligosaccharides, or polynucleotides such as inhibitory RNA (e.g., siRNA, antisense RNA), by automating the assay steps and providing compounds from any convenient source to the assays, which are typically run in parallel (e.g., in microtiter formats on microtiter plates in robotic assays). In some embodiments, the screening assays utilize a high-throughput format.

In some embodiments, a method of identifying an agent for the treatment of a cancer comprises:
(a) contacting one or more compounds to a cell or a population of cells;
(b) determining whether the one or more compounds increases the level of expression of one or more SOCS genes in the cell or population of cells, relative to a reference value or to a control sample that has not been contacted with the one or more compounds; and
(c) selecting for the one or more compounds that increases the level of expression of one or more SOCS genes in the cell or population of cells.

In some embodiments, the one or more SOCS genes is Suppressor of Cytokine Signaling-1 (SOCS-1), Suppressor of Cytokine Signaling-2 (SOCS-2), Suppressor of Cytokine Signaling-3 (SOCS-3), and/or cytokine-inducible SH2-containing protein (CISH). In some embodiments, the method comprises determining whether the one or more compounds increases the level of expression of one, two, three, or all four of SOCS-1, SOCS-2, SOCS-3, and CISH.

In some embodiments, the selecting step comprises selecting for the one or more compounds that increase the level of expression of the one or more SOCS genes (e.g., SOCS-1, SOCS-2, SOCS-3, and/or CISH) in the cell or population of cells by at least 10%, at least 20%, at least 30%, at least 40%, at least 50%, at least 60%, at least 70%, at least 80%, at least 90% or more relative to the reference value or control sample. In some embodiments, the selecting step comprises selecting for the one or more compounds that increase the level of expression of one or more SOCS genes (e.g., SOCS-1, SOCS-2, SOCS-3, and/or CISH) in the cell or population of cells by at least 2-fold, at least 3-fold, at least 4-fold, at least 5-fold, at least 6-fold, at least 7-fold, at least 8-fold, at least 9-fold, at least 10-fold or higher relative to the reference value or control sample.

The screening assays described herein may be practiced in any of a number of cell types or cell populations. In some embodiments, the cell or population of cells is a mammalian cell. In some embodiments, the cell or population of cells is a human cell. In some embodiments, the cell or population of cells is a cancer cell, e.g., a leukemia cell or solid tumor. In some embodiments, the cells are primary cells. In some embodiments, the cells are from a transformed cell line.

Essentially any chemical compound can be screened according to the assays described herein. In some embodiments, the compound is one that can be dissolved in aqueous or organic solutions. It will be appreciated that there are many suppliers of chemical compounds, including Sigma (St. Louis, MO), Aldrich (St. Louis, MO), Sigma-Aldrich (St. Louis, MO), Fluka Chemika-Biochemica Analytika (Buchs Switzerland), as well as providers of small organic molecule and peptide libraries ready for screening, including Chembridge Corp. (San Diego, CA), Discovery Partners International (San Diego, CA), Triad Therapeutics (San Diego, CA), Nanosyn (Menlo Park, CA), Affymax (Palo Alto, CA), ComGenex (South San Francisco, CA), Tripos, Inc. (St. Louis, MO); and Selleckchem (Houston, TX).

Representative amino acid compound libraries include, but are not limited to, peptide libraries (see, e.g., U.S. Pat. Nos. 5,010,175; 6,828,422; and 6,844,161; Furka, *Int. J. Pept. Prot. Res.*, 37:487-493 (1991); Houghton et al., *Nature*, 354:84-88 (1991); and Eichler, *Comb Chem High Throughput Screen.*, 8:135 (2005)), peptoids (PCT Publication No. WO 91/19735), encoded peptides (PCT Publication No. WO 93/20242), random bio-oligomers (PCT Publication No. WO 92/00091), vinylogous polypeptides (Hagihara et al., *J. Amer. Chem. Soc.,* 114:6568 (1992)), nonpeptidal peptidomimetics with β-D-glucose scaffolding (Hirschmann et al., *J. Amer. Chem. Soc.*, 114:9217-9218 (1992)), peptide nucleic acid libraries (see, e.g., U.S. Pat. No. 5,539,083), antibody libraries (see, e.g., U.S. Pat. Nos. 6,635,424 and 6,555,310; PCT Application No. PCT/US96/10287; and Vaughn et al., *Nature Biotechnology*, 14:309-314 (1996)), and peptidyl phosphonates (Campbell et al., *J. Org. Chem.*, 59:658 (1994)).

In some embodiments, after candidate compounds are identified by the screening assays described above as, compound optimization is conducted. Typically, optimization involves the use of in vitro and in vivo screens (e.g., in an appropriate animal model, e.g., a mammal such as a mouse, rat, or monkey) to assess the biological, pharmacokinetic, and pharmacodynamic properties of the compounds, such as oral bioavailability, half-life, metabolism, toxicity, pharmacokinetic profile, and pharmacodynamic activity. See, e.g., Guido et al., *Combinatorial Chemistry & High Throughput Screening*, 2011, 14:830-839; and Ghose et al., *ACS Chem Neurosci*, 2012, 3:50-68. In some embodiments, structural analogs of a candidate compound are designed and screened. Methods of designing and screening structural analogs are described in the art. See, e.g., Dimova et al., *Med. Chem. Commun.*, 2016, 7:859-863; and *Analogue-Based Drug Discovery II*, J. Fischer and C. R. Ganellin, eds., Wiley-VCH Verlag GmbH & Co., KGaA, Weinheim, Germany, 2010.

VIII. Examples

The following examples are offered to illustrate, but not to limit, the claimed invention.

Example 1: Development of Patient Derived Xenografts as a Model System to Study hTSLP-Induced Signals in CRLF2-B-ALL The best preclinical models for identifying therapies to effectively treat high risk leukemia are patient-derived xenograft (PDX) models produced by injecting leukemia cells from patients into immune deficient mice (Francis O L, Milford T A, Beldiman C, Payne K J. Fine-tuning patient-derived xenograft models for precision medicine approaches in leukemia. J Investig Med. 2016; 64(3):740-4). Standard PDX models are suboptimal for studies of CRLF2 B-ALL because mouse hTSLP does not activate the human CRLF2 receptor.

Figure 1A:
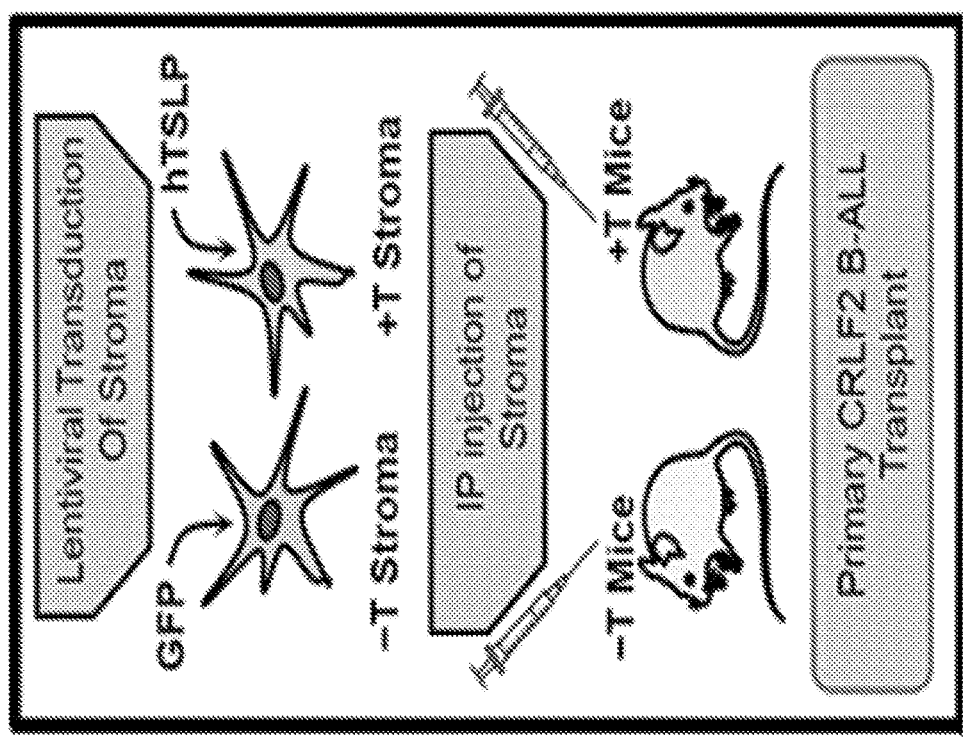
FIGS. 1A-1B. Strategy for generating xenograft mice to express human TSLP. (A) Immune deficient mice were injected with stromal cells transduced to express human TSLP (+T PDX). Control mice (−T PDX) were produced by injecting stroma transduced with a control vector (GFP). Both +T PDX and −T PDX mice were transplanted with normal hematopoietic stem cells or with CRLF2 B-ALL cells. (B) Schematic representation of strategy to prepare a patient derived xenograft.
Figure 1B:
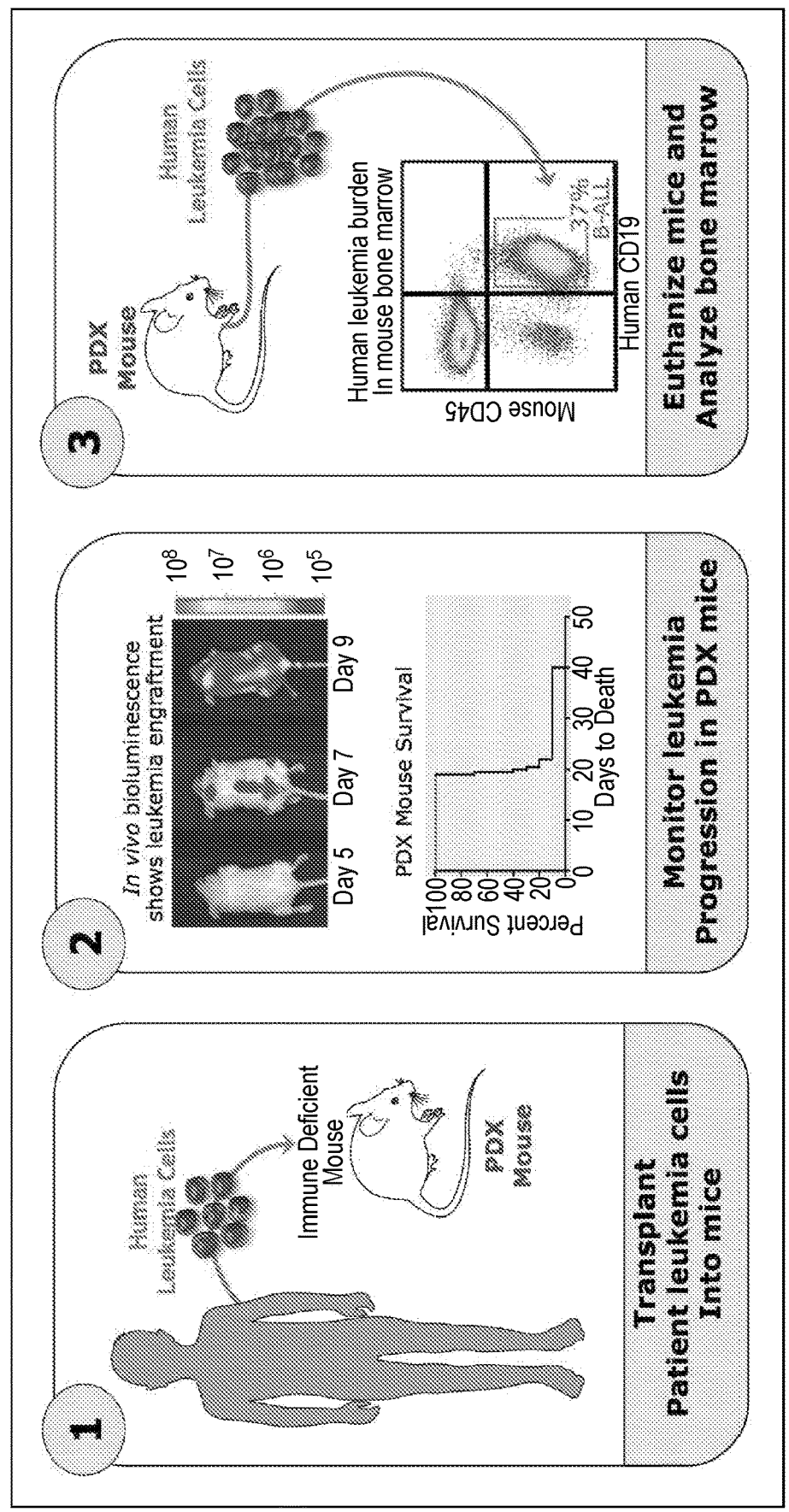
Figure 2A:
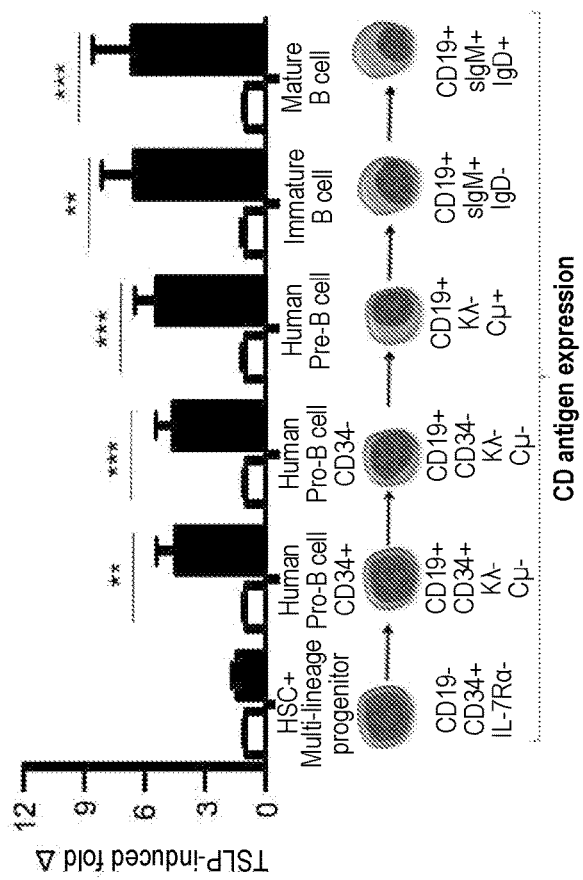
FIG. 2A-2C. TSLP produced in xenograft mice increases number of normal B cell progenitors. (A) Schematic representation of strategy to induce changes in human B cell subsets. (B) Quantitation of number of cells expressing hCD19 in −T PDX mice and +T PDX mice expressing TSLP at low physiological levels (4-10 pg/ml), similar effects were seen at >30 pg/ml (e.g., high physiological level). (C) Quantitation of normal human B cell precursors, data shows a 3-6 fold expansion of normal human B cell precursors in +T as compared to −T mice.
Figure 2B:
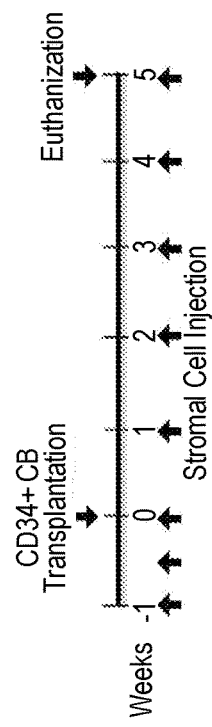
Figure 2C:
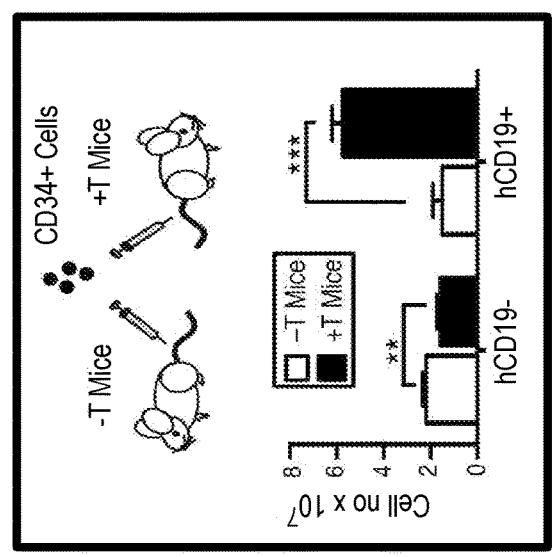

To study hTSLP-induced CRLF2 signals in CRLF2 B-ALL, a PDX model system was developed (FIG. 1A). We engineered PDX mice to produce human hTSLP (+T PDX) by injecting them with stromal cells transduced to express human hTSLP. Control mice (−T PDX) were produced by injecting stroma transduced with a control vector (FIG. 1A). Initially studies achieved low circulating hTSLP levels in +T PDX mice that were detectable (5-10 pg/ml), but at the low end of hTSLP levels reported in normal children (Lee et al., Pediatr. Allergy Immunol., 2010; 21 (2 Pt2): e457-60). Subsequent studies of more than 30 leukemia patients show that this is the normal physiological level in those patients. When transplanted with normal hematopoietic stem cells or with CRLF2 B-ALL cells (FIG. 1B), the +T and −T PDX with TSLP at these low physiological levels showed good engraftment of human cells and in vivo hTSLP functional effects including: (1) production of normal human B cell precursors was expanded 3-6 fold expanded in +T as compared to −T mice (FIG. 2), and (2) CRLF2 B-ALL cells from +T mice showed a gene expression profile significantly more like original patient, as compared to those from −T mice (data not shown).

Example 2: hTSLP as a Biologic for the Treatment of Leukemia

Figure 3:
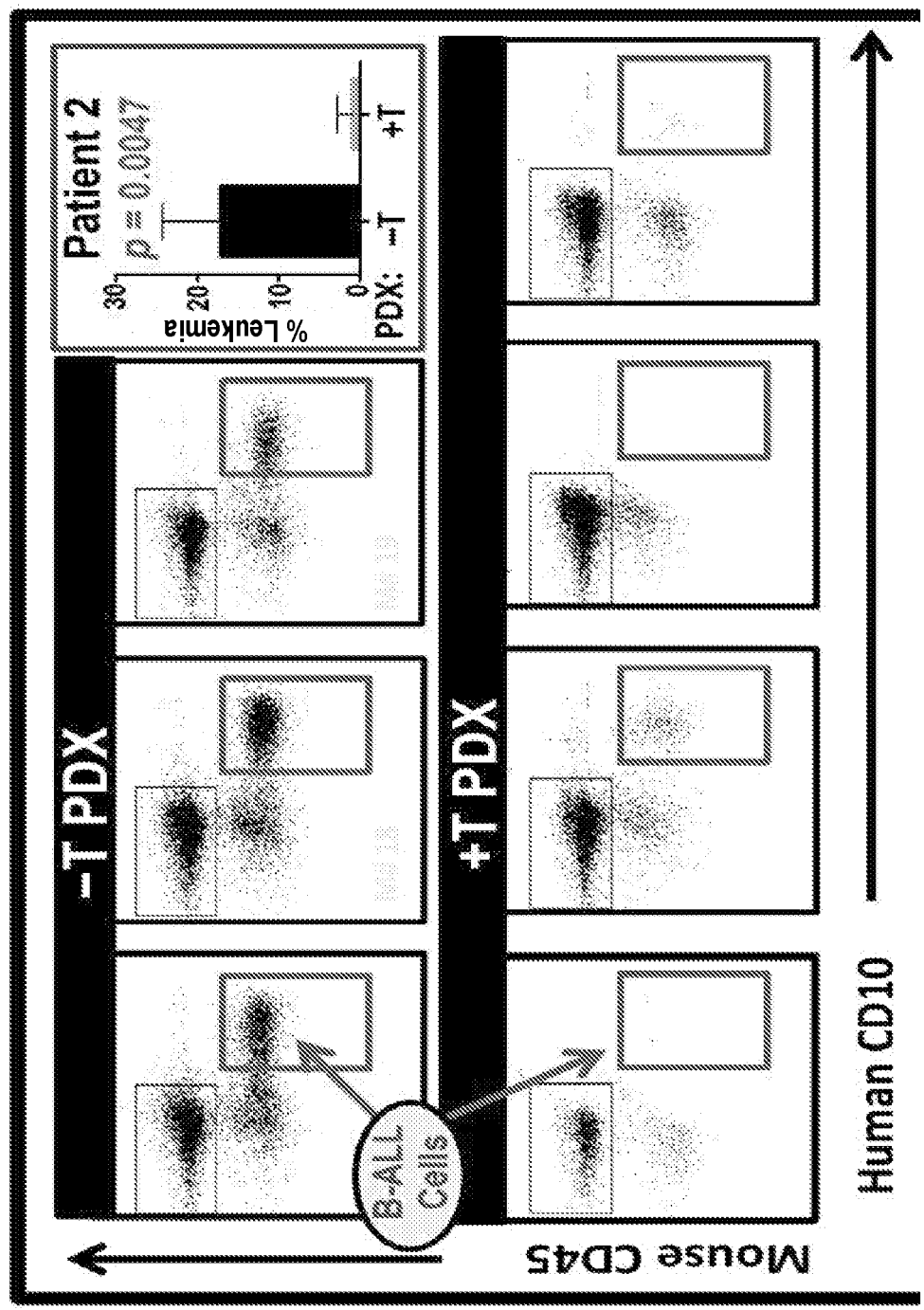
FIG. 3. Anti-leukemia effects of TSLP. PDX was established from a primary Hispanic pediatric patient, essentially as set forth in Example 1. Two weeks later, PDX mice were injected with control stroma or stroma that express hTSLP to produce +T mice with hTSLP serum levels of ~32-93 pg/ml (bottom row) and control −T PDX mice (top row). After 10 weeks, bone marrow (BM) was harvested and stained for flow cytometry to detect human CRLF2 B-ALL cells (gated in red box). Human B-ALL cells were easily detectable by flow cytometry in bone marrow (BM) harvested from −T PDX mice (top row). Leukemia cells were essentially absent from +T PDX (bottom row). Far right, top panel, shows quantitation of the percentage of human leukemia cells in mouse BM. Data are representative of 5 experiments performed on a total of N=20−T PDX and N=20+T PDX generated from 2 different patient samples.

We produced +T mice with hTSLP serum levels of ~32-93 pg/ml. Using these mice we generated +T and −T PDX from a primary Hispanic pediatric patient, expecting an expansion of CRLF2 B-ALL cells in +T mice. Human B-ALL cells were easily detectable by flow cytometry in bone marrow (BM) harvested from −T PDX (FIG. 3) top row. To our surprise, leukemia cells were essentially absent from +T PDX. To exclude the possibility that hTSLP was preventing engraftment of leukemia cells, rather than exerting a therapeutic effect, in our next experiment, stromal cell injection to produce +T or −T PDX was not initiated until 2 weeks after leukemia cell transplant. The results from the initial experiment were confirmed, CRLF2 B-ALL was essentially cured (FIG. 3) by circulating hTSLP at elevated physiological levels.

Figures 4A, 4B, 4C:
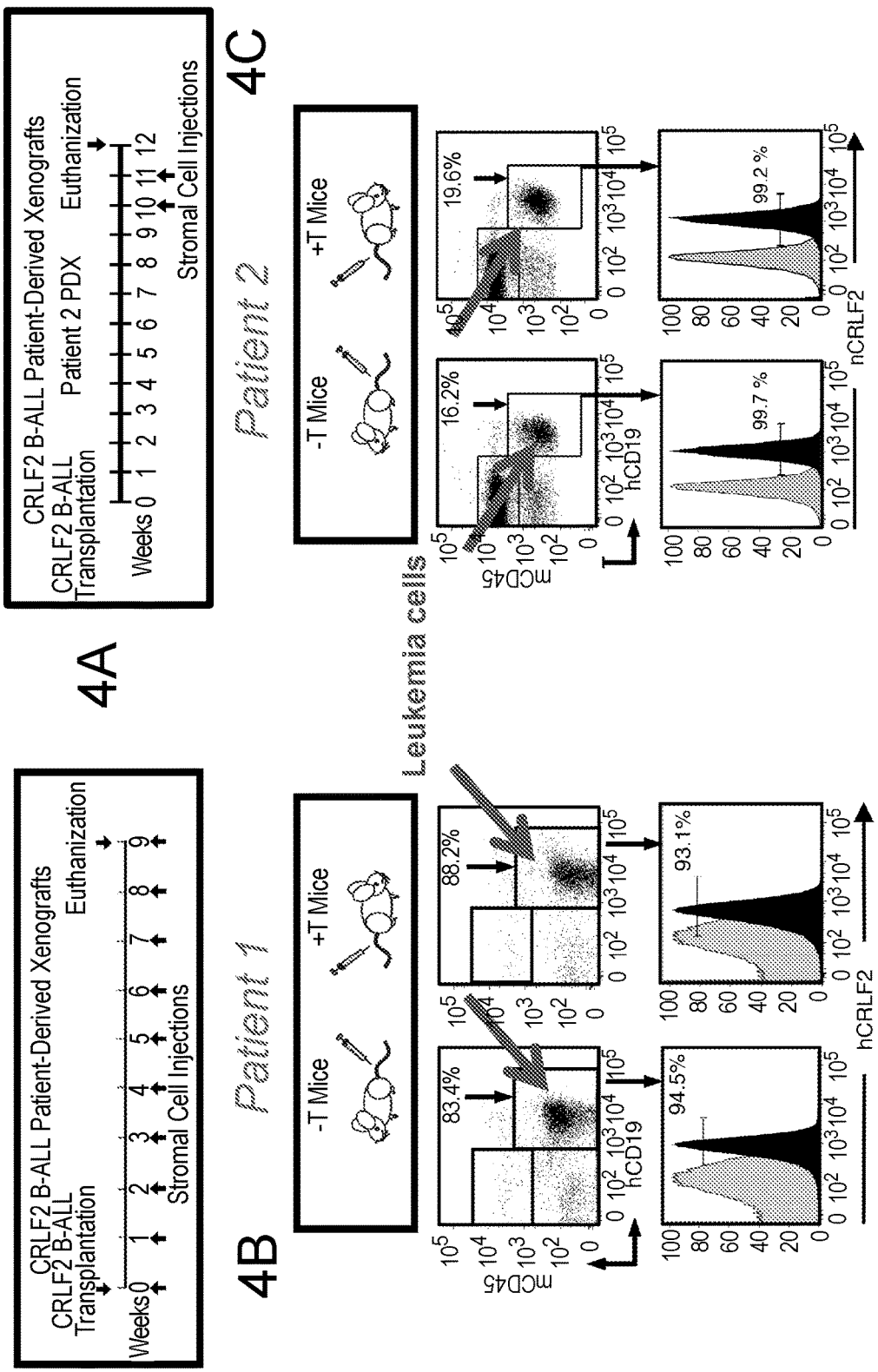
FIG. 4A-4C. Low physiological levels of TSLP have no effect on leukemia cells. (A) Schematic representation of strategy to induce expression of TSLP in PDX model system using two pediatric leukemia patient samples (Patient 1 and Patient 2). (B, C) PDX was established essentially as set forth in Example 1. PDX mice were injected with control stroma or stroma that express hTSLP to produce +T mice with hTSLP serum levels of 4-10 pg/ml hTSLP (top panels). For mice with leukemia cells from patient 1, injections were started immediately and maintained for 9 weeks. For mice with leukemia cells from patient 2, injection were started at 10 weeks and continued for two weeks. Leukemia cells were easily detectable by flow cytometry in bone marrow (BM) harvested from −T PDX and +T PDX mice (middle panels). Lower panels show quantitation of hCRLF2 expression in −T PDX and +T PDX mice verifying that leukemia cells are CRLF2 B-ALL.

Example 3: Low Physiological Levels of TLSP do not have a Therapeutic Effect on Leukemia Cells In this experiment, we produced +T mice with hTSLP serum levels of 4-10 pg/ml (low physiological serum levels). Using these mice we generated +T and −T PDX from two leukemia patients. Human B-ALL cells were easily detectable by flow cytometry in bone marrow (BM) harvested from −T PDX (FIG. 4) middle panels. The results from this experiment demonstrated low physiological levels of TSLP (and overexpression of CRLF2 signaling) in patients allows leukemia cells to grow normally (FIG. 4).

Example 4: High Physiological Levels of TSLP on Multiple Patient Samples

Figure 5A:
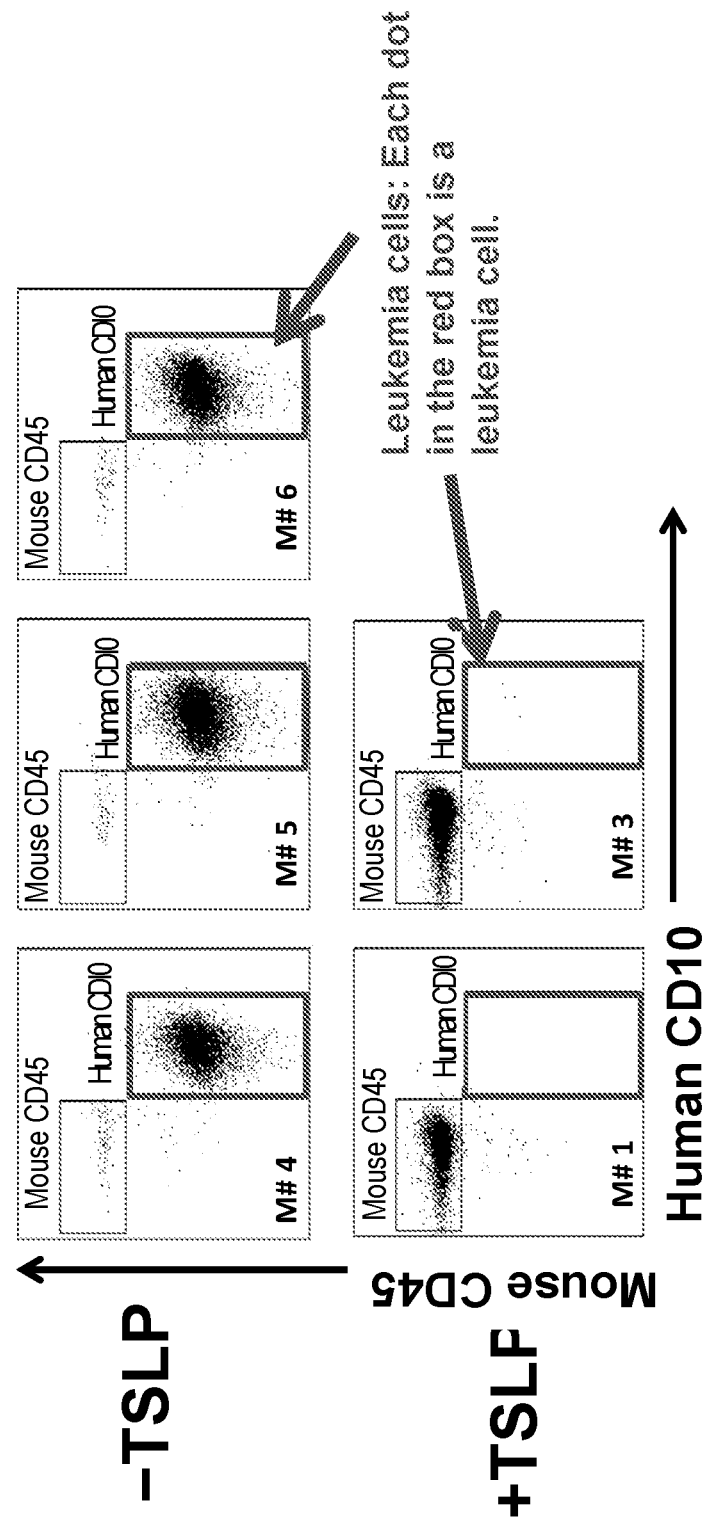
Figures 6A, 6B, 6C, 6D:
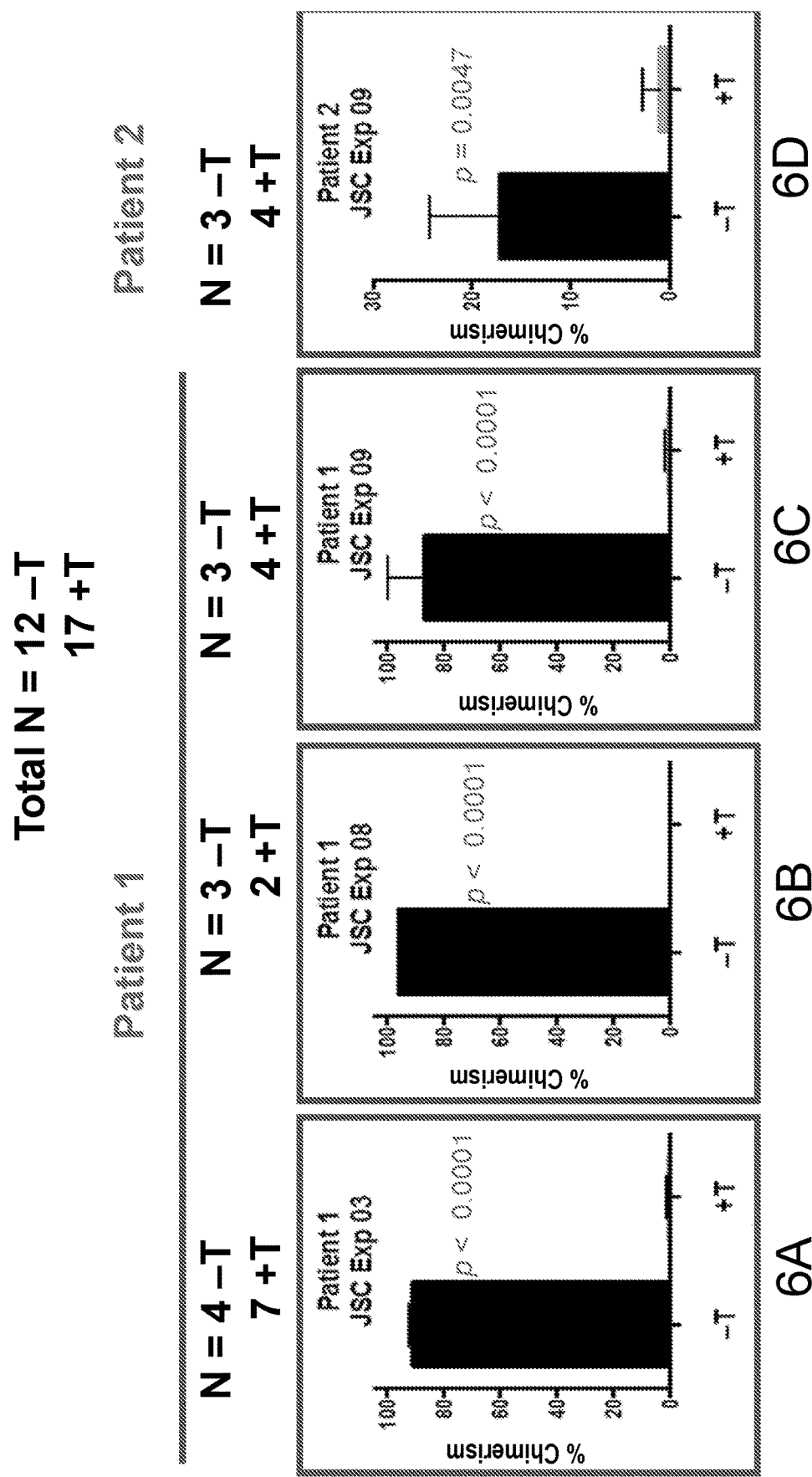
FIG. 6A-6D. TSLP stops CRLF2 B-ALL disease progression in PDX generated from two different patient samples. (A, B, C, and D) Quantitation of the percentage of human leukemia cells in mouse BM obtained from FIGS. 6A and 6B. Data show 4 experiments performed on a total of N=12−T PDX and N=17+T PDX generated from 2 different patient samples. An additional experiment (data not shown) shows similar results providing a total of N=20−T PDX and N=20+T PDX generated from 2 different patient samples. Data confirms CRLF2 B-ALL was essentially cured by circulating hTSLP at elevated physiological levels.

In this experiment, we produced +T mice with hTSLP serum levels of 30-40 pg/ml. Using these mice we generated +T and −T PDX from two leukemia patients. Human B-ALL cells were easily detectable by flow cytometry in bone marrow (BM) harvested from −T PDX (FIGS. 5A and 5B). Consistent with the results from Example 2, leukemia cells were essentially absent from +T PDX confirming CRLF2 B-ALL was essentially cured by circulating hTSLP at elevated physiological levels (FIG. 6).

Example 5: TSLP Induces Upregulation of SOCS Proteins

One mechanism responsible for the transient nature of normal cytokine signaling is that cytokine signals can upregulate the suppressor of Cytokine Signaling (SOCS) genes. SOCS proteins shut down cytokine signals by blocking signaling and degrading signaling components via a negative feedback (exemplified in FIG. 7). SOCS proteins inhibit JAK-STAT signaling by directly interacting with JAKs or the JAK cytokine receptors to prevent JAK phosphorylation. SOCS proteins also target the JAK proteins for proteasomal degradation via ubiquitin ligases (reviewed in Croker B A, Kiu H, Nicholson S E. SOCS regulation of the JAK/STAT signalling pathway. Semin Cell Dev Biol. 2008; 19(4):414-22 and Trengove M C, Ward A C. SOCS proteins in development and disease. Am J Clin Exp Immunol. 2013; 2(1):1-29). In some cases SOCS proteins also target the cytokine receptor for degradation (Kershaw N J, Laktyushin A, Nicola N A, Babon J J. Reconstruction of an active SOCS3-based E3 ubiquitin ligase complex in vitro: identification of the active components and JAK2 and gp130 as substrates. Growth Factors. 2014; 32(1):1-10).

CRLF2 and the IL-7 receptor a chain form a cytokine receptor signaling complex that is uniquely activated by TSLP (FIG. 7) (Russell et al., *Blood*, (2009) 114(13):2688-98 and Palmi et al., *Leukemia*, (2012) 26(10):2245-53. Binding of the TSLP cytokine activates the downstream JAK-STAT5 pathway (FIG. 7) which can be assessed by flow cytometry to detect phosphorylated STAT5 (e.g., see FIG. 10A). TSLP also activates the downstream PI3K/AKT/mTOR pathway (Wohlmann et al., *Biol Chem*. 2010; 391 (2-3):181-6, Nyga et al., *Biochem J*. 2005; 390(Pt 1):359-66, and Tasian et al, *Blood*. 2012; 120(4):833-42) which can be detected by phosphorylated ribosomal protein S6 (e.g., see FIG. 10B).

To determine if SOCS-mediated shutdown of the CRLF2 signaling pathway is a mechanism of the anti-therapeutic effects of TSLP, we compared results of whole genome microarray performed on primary CRLF2 B-ALL cells cultured for 48 hours with and without high-dose recombinant human TSLP (FIG. 8). Significant increases in mRNA from SOCS1, SOCS2, SOCS3 and CISH were induced by high dose TSLP. Using flow cytometry to detect SOCS1 and SOC3S proteins we showed these proteins are upregulated by high dose TSLP in CRLF2 B-ALL cell lines (FIG. 9A) and CRLF2 B-ALL cells from two different pediatric patients with CRLF2 B-ALL (FIG. 9B). These data confirmed both SOCS1 and SOC3S proteins are elevated by high-dose TSLP. Our studies show that TSLP upregulates SOCS1 and SOCS3 proteins in CRLF2 B-ALL cell lines and in CRLF2 B-ALL cells from Patients.

Figure 9A:
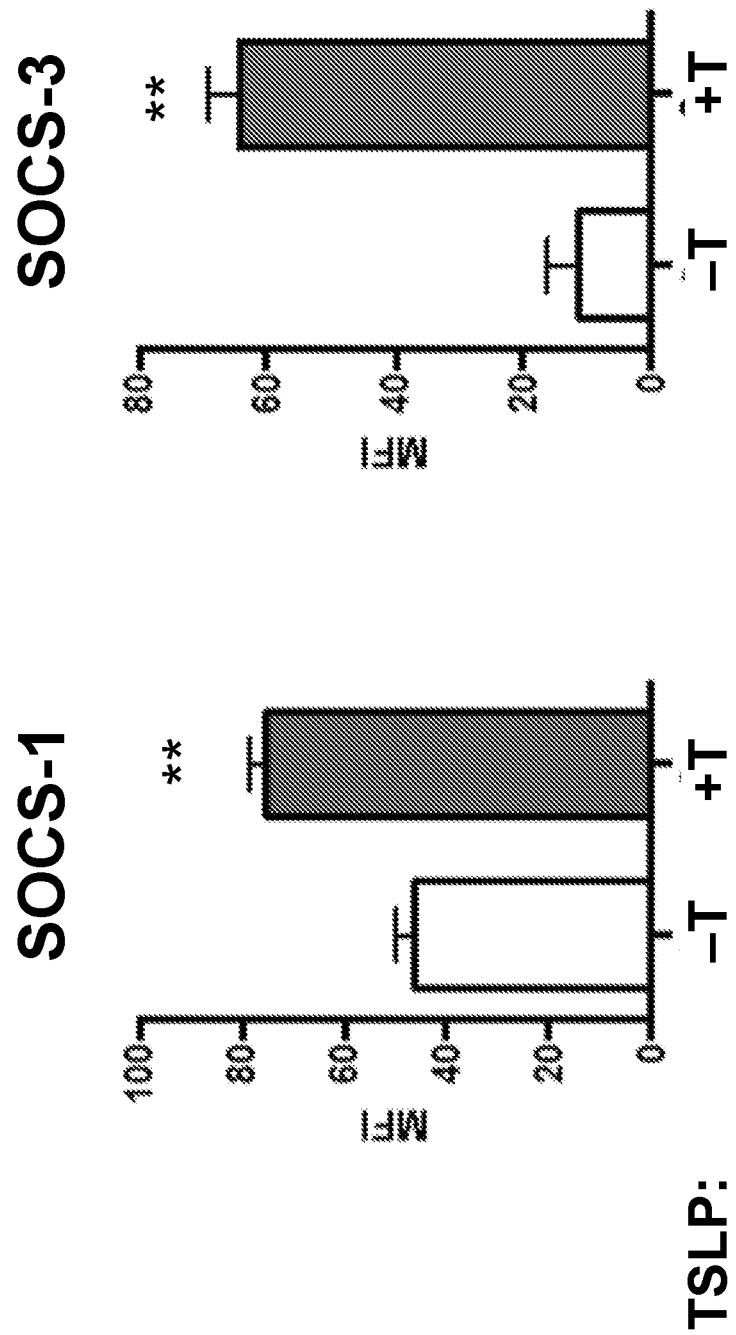
FIG. 9A. TSLP increases SOCS expression in the MUTZ5 cell line. A human CRLF2 B-ALL cell line (MUTZ5) with or without TSLP was evaluated for expression of SOCS genes, SOCS-1 and SOC-3. The human CRLF2 B-ALL cell line MUTZ5 were cultured with and without high dose recombinant human TLSP (15 ng/ml) for 3 days then stained for flow cytometry to detects SOCS1 and SOCS3. (A) shows median fluorescence intensity (MFI) of staining for SOCS protein expression and demonstrates hTSLP induces upregulation of both SOCS1 and SOCS3 in the CRLF2 B-ALL cell line.
Figure 9B:
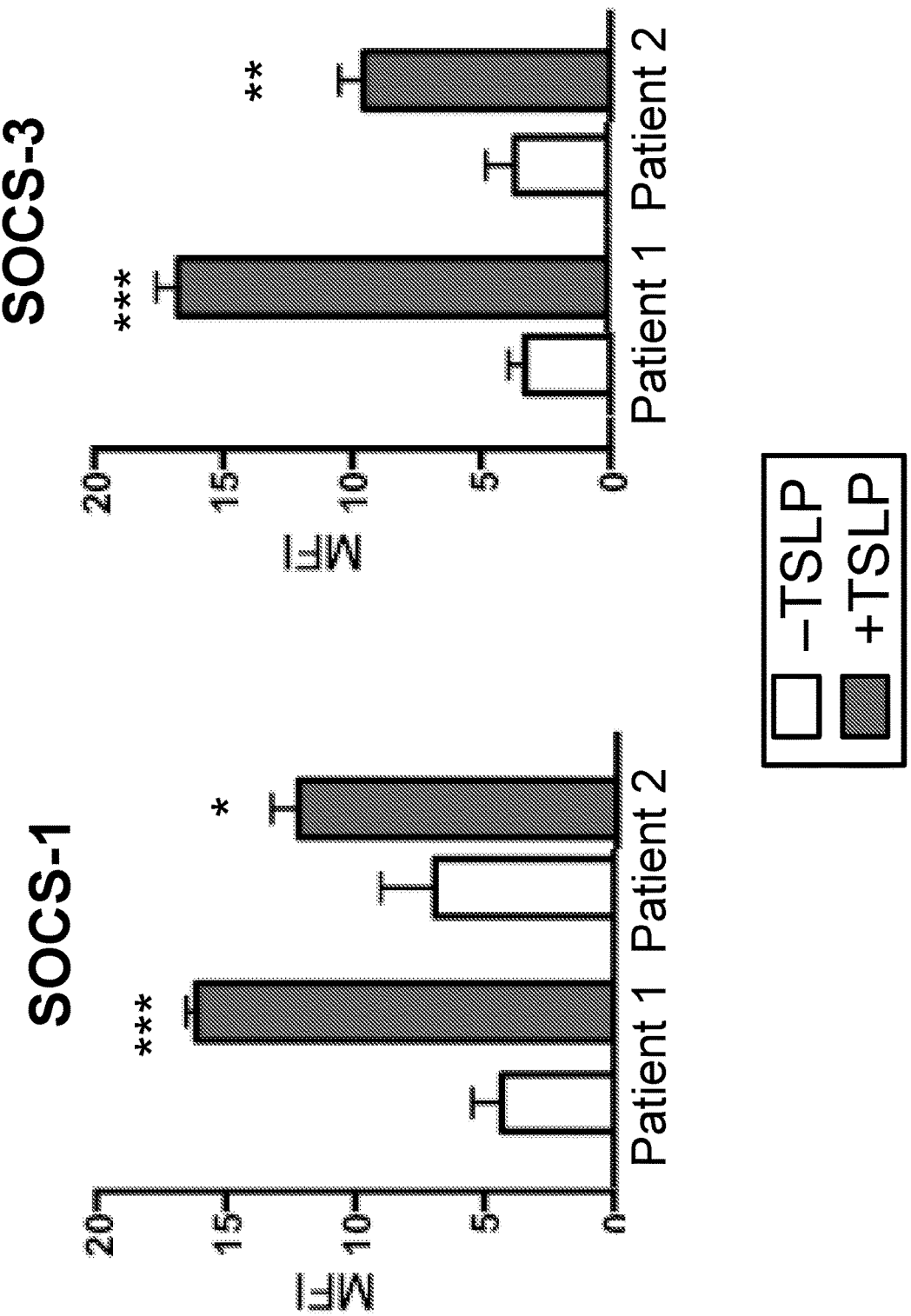
FIG. 9B. High dose TSLP increases SOCS-1 expression in patient CRLF2 B-ALL cells. Patient cells expanded in patient-derived xenograft mice were cultured with and without high dose recombinant human TSLP (hTSLP) and harvested for flow cytometry to assess SOCS1 and SOCS3 protein expression. Data shown are the median fluorescence intensity (MFI) of staining for SOC1 and SOCS3 protein. All TSLP was $E.\ coli$-produced recombinant human TSLP.

To determine if the hTSLP-induced anti-leukemia effects were due to upregulation of SOCS protein expression, we cultured a human CRLF2 B-ALL cell line with or without hTSLP and then evaluated expression of SOCS proteins (FIG. 9A). We evaluated the upregulation of SOCS1 and SOCS3 because these are potent inhibitors of cytokine signaling and inactivation of these genes is a requirement for the development of some leukemias. The human CRLF2 B-ALL cell line MUTZ5, were cultured with and without TLSP for 3 days then stained for flow cytometry to detects SOCS1 and SOCS3. FIG. 9A shows median fluorescence intensity (MFI) of staining for SOCS protein expression. The data shows that hTSLP induces the upregulation of both SOCS1 and SOCS3 in the CRLF2 B-ALL cell line, MUTZ5 (FIG. 9A) and CALL-4 and in primary patient samples (data not shown). Subsequent studies established that TSLP upregulated the SOCS gene, CISH in a similar experiment performed on both cell lines (data not shown). CRLF2 B-ALL cells from two leukemia patients were also assessed for upregulation of SOCS1 and SOCS3 following high dose TSLP and also showed upregulation of these two proteins following culture with high-dose TSLP (FIG. 9B).

Figure 10A:
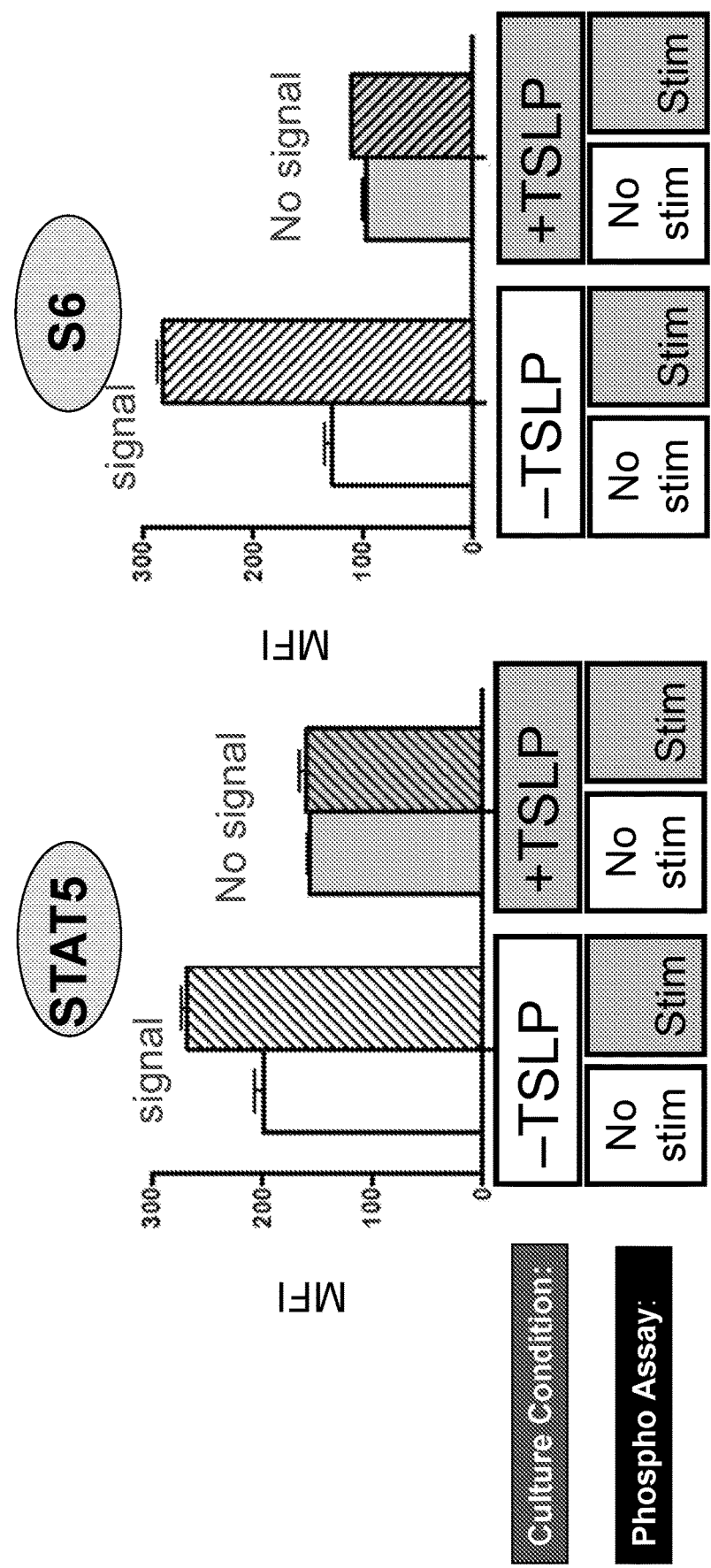
FIGS. 10A-10B. Loss of signaling through CRLF2 corresponds to Upregulation of SOCS-1 and SOCS-3. CRLF2 B-ALL cell lines (A) MUTZ5 and (B) CALL-4 were cultured with or without recombinant human TSLP (15 ng/ml) for 3 days to allow for SOCs protein upregulation and then washed and rested for a few hours to allow loss of phosphorylation. Cells were then left with no stimulation or stimulated briefly (30 min) with TSLP. Phospho flow cytometry was performed to determine levels of phosphorylated STAT5 and phosphorylated ribosomal protein S6. Phosphorylation of STAT5 is an indicator of JAK-STAT pathway activation and phosphorylation of S6 is an indicator of PI3/AKT/mTOR pathway activation. Data are representative of 1 experiment performed in triplicate on the two human cell lines. All TSLP was $E.\ coli$-produced recombinant human TSLP.
Figure 10B:
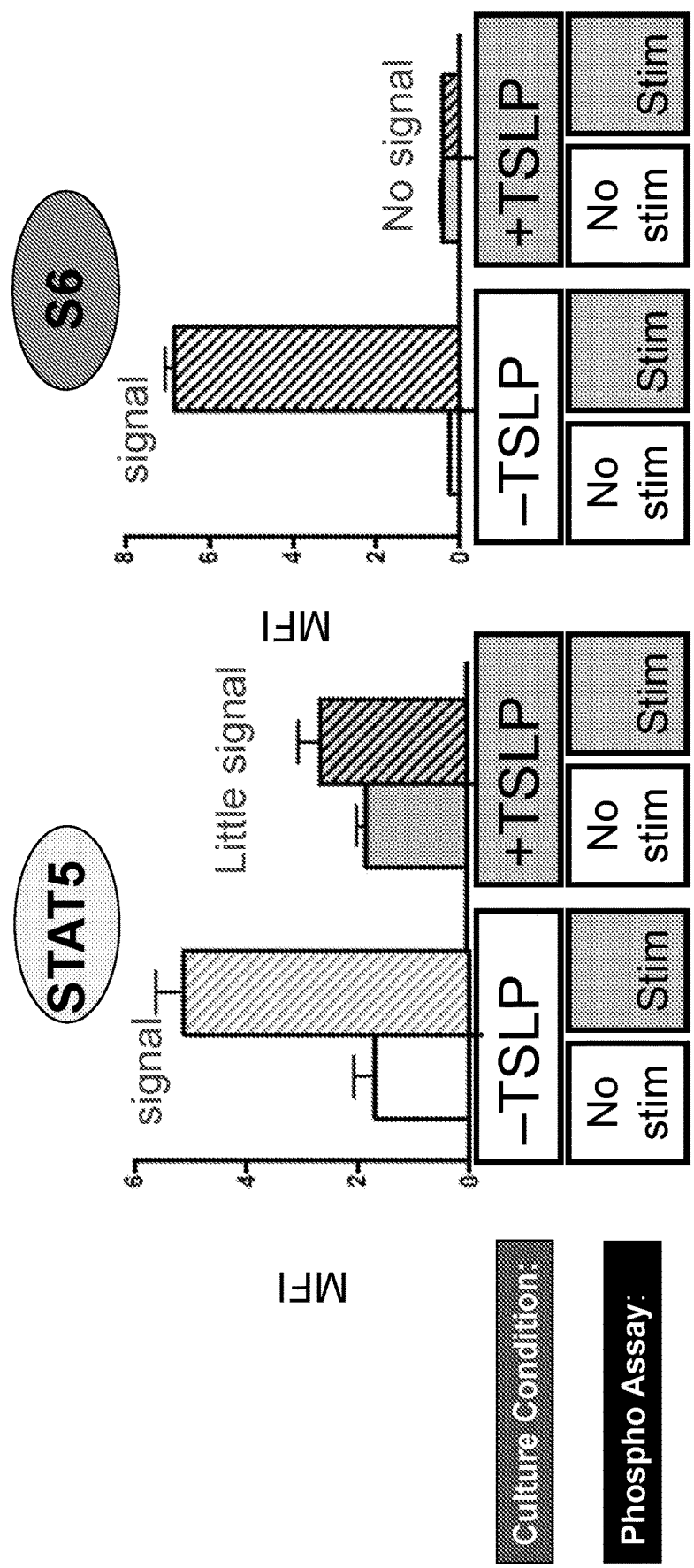

Example 6: Upregulation of SOCS Proteins Corresponds to a Loss of CRLF2 Signaling We determined whether the upregulation of SOCS genes was accompanied by the de-activation of hTSLP-induced signaling (FIGS. 10A and 10B). CRLF2 B-ALL cell lines were cultured with or without hTSLP for 3 days to allow SOCS upregulation, then harvested and assessed for their ability to activate the JAK/STAT5 and PI3/AKT/mTOR pathways following hTSLP stimulation. The cells were assessed by flow cytometry for phosphorylation of STAT 5 and ribosomal protein S6. FIGS. 10A and 10B show the median fluorescent intensity (MFI) of staining for STAT5 phosphorylation and ribosomal S6. As shown in FIGS. 10A and 10B, MUTZ5 cells and CALL-4 cells cultured for 3 days without hTSLP retained their ability to induce phosphorylation of STAT5 and ribosomal protein S6 (downstream of PI3/AKT/mTOR). In contrast, leukemia cells cultured with hTSLP showed no phosphorylation of STAT5 or S6 following hTSLP stimulation.

Figure 11A:
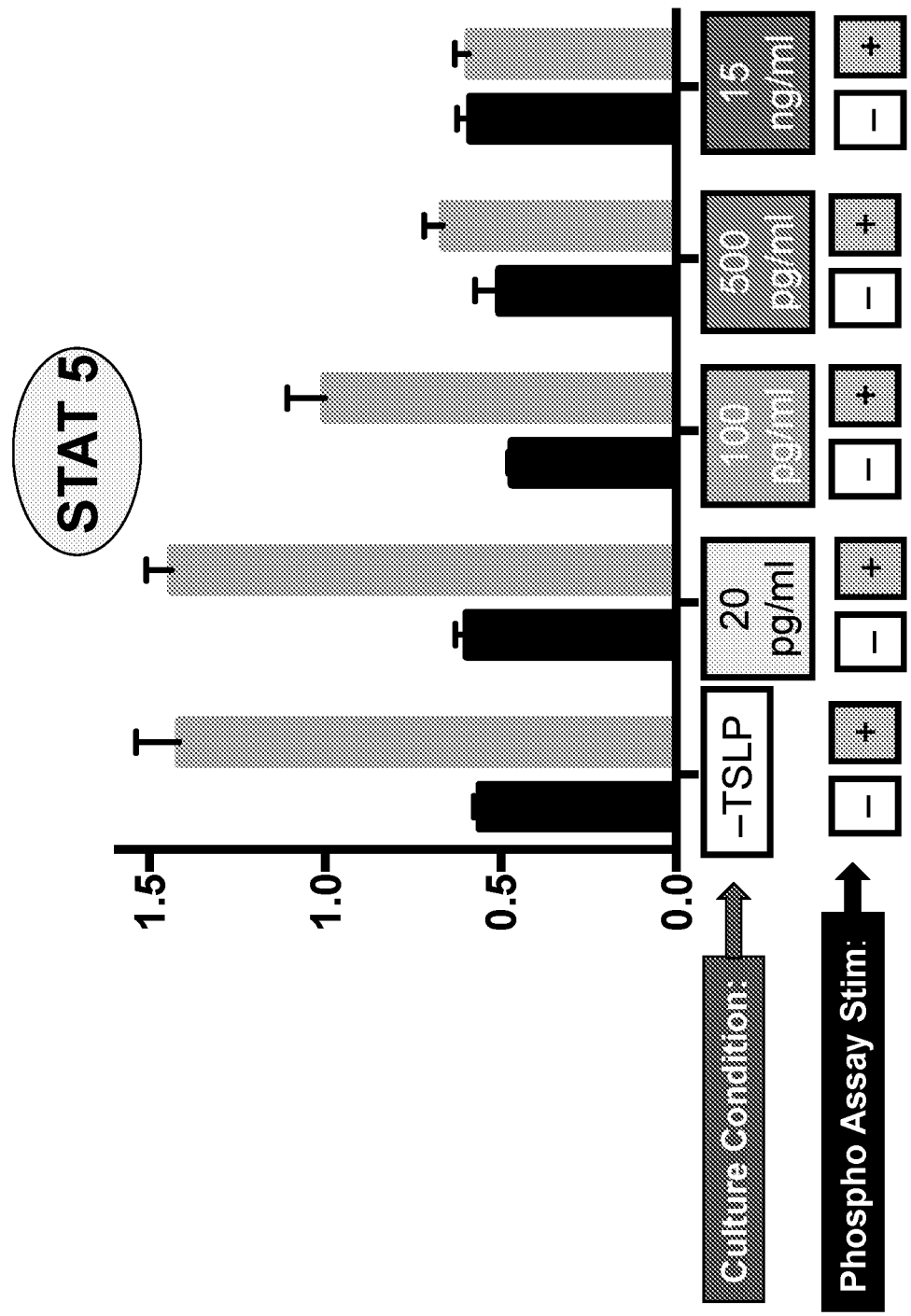
FIG. 11A. TSLP induces a dose dependent loss of CRLF2 signaling. MUTZ5 CRLF2 B-ALL cells were cultured without or with increasing doses of recombinant human TSLP as indicated for 24 hours and then harvested. Harvested cells were washed and rested for 2 hours and then separated into aliquots and stimulated with TSLP or left unstimulated then stained for flow cytometry to assess phosphorylated STAT5. Graphed in black is the level of STAT5 phosphorylation in unstimulated cells versus the level in stimulated cells which is shown in gray. Note that the ability to induce CRLF2 signaling as indicated by increased STAT5 phosphorylation is lost when CRLF2 B-ALL cells are cultured with high-dose TSLP.
Figure 11B:
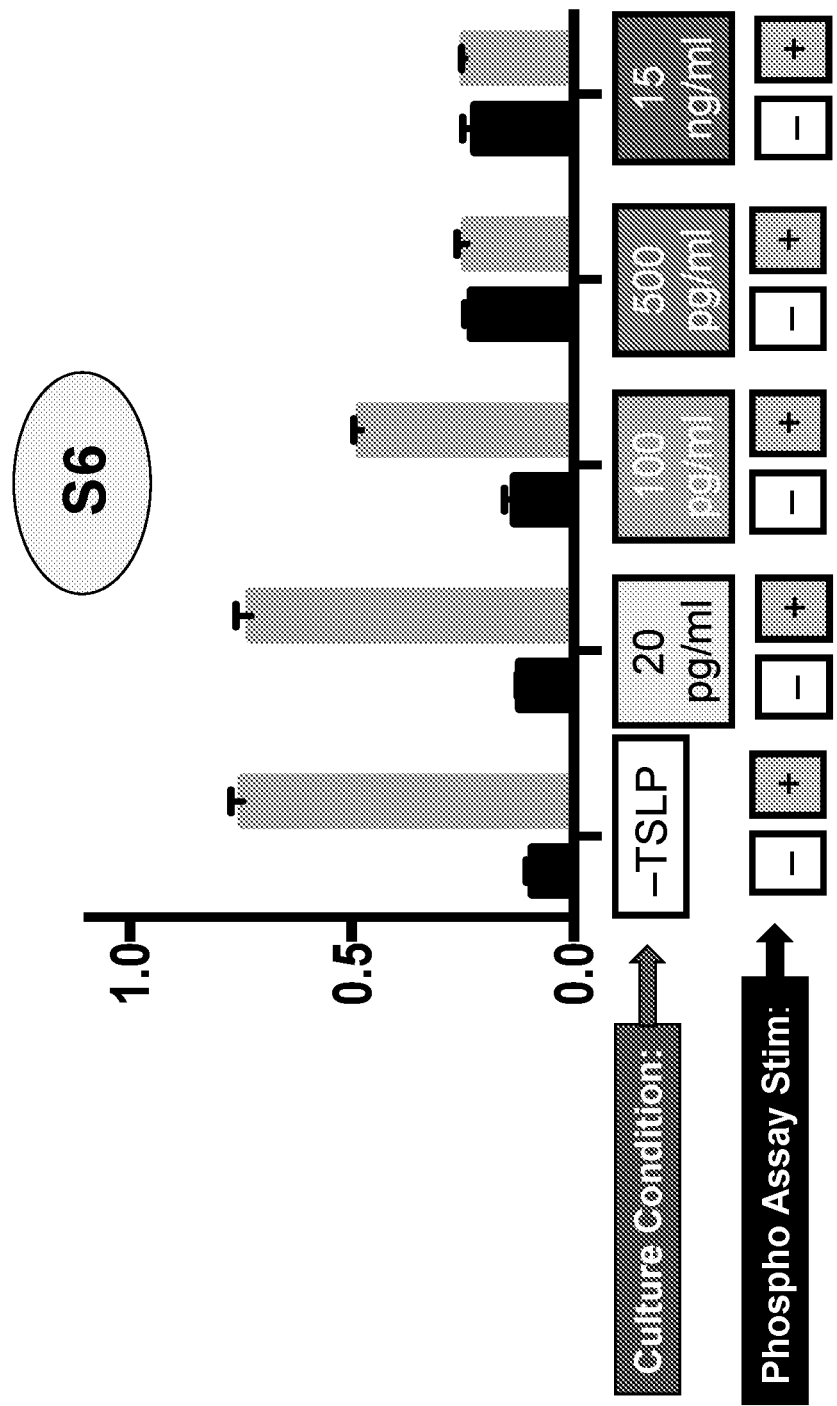
FIG. 11B. TSLP induces a dose dependent loss of CRLF2 signaling. MUTZ5 CRLF2 B-ALL cells were cultured without or with increasing doses recombinant human TSLP as indicated for 24 hours and then harvested. Harvested cells were washed and rested for 2 hours and then separated into aliquots and stimulated with TSLP or left unstimulated then stained for flow cytometry to assess phosphorylated ribosomal protein S6. Graphed in black is the level of ribosomal protein S6 phosphorylation in unstimulated cells versus the level in stimulated cells which is shown in gray. Note that the ability to induce CRLF2 signaling as indicated by increased S6 phosphorylation is lost when CRLF2 B-ALL cells are cultured with high-dose TSLP. TSLP was $E.\ coli$-produced recombinant human TSLP.

We evaluated whether the loss of CRLF2 downstream signaling was a dose dependent response. As shown in FIGS. 11A and 11B, the loss of CRLF2 downstream signals as indicated by an inability to induce STAT5 and ribosomal protein S6 phosphorylation, was a dose dependent response.

Figure 12:
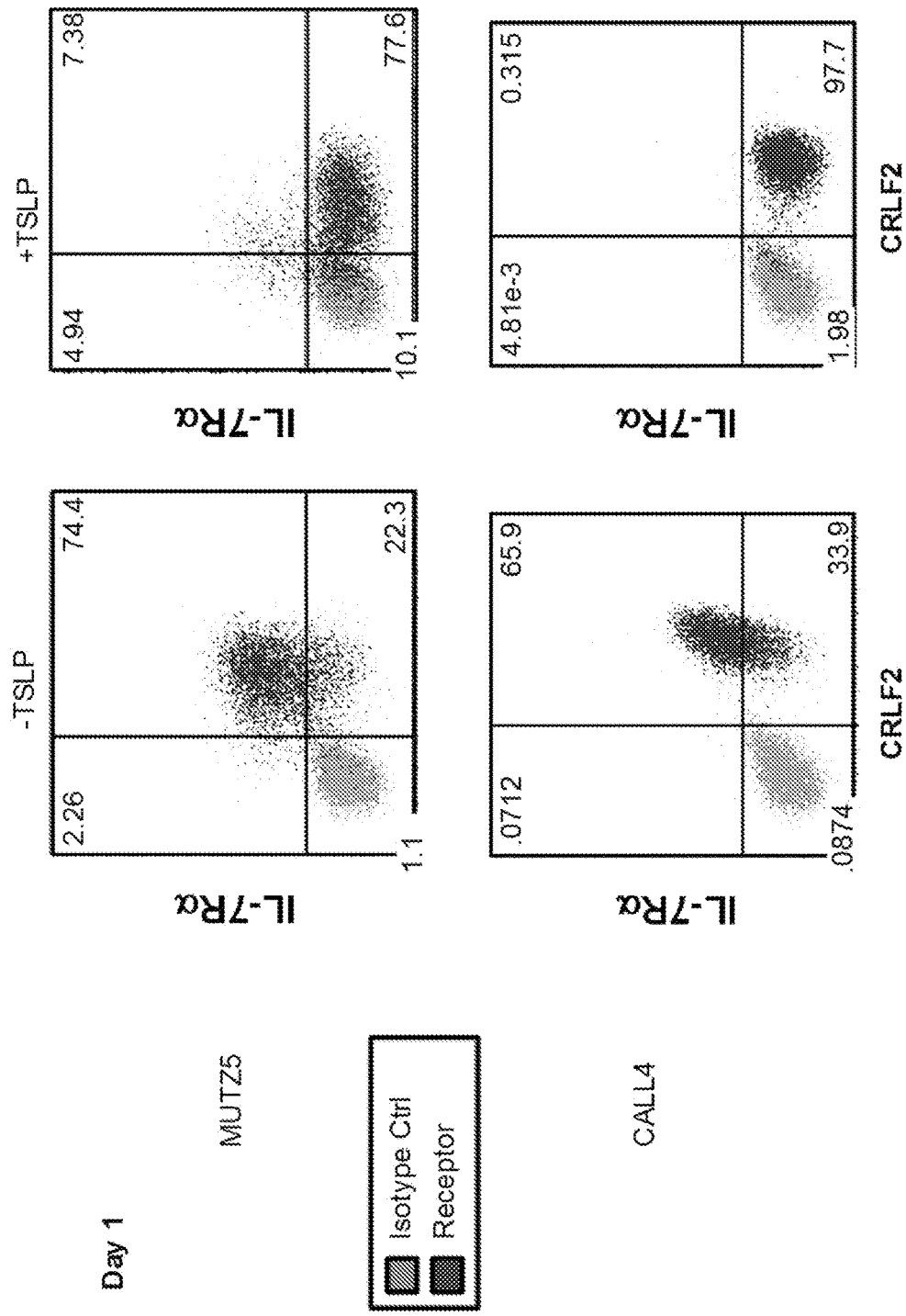
FIG. 12. High-dose TSLP induces a loss of receptor components. The MUTZ5 and CALL4 CRLF2 B-ALL cell lines were cultured with (+T) or without (−T) recombinant human TSLP (15 ng/ml) and harvested at day 1, day 2, and day 3 and stained for flow cytometry to detect the components of the TSLP receptor signaling complex (IL-7Rα and CRLF2). Dot plots from cells harvested at day 1 show receptor component staining in blue and isotype control staining are in red. In the top right panel, the cells with extremely low levels of CRLF2 are the only cells that have not lost all of their IL-7R. Similar results were seen at day 2 and day 3. All TSLP was $E.\ coli$-produced recombinant human TSLP.

We also evaluated whether TSLP-induced loss of receptor components, a mechanism by which SOCS proteins act to shut down cytokine signaling, could be a factor in TSLP-induced loss of CRLF2 downstream signaling. As shown in FIG. 12, high dose TSLP induced a loss of the IL-7Rα receptor component, with much less effect on CRLF2. This effect was sustained as we detected the loss of IL-7 in cells culture for 1 day (FIG. 12), 2 days, and 3 days (data not shown).

Figure 13:
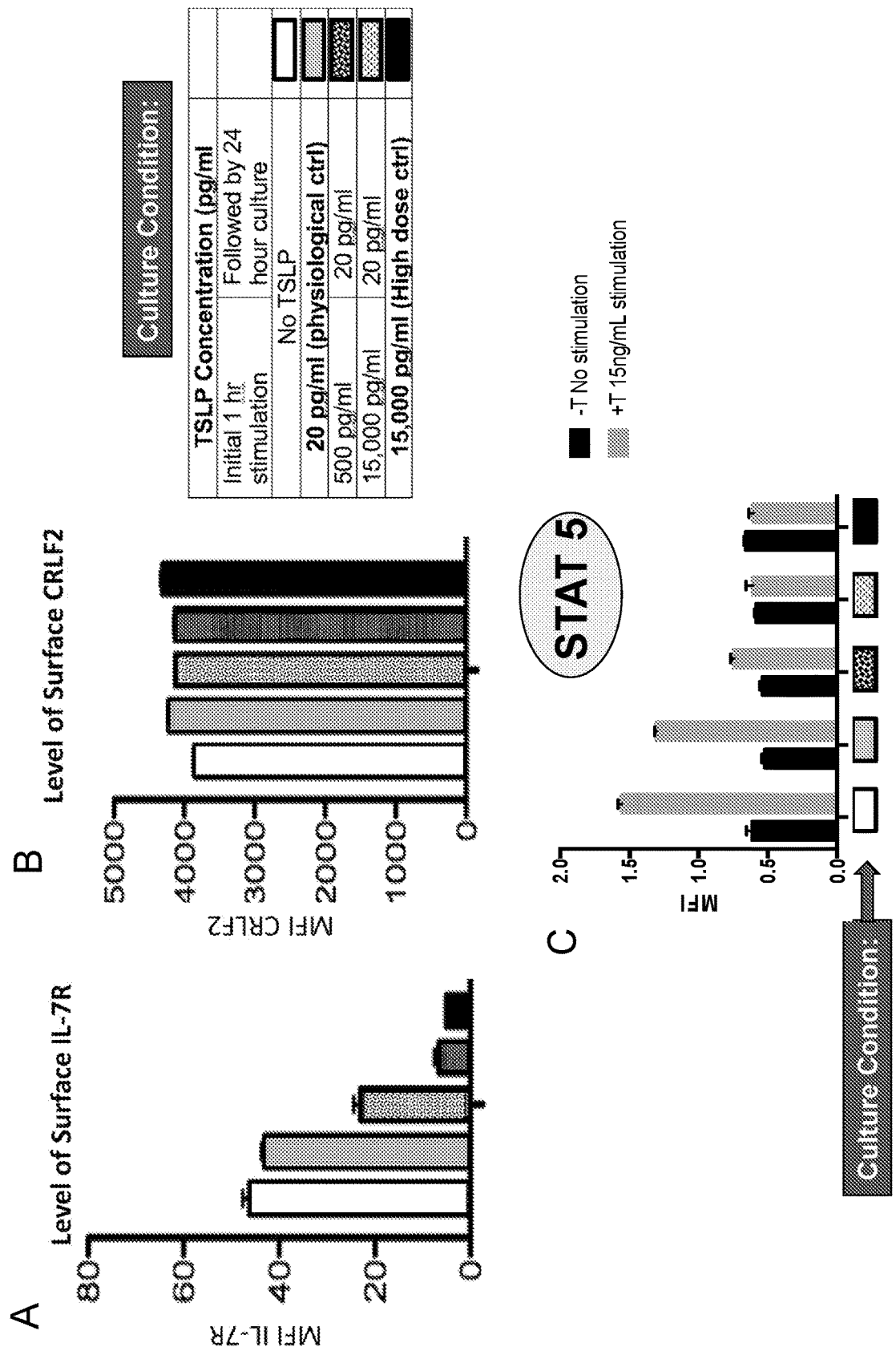
FIG. 13A-13C. CRLF2 B-ALL cells exposed to a 1 hour pulse of TSLP TSLP show a sustained loss of surface IL-7Rα that corresponds to a loss of CRLF2 signaling. MUTZ5 CRLF2 B-ALL cells were exposed to a one hour pulse of $E.\ coli$-produced recombinant human TSLP TSLP at 500 pg/ml or 15,000 pg/ml then washed and returned to culture at low levels of TSLP (20 pg/ml) to mimic physiological conditions for 24 hours. As controls, cells were also incubated with no TSLP or with physiological (20 pg/ml) or a high dose (15,000 pg/ml) of TSLP. After culture cells were harvested and stained for flow cytometry to detect surface (A) IL-7R or CRLF2 (B). In addition, aliquots of cells were harvested, washed and rested for 2 hours then stimulated with or without TSLP for assessment of CRLF2 signaling as indicated by phosphorylation of STAT5. All TSLP was $E.\ coli$ produced recombinant human TSLP.

Next, we performed experiments to determine whether this effect was dose dependent and whether it could be induced if the CRLF2 B-ALL cells were pulsed with cytokine for one hour and then returned to physiological (20 pg/ml) levels. The loss of IL-7Rα was dependent on the dose of TSLP and lasted 24 hours (FIG. 13A) or more (data not shown) after a 1 hour pulse of cytokine. As shown in FIG. 13B, TSLP had little effect on surface CRLF2 levels. To determine whether the loss of IL-7R correlated with the loss of CRLF2 downstream signals, we evaluated STAT 5 phosphorylation (FIG. 13C) and ribosomal protein S6 phosphorylation (data not shown). We found that the loss of surface IL-7Rα correlated with a loss of CRLF2 downstream signaling both in this experiment and in multiple others with various TSLP concentrations (data not shown). These data establish that the TSLP-induced shutdown of CRLF2 signaling is dose dependent, corresponds to the loss of IL-7Rα, and can be achieved following a pulse of cytokine.

Our rationale for the therapeutic anti-leukemia effects of TSLP on CRLF2 while normal B cell precursors are expanded, is as follows: CRLF2 has a high affinity for TSLP and is normally expressed at very low levels on normal B cell progenitors (not detectable by flow cytometry, see FIG. 14, although cells are functionally responsive). CRLF2 binds TSLP and then recruits the IL-7Rα and the receptor complex is internalized, thus when concentrations of TSLP are high, CRLF2 is primed with TSLP. On normal cells, CRLF2 is in lower abundance than IL-7Ra, however in CRLF2 B-ALL it is in much higher abundance than IL-7Rα. Thus, in normal cells the low abundant CRLF2 is not able to internalize all of the IL-7Rα, however, on leukemia cells it quickly can, and although the cell may continue to make IL-7Rα, any IL-7Rα that reaches the cell surface is internalized, one molecule at a time by the CRLF2 already primed with high dose TSLP (even from a one hour cytokine pulse). Signaling of individual molecules would be insufficient to reach the threshold needed to exert a cellular effect. This would also explain why numbers of normal B cell precursors increase with high doses of TSLP, normal cells could maintain sufficient IL-7Rα for continual response to TSLP without signal shut down. Under low levels of TSLP which are normally present in patients (<20 pg/ml) (see FIG. 15, Example 7, herein) the number of CRLF2 receptors with bound TSLP are insufficient to keep pace with the return of newly produced IL-7Rα to the cell surface.

The above data suggests that a rapid assay to measure CRLF2 signaling shut down could be based on the loss of IL-7Rα (e.g., measured at the cell surface). Optionally, assays of phosphorylated STAT5 and/or phosphorylated ribosomal protein S6 could also be included as a confirmatory assay. An IL-7Rα assay measuring CRLF2 signaling could be readily performed using flow cytometry, for example, in flow cytometry laboratories that currently diagnose leukemia, and would be expected to provide data more rapidly than can be achieved with a phosphor assay (e.g., within about 2 hours for an IL-7Rα assay as compared to about 1 day for a phosphor assay).

While TSLP treatment had little impact on CRLF2 expression, it is interesting to note that the few cells shown in FIG. 12, upper right panel (7.38%), that did not show a loss of IL-7Rα were cells with the lowest CRLF2 (consistent with our rationale above and what we have observed in PDX models of normal B cell development). Accordingly, we propose that the relative levels of expression of IL-7Rα and CRLF2 could be used to determine the ratio of CRLF2 to IL-7Rα expression on newly diagnosed leukemias in order to predict those patients who are likely to respond to TSLP treatment (e.g., therapy).

Example 7: Optimizing Dosing and Injection Schedules to Produce Xenograft Mice with hTSLP Serum Levels that Correspond to Leukemia Patients In the above studies, hTSLP was continuously generated from a model system (engineered stroma intraperitoneally injected into PDX mice at weekly intervals). To expand on these studies, we measured the serum levels of TSLP in nine (9) pediatric leukemia patients and observed that the levels of TSLP corresponded to low physiological levels as set forth herein and continued to deplete over time (FIG. 15). It is believed that the low levels of TSLP in these patients allows the leukemia to develop.

By establishing in vivo safety and functional activity of recombinant hTLSP in xenograft mice this model can be used, for example, to assess efficacy and/or toxicity of treatment strategies (e.g., administration of high physiological doses of hTSLP alone or in combination with one or more other agents, such as standard of care agents (e.g., a plurality of chemotherapeutic agents)), dosing, frequency of dosing, and/or relapse treatments (e.g., administration of hTSLP to a leukemia patient in remission in an amount sufficient to achieve or maintain serum levels of hTSLP of at least 30 pg/ml (for example, a human adult or pediatric leukemia patient, where the leukemia patient is administered with a recombinant hTSLP in an appropriate amount, if their serum level of hTLSP falls below 30 pg/ml)).

In one aspect, the dose of recombinant hTSLP that achieves the hTSLP exposure presented in the +T PDX model is determined. In one embodiment, unglycosylated hTSLP produced in *E. coli* (commercially available from ProSpec, East Brunswick, NJ) is used as a suitable substrate. hTSLP is an IL-7 like cytokine and Phase 1 clinical trials for the use of IL-7 as a biologic to effect immune function have been performed using unglycosylated IL-7 produced from *E. coli* (Sportes et al., Phase I study of recombinant human interleukin-7 administration in subjects with refractory malignancy. *Clinical Cancer Research:* 2010; 16(2):727-35). Accordingly, the hTSLP half-life is determined and various dosing strategies can be evaluated.

In another aspect, Balb/c mice are used to establish hTSLP doses required in mice to produce:
(1) normal serum hTSLP levels present in pediatric patients (low physiological dose; e.g., 5-20 pg/ml) and,
(2) levels of hTSLP that showed therapeutic effects in the PDX model of CRLF2 B-ALL, discussed herein (high physiological dose (i.e., serum level of TSLP of at least 30 pg/ml).

Such studies provide information related to the half-life of recombinant hTSLP in xenografted animals. Half-life of hTSLP in xenografts is used to determine doses of hTSLP that give rise to plasma hTSLP levels equivalent to (1) normal and (2) therapeutic hTSLP plasma levels in Balb/c mice.

As shown herein, hTSLP delivered via engineered stroma induced cellular effects on both normal and malignant B cell precursors (FIG. 2). hTSLP induced expansion of normal B cell precursors at both low and high physiological doses (data not shown). hTSLP induced a loss of CRLF2 B-ALL cells at high (FIGS. 5A and 5B), but not low physiological doses (FIG. 4). To verify in vivo functional effects of recombinant human hTSLP at the cellular level hTSLP effects on the production of normal and malignant B cell precursors at doses that achieve low and high physiological levels is determined. To verify in vivo functional effects of recombinant human hTSLP at the molecular level hTSLP-induced signaling, as well as SOCS gene expression in CRLF2 B-ALL cells harvested from control and hTSLP treated mice that receive low and high physiological doses is evaluated.

Example 8: High Dose EGF Shuts Down EGFR Downstream Signaling in Cervical, Lung and Ovarian Cancer Cells To determine the potential of high dose cytokines as a biologic therapy for other cancers we evaluate the ability of high dose Flt ligand and EGF to shut down signaling pathways where those receptors are known to play major roles. We tested flt ligand on the acute myeloid leukemia cell line MOLM14 which has an internal duplication of the flt3 receptor intracellular signaling domain which drives the leukemia. We did not detect a difference in phosphorylation of STAT5 with or without high dose flt ligand (data not shown).

Figure 16:
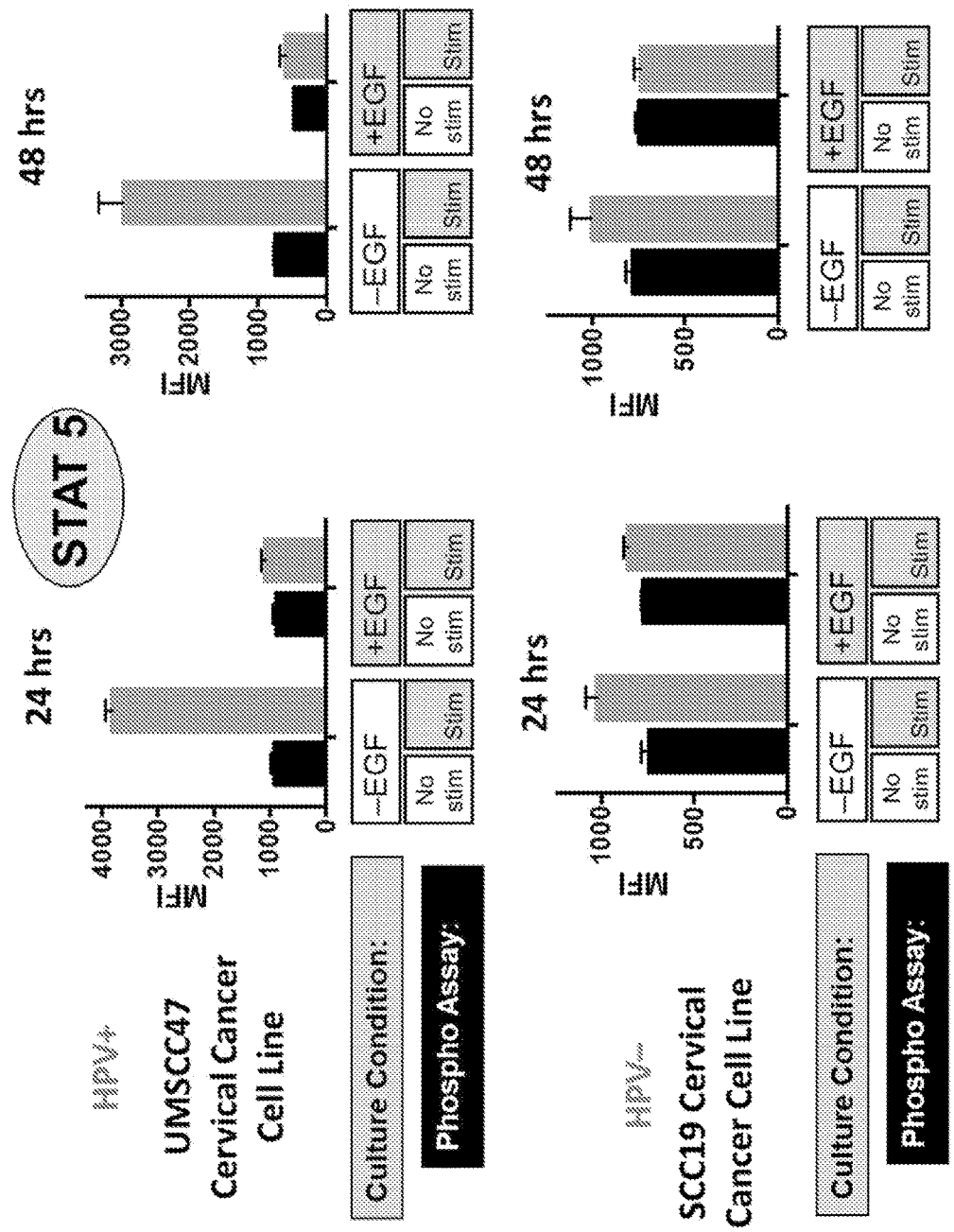
FIG. 16. High-dose EGF shuts down EGFR downstream signaling in solid tumor cervical cancer cells. The cervical cancer cell lines, UMSCC47 and SCC19 were cultured with or without high dose EGFR (200 ng/ml) for 24 or 48 hours then harvested, washed, and rested for 2 hours. Rested cells were split into aliquots and briefly stimulated with EGF then stained for flow cytometry to detect STAT5 phosphorylation. Graphed is the median fluorescence intensity of staining for phosphorylated STAT 5.
Figure 17:
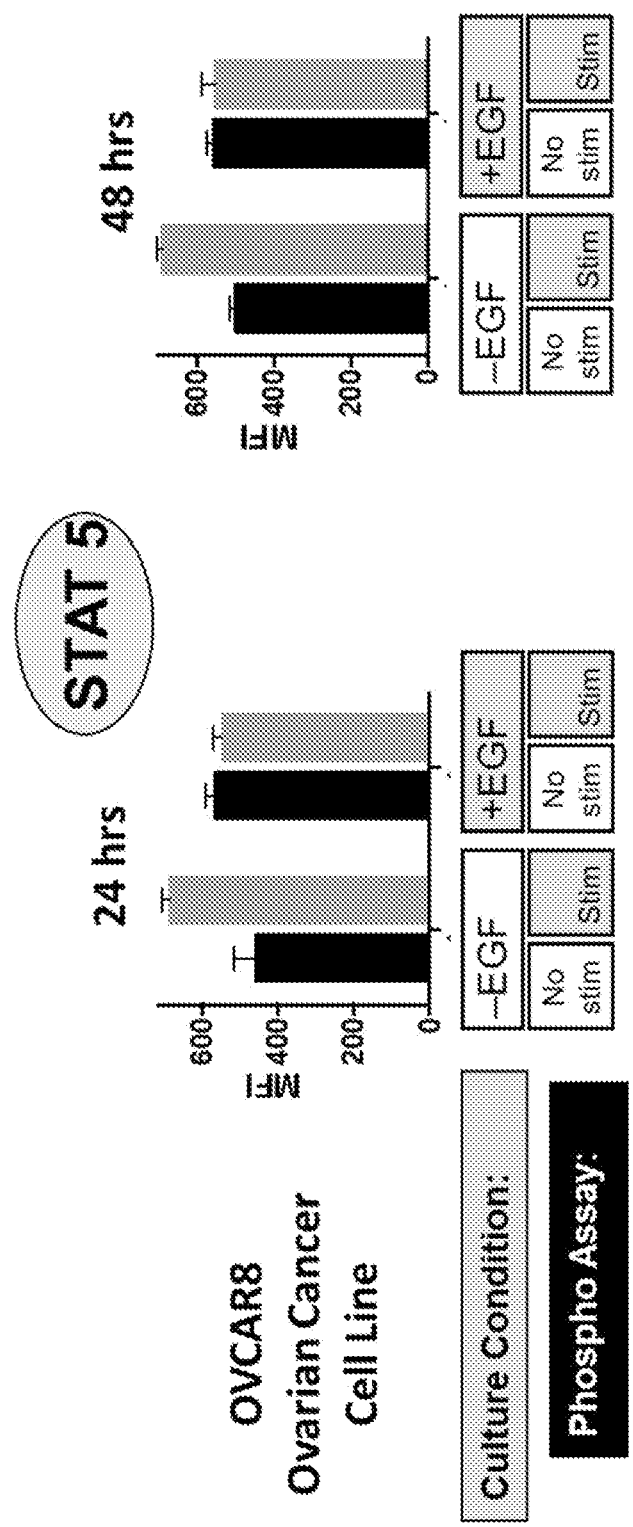
FIG. 17. High-dose EGF shuts down EGFR downstream signaling in solid tumor ovarian cancer cells. The ovarian cancer cell line, OVCAR8 was cultured with or without high dose EGFR (200 ng/ml) for 24 or 48 hours then harvested, washed, and rested for 2 hours. Rested cells were split into aliquots and briefly stimulated with EGF then stained for flow cytometry to detect STAT5 phosphorylation. Graphed is the median fluorescence intensity of staining for phosphorylated STAT 5.
Figure 18:
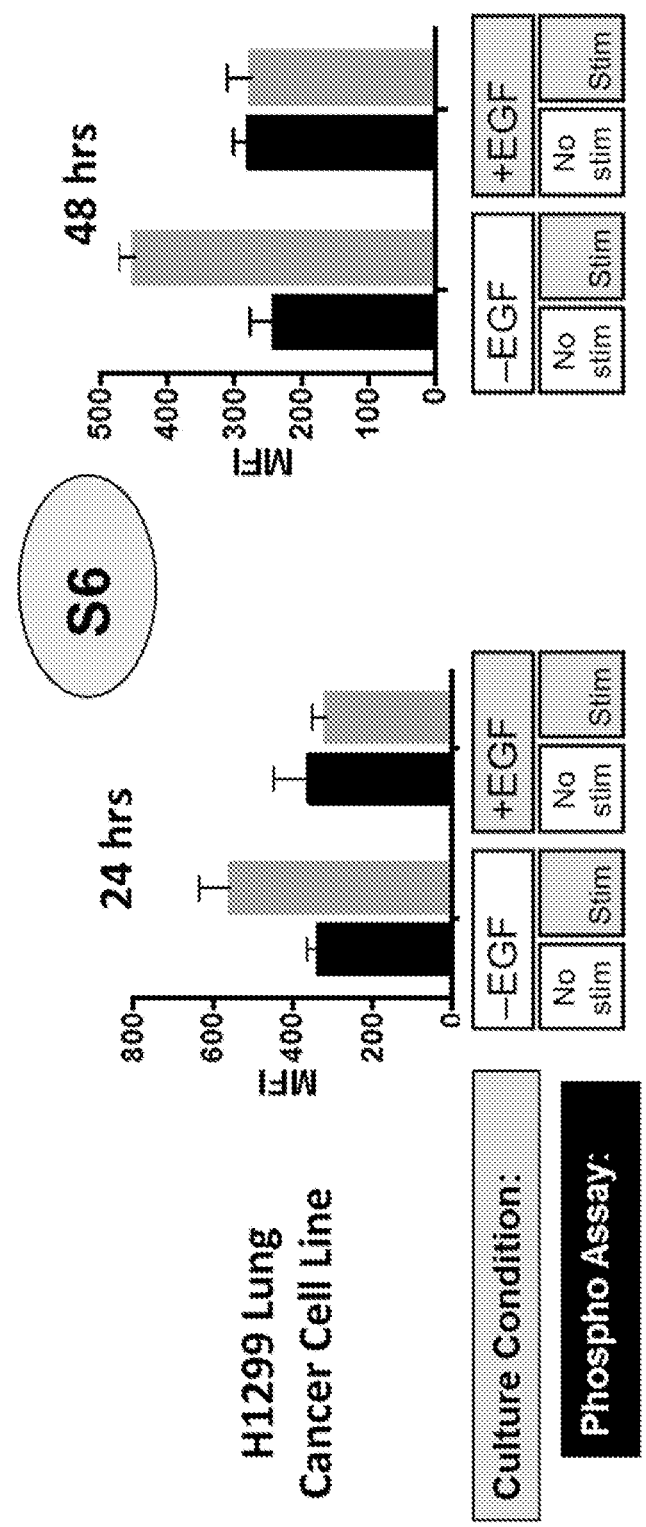
FIG. 18. High-dose EGF shuts down EGFR downstream signaling in solid tumor lung cancer cells. The lung cancer cell line, H1299 was cultured with or without high dose EGFR (200 ng/ml) for 24 or 48 hours then harvested, washed, and rested for 2 hours. Rested cells were split into aliquots and briefly stimulated with EGF then stained for flow cytometry to detect ribosomal protein S6 phosphorylation. Graphed is the median fluorescence intensity of staining for phosphorylated S6.

We also evaluated cell lines from solid tumor types in which EFGR signaling is known to play a role. We cultured two cervical cancer cell lines (UMSCC47 and SCC19, HPV+ and one HPV– tumors, respectively) with high dose EGF, (200 ng/ml; plasma levels of EGF are reported to average about 39 pg/ml (Balcan et al., Int. J. Gynecol Cancer (2012) 7:1138-42). Cells were harvested after 24 and 48 hours, washed, rested and then briefly stimulated with EGF to determine whether culture with high dose EGF resulted in a loss of EGFR signaling as indicated by a loss of the ability to phosphorylate STAT5. As shown in FIG. 16, culture with high dose EGF shut down EGFR signaling as measured by STAT5 phosphorylation and this was maintained after 48 hours. Similar results were seen with the ovarian cancer cell line OVCAR8 (FIG. 17). For lung cancer, we evaluated ribosomal protein S6 phosphorylation downstream of EGFR signaling. Similar to our observations for cervical and ovarian cancer, culturing the lung cancer cell line H1299 with high dose EGF shut down EGFR signaling. This was indicated by a loss of the ability to phosphorylate S6 in response to brief stimulation with EGF (FIG. 18). These data provide evidence that high dose EGF, like high dose TSLP, has the ability to shut down the corresponding downstream signaling pathways.

All publications and patents cited in this specification are herein incorporated by reference as if each individual publication or patent were specifically and individually indicated to be incorporated by reference and are incorporated herein by reference to disclose and describe the methods and materials in connection with which the publications are cited.

The inventions have been described broadly and generically herein. Each of the narrower species and subgeneric groupings falling within the generic disclosure also form part of the invention. In addition, where features or aspects of the invention are described in terms of Markush groups, those skilled in the art will recognize that the invention is also thereby described in terms of any individual member or subgroup of members of the Markush group.

It should be understood that although the present invention has been specifically disclosed by certain aspects, embodiments, and optional features, modification, improvement, and variation of such aspects, embodiments, and optional features can be resorted to by those skilled in the art, and that such modifications, improvements, and variations are considered to be within the scope of this disclosure.

TABLE 1

Informal Sequence Listing

| | | |
|---|---|---|
| SEQ ID NO: 1 | human TSLP | MFPFALLYVLSVSFRKIFILQLVGLVLTYDFTNCDFEKIKAAYLSTISKDLI TYMSGTKSTEFNNTVSCSNRPHCLTEIQSLTFNPTAGCASLAKEMFA MKTKAALAIWCPGYSETQINATQAMKKRRKRKVTTNKCLEQVSQLQ GLWRRFNRPLLKQQ |
| SEQ ID NO: 2 | human EGF | MLLTLIILLP VVSKFSFVSL SAPQHWSCPE GTLAGNGNST CVGPAPFLIF SHGNSIFRID TEGTNYEQLV VDAGVSVIMD FHYNEKRIYW VDLERQLLQR VFLNGSRQER VCNIEKNVSG MAINWINEEV IWSNQQEGII TVTDMKGNNS HILLSALKYP ANVAVDPVER FIFWSSEVAG SLYRADLDGV GVKALLETSE KITAVSLDVL DKRLFWIQYN REGSNSLICS CDYDGGSVHI SKHPTQHNLF AMSLFGDRIF YSTWKMKTIW IANKHTGKDM VRINLHSSFV PLGELKVVHP LAQPKAEDDT WEPEQKLCKL RKGNCSSTVC GQDLQSHLCM CAEGYALSRD RKYCEDVNEC AFWNHGCTLG CKNTPGSYYC TCPVGFVLLP DGKRCHQLVS CPRNVSECSH DCVLTSEGPL CFCPEGSVLE RDGKTCSGCS SPDNGGCSQL CVPLSPVSWE CDCFPGYDLQ LDEKSCAASG PQPFLLFANS QDIRHMHFDG TDYGTLLSQQ MGMVYALDHD PVENKIYFAH TALKWIERAN MDGSQRERLI EEGVDVPEGL AVDWIGRRFY WTDRGKSLIG RSDLNGKRSK IITKENISQP RGIAVHPMAK RLFWTDTGIN PRIESSSLQG LGRLVIASSD LIWPSGITID FLTDKLYWCD AKQSVIEMAN LDGSKRRRLT QNDVGHPFAV AVFEDYVWFS DWAMPSVMRV NKRTGKDRVR LQGSMLKPSS LVVVHPLAKP GADPCLYQNG GCEHICKKRL GTAWCSCREG FMKASDGKTC LALDGHQLLA GGEVDLKNQV TPLDILSKTR VSEDNITESQ HMLVAEIMVS DQDDCAPVGC SMYARCISEG EDATCQCLKG FAGDGKLCSD IDECEMGVPV CPPASSKCIN TEGGYVCRCS EGYQGDGIHC LDIDECQLGE HSCGENASCT NTEGGYTCMC AGRLSEPGLI CPDSTPPPHL REDDHHYSVR NSDSECPLSH DGYCLHDGVC MYIEALDKYA CNCVVGYIGE RCQYRDLKWW ELRHAGHGQQ QKVIVVAVCV VVLVMLLLLS LWGAHYYRTQ KLLSKNPKNP YEESSRDVRS RRPADTEDGM SSCPQPWFVV IKEHQDLKNG GQPVAGEDGQ AADGSMQPTS WRQEPQLCGM GTEQGCWIPV SSDKGSCPQV MERSFHMPSY GTQTLEGGVE KPHSLLSANP LWQQRALDPP HQMELTQ |
| SEQ ID NO: 3 | human IL-7 | MFHVSFRYIF GLPPLILVLL PVASSDCDIE GKDGKQYESV LMVSIDQLLD SMKEIGSNCL NNEFNFFKRH ICDANKEGMF LFRAARKLRQ FLKMNSTGDF DLHLLKVSEG TTILLNCTGQ VKGRKPAALG EAQPTKSLEE NKSLKEQKKL NDLCFLKRLL QEIKTCWNKI LMGTKEH |
| SEQ ID NO: 4 | CRLF2 | MGRLVLLWGAAVFLLGGWMALGQGGAAEGVQIQIIYFNLETVQVT WNASKYSRTNLTFHYRFNGDEAYDQCTNYLLQEGHTSGCLLDAEQR DDILYFSIRNGTHPVFTASRWMVYYLKPSSPKHVRFSWHQDAVTVTC SDLSYGDLLYEVQYRSPFDTEWQSKQENTCNVTIEGLDAEKCYSFWV RVKAMEDVYGPDTYPSDWSEVTCWQRGEIRDACAETPTPPKPKLSK FILISSLAILLMVSLLLLSLWKLWRVKKFLIPSVPDPKSIFPGLFEIHQGNF QEWIDTQNVAHLHKMAGAEQESGPEEPLVVQLAKTEAESPRMLDP QTEEKEASGGSLQLPHQPLQGGDVVTIGGFTFVMNDRSYVAL |
| SEQ ID NO: 5 | IL-7Rα | MTILGTTFGMVFSLLQVVSGESGYAQNGDLEDAELDDYSFSCYSQLE VNGSQHSLTCAFEDPDVNITNLEFEICGALVEVKCLNFRKLQEIYFIETK KFLLIGKSNICVKVGEKSLTCKKIDLTTIVKPEAPFDLSVVYREGANDFV VTFNTSHLQKKYVKVLMHDVAYRQEKDENKWTHVNLSSTKLTLLQR KLQPAAMYEIKVRSIPDHYFKGFWSEWSPSYYFRTPEINNSSGEMDPI LLTISILSFFSVALLVILACVLWKKRIKPIVWPSLPDHKKTLEHLCKKPRK |

TABLE 1-continued

Informal Sequence Listing

|  |  |  |
|---|---|---|
|  |  | NLNVSFNPESFLDCQIHRVDDIQARDEVEGFLQDTFPQQLEESEKQRL<br>GGDVQSPNCPSEDVVITPESFGRDSSLTCLAGNVSACDAPILSSSRSLD<br>CRESGKNGPHVYQDLLLSLGTTNSTLPPPFSLQSGILTLNPVAQGQPIL<br>TSLGSNQEEAYVTMSSFYQNQ |
| SEQ ID<br>NO: 6 | EGFR | MRPSGTAGAA LLALLAALCP ASRALEEKKV CQGTSNKLTQ<br>LGTFEDHFLS LQRMFNNCEV VLGNLEITYV QRNYDLSFLK<br>TIQEVAGYVL IALNTVERIP LENLQIIRGN MYYENSYALA<br>VLSNYDANKT GLKELPMRNL QEILHGAVRF SNNPALCNVE<br>SIQWRDIVSS DFLSNMSMDF QNHLGSCQKC DPSCPNGSCW<br>GAGEENCQKL TKIICAQQCS GRCRGKSPSD CCHNQCAAGC<br>TGPRESDCLV CRKFRDEATC KDTCPPLMLY NPTTYQMDVN<br>PEGKYSFGAT CVKKCPRNYV VTDHGSCVRA CGADSYEMEE<br>DGVRKCKKCE GPCRKVCNGI GIGEFKDSLS INATNIKHFK<br>NCTSISGDLH ILPVAFRGDS FTHTPPLDPQ ELDILKTVKE<br>ITGFLLIQAW PENRTDLHAF ENLEIIRGRT KQHGQFSLAV<br>VSLNITSLGL RSLKEISDGD VIISGNKNLC YANTINWKKL<br>FGTSGQKTKI ISNRGENSCK ATGQVCHALC SPEGCWGPEP<br>RDCVSCRNVS RGRECVDKCN LLEGEPREFV ENSECIQCHP<br>ECLPQAMNIT CTGRGPDNCI QCAHYIDGPH CVKTCPAGVM<br>GENNTLVWKY ADAGHVCHLC HPNCTYGCTG PGLEGCPTNG<br>PKIPS IATGM VGALLLLLVV ALGIGLFMRR RHIVRKRTLR<br>RLLQERELVE PLTPSGEAPN QALLRILKET EFKKIKVLGS<br>GAFGTVYKGL WIPEGEKVKI PVAIKELREA TSPKANKEIL<br>DEAYVMASVD NPHVCRLLGI CLTSTVQLIT QLMPFGCLLD<br>YVREHKDNIG SQYLLNWCVQ IAKGMNYLED RRLVHRDLAA<br>RNVLVKTPQH VKITDFGLAK LLGAEEKEYH AEGGKVPIKW<br>MALESILHRI YTHQSDVWSY GVTVWELMTF GSKPYDGIPA<br>SEISSILEKG ERLPQPPICT IDVYMIMVKC WMIDADSRPK<br>FRELIIEFSK MARDPQRYLV IQGDERMHLP SPTDSNFYRA<br>LMDEEDMDDV VDADEYLIPQ QGFFSSPSTS RTPLLSSLSA<br>TSNNSTVACI DRNGLQSCPI KEDSFLQRYS SDPTGALTED<br>SIDDTFLPVP EYINQSVPKR PAGSVQNPVY HNQPLNPAPS<br>RDPHYQDPHS TAVGNPEYLN TVQPTCVNST FDSPAHWAQK<br>GSHOISLDNP DYQQDFFPKE AKPNGIFKGS TAENAEYLRV<br>APQSSEFIGA |
| SEQ ID<br>NO: 7 | human<br>SOCS1 | MVAHNQVAADNAVSTAAEPRRRPEPSSSSSSSPAAPARPRPCPAVP<br>APAPGDTHFRTFRSHADYRRITRASALLDACGFYWGPLSVHGAHERL<br>RAEPVGTFLVRDSRQRNCFFALSVKMASGPTSIRVHFQAGRFHLDGS<br>RESFDCLFELLEHYVAAPRRMLGAPLRQRRVRPLQELCRQRIVATVGR<br>ENLARIPLNPVLRDYLSSFPFQI |
| SEQ ID<br>NO: 8 | human<br>SOCS 2 | MTLRCLEPSGNGGEGTRSQWGTAGSAEEPSPQAARLAKALRELGQT<br>GWYWGSMTVNEAKEKLKEAPEGTFLIRDSSHSDYLLTISVKTSAGPT<br>NLRIEYQDGKFRLDSIICVKSKLKQFDSVVHLIDYYVQMCKDKRTGPE<br>APRNGTVHLYLTKPLYTSAPSLQHLCRLTINKCTGAIWGLPLPTRLKDY<br>LEEYKFQV |
| SEQ ID<br>NO: 9 | human<br>50053 | MVTHSKFPAAGMSRPLDTSLRLKTFSSKSEYQLVVNAVRKLQESGFY<br>WSAVTGGEANLLLSAEPAGTFLIRDSSDQRHFFTLSVKTQSGTKNLRI<br>QCEGGSFSLQSDPRSTQPVPRFDCVLKLVHHYMPPPGAPSFPSPPTE<br>PSSEVPEQPSAQPLPGSPPRRAYYIYSGGEKIPLVLSRPLSSNVATLQHL<br>CRKTVNGHLDSYEKVTQLPGPIREFLDQYDAPL |
| SEQ ID<br>NO: 10 | human<br>CISH | MVLCVQGPRPLLAVERTGQRPLWAPSLELPKPVMQPLPAGAFLEEV<br>AEGTPAQTESEPKVLDPEEDLLCIAKTFSYLRESGWYWGSITASEARQ<br>HLQKMPEGTFLVRDSTHPSYLFTLSVKTTRGPTNVRIEYADSSFRLDS<br>NCLSRPRILAFPDVVSLVQHYVASCTADTRSDSPDPAPTPALPMPKED<br>APSDPALPAPPPATAVHLKLVQPFVRRSSARSLQHLCRLVINRLVADV<br>DCLPLPRRMADYLRQYPFQL |

What is claimed is:

1. A method of treating a cancer patient, the method comprising:
   (a) determining a level of interleukin-7 receptor-α (IL-7Rα) protein expression in a sample from the cancer patient;
   (b) determining a level of a cytokine receptor-like factor 2 (CRLF2) protein expression in the sample from the cancer patient;
   (c) determining that the level of CRLF2 protein expression is greater than the level of IL-7Rα protein expression; and
   (d) administering a therapeutically effective amount of human thymic stromal lymphopoietin (TSLP) to the cancer patient, wherein the TSLP comprises the amino acid sequence set forth as SEQ ID NO: 1.

2. The method of claim 1, further comprising detecting a level of protein phosphorylation for STAT5 and/or a level of protein phosphorylation for ribosomal S6 in the sample from the cancer patient.

3. The method of claim 1, wherein the cancer is a leukemia.

4. The method of claim 1, wherein the CRLF2 and IL-7Rα protein expression is determined by flow cytometry.

* * * * *

SEQUENCE LISTING

<160> NUMBER OF SEQ ID NOS: 10

<210> SEQ ID NO 1
<211> LENGTH: 159
<212> TYPE: PRT
<213> ORGANISM: Homo sapiens

<400> SEQUENCE: 1

```
Met Phe Pro Phe Ala Leu Leu Tyr Val Leu Ser Val Ser Phe Arg Lys
1               5                   10                  15

Ile Phe Ile Leu Gln Leu Val Gly Leu Val Leu Thr Tyr Asp Phe Thr
            20                  25                  30

Asn Cys Asp Phe Glu Lys Ile Lys Ala Ala Tyr Leu Ser Thr Ile Ser
        35                  40                  45

Lys Asp Leu Ile Thr Tyr Met Ser Gly Thr Lys Ser Thr Glu Phe Asn
50                  55                  60

Asn Thr Val Ser Cys Ser Asn Arg Pro His Cys Leu Thr Glu Ile Gln
65                  70                  75                  80

Ser Leu Thr Phe Asn Pro Thr Ala Gly Cys Ala Ser Leu Ala Lys Glu
                85                  90                  95

Met Phe Ala Met Lys Thr Lys Ala Ala Leu Ala Ile Trp Cys Pro Gly
            100                 105                 110

Tyr Ser Glu Thr Gln Ile Asn Ala Thr Gln Ala Met Lys Lys Arg Arg
        115                 120                 125

Lys Arg Lys Val Thr Thr Asn Lys Cys Leu Glu Gln Val Ser Gln Leu
130                 135                 140

Gln Gly Leu Trp Arg Arg Phe Asn Arg Pro Leu Leu Lys Gln Gln
145                 150                 155

<210> SEQ ID NO 2
<211> LENGTH: 1207
<212> TYPE: PRT
<213> ORGANISM: Homo sapiens

<400> SEQUENCE: 2

Met Leu Leu Thr Leu Ile Ile Leu Leu Pro Val Val Ser Lys Phe Ser
1               5                   10                  15

Phe Val Ser Leu Ser Ala Pro Gln His Trp Ser Cys Pro Glu Gly Thr
            20                  25                  30

Leu Ala Gly Asn Gly Asn Ser Thr Cys Val Gly Pro Ala Pro Phe Leu
        35                  40                  45

Ile Phe Ser His Gly Asn Ser Ile Phe Arg Ile Asp Thr Glu Gly Thr
50                  55                  60

Asn Tyr Glu Gln Leu Val Val Asp Ala Gly Val Ser Val Ile Met Asp
65                  70                  75                  80

Phe His Tyr Asn Glu Lys Arg Ile Tyr Trp Val Asp Leu Glu Arg Gln
                85                  90                  95

Leu Leu Gln Arg Val Phe Leu Asn Gly Ser Arg Gln Glu Arg Val Cys
            100                 105                 110

Asn Ile Glu Lys Asn Val Ser Gly Met Ala Ile Asn Trp Ile Asn Glu
        115                 120                 125

Glu Val Ile Trp Ser Asn Gln Gln Glu Gly Ile Ile Thr Val Thr Asp
130                 135                 140

Met Lys Gly Asn Asn Ser His Ile Leu Leu Ser Ala Leu Lys Tyr Pro
145                 150                 155                 160

Ala Asn Val Ala Val Asp Pro Val Glu Arg Phe Ile Phe Trp Ser Ser
                165                 170                 175

Glu Val Ala Gly Ser Leu Tyr Arg Ala Asp Leu Asp Gly Val Gly Val
            180                 185                 190

Lys Ala Leu Leu Glu Thr Ser Glu Lys Ile Thr Ala Val Ser Leu Asp
        195                 200                 205

Val Leu Asp Lys Arg Leu Phe Trp Ile Gln Tyr Asn Arg Glu Gly Ser
210                 215                 220
```

```
Asn Ser Leu Ile Cys Ser Cys Asp Tyr Asp Gly Gly Ser Val His Ile
225                 230                 235                 240

Ser Lys His Pro Thr Gln His Asn Leu Phe Ala Met Ser Leu Phe Gly
            245                 250                 255

Asp Arg Ile Phe Tyr Ser Thr Trp Lys Met Lys Thr Ile Trp Ile Ala
        260                 265                 270

Asn Lys His Thr Gly Lys Asp Met Val Arg Ile Asn Leu His Ser Ser
    275                 280                 285

Phe Val Pro Leu Gly Glu Leu Lys Val Val His Pro Leu Ala Gln Pro
290                 295                 300

Lys Ala Glu Asp Asp Thr Trp Glu Pro Glu Gln Lys Leu Cys Lys Leu
305                 310                 315                 320

Arg Lys Gly Asn Cys Ser Ser Thr Val Cys Gly Gln Asp Leu Gln Ser
                325                 330                 335

His Leu Cys Met Cys Ala Glu Gly Tyr Ala Leu Ser Arg Asp Arg Lys
            340                 345                 350

Tyr Cys Glu Asp Val Asn Glu Cys Ala Phe Trp Asn His Gly Cys Thr
        355                 360                 365

Leu Gly Cys Lys Asn Thr Pro Gly Ser Tyr Tyr Cys Thr Cys Pro Val
    370                 375                 380

Gly Phe Val Leu Leu Pro Asp Gly Lys Arg Cys His Gln Leu Val Ser
385                 390                 395                 400

Cys Pro Arg Asn Val Ser Glu Cys Ser His Asp Cys Val Leu Thr Ser
                405                 410                 415

Glu Gly Pro Leu Cys Phe Cys Pro Glu Gly Ser Val Leu Glu Arg Asp
            420                 425                 430

Gly Lys Thr Cys Ser Gly Cys Ser Ser Pro Asp Asn Gly Gly Cys Ser
        435                 440                 445

Gln Leu Cys Val Pro Leu Ser Pro Val Ser Trp Glu Cys Asp Cys Phe
    450                 455                 460

Pro Gly Tyr Asp Leu Gln Leu Asp Glu Lys Ser Cys Ala Ala Ser Gly
465                 470                 475                 480

Pro Gln Pro Phe Leu Leu Phe Ala Asn Ser Gln Asp Ile Arg His Met
                485                 490                 495

His Phe Asp Gly Thr Asp Tyr Gly Thr Leu Leu Ser Gln Gln Met Gly
            500                 505                 510

Met Val Tyr Ala Leu Asp His Asp Pro Val Glu Asn Lys Ile Tyr Phe
        515                 520                 525

Ala His Thr Ala Leu Lys Trp Ile Glu Arg Ala Asn Met Asp Gly Ser
    530                 535                 540

Gln Arg Glu Arg Leu Ile Glu Glu Gly Val Asp Val Pro Glu Gly Leu
545                 550                 555                 560

Ala Val Asp Trp Ile Gly Arg Arg Phe Tyr Trp Thr Asp Arg Gly Lys
                565                 570                 575

Ser Leu Ile Gly Arg Ser Asp Leu Asn Gly Lys Arg Ser Lys Ile Ile
            580                 585                 590

Thr Lys Glu Asn Ile Ser Gln Pro Arg Gly Ile Ala Val His Pro Met
        595                 600                 605

Ala Lys Arg Leu Phe Trp Thr Asp Thr Gly Ile Asn Pro Arg Ile Glu
    610                 615                 620

Ser Ser Ser Leu Gln Gly Leu Gly Arg Leu Val Ile Ala Ser Ser Asp
625                 630                 635                 640
```

```
Leu Ile Trp Pro Ser Gly Ile Thr Ile Asp Phe Leu Thr Asp Lys Leu
              645                 650                 655

Tyr Trp Cys Asp Ala Lys Gln Ser Val Ile Glu Met Ala Asn Leu Asp
        660                 665                 670

Gly Ser Lys Arg Arg Leu Thr Gln Asn Asp Val Gly His Pro Phe
            675                 680                 685

Ala Val Ala Val Phe Glu Asp Tyr Val Trp Phe Ser Asp Trp Ala Met
    690                 695                 700

Pro Ser Val Met Arg Val Asn Lys Arg Thr Gly Lys Asp Arg Val Arg
705                 710                 715                 720

Leu Gln Gly Ser Met Leu Lys Pro Ser Ser Leu Val Val His Pro
                725                 730                 735

Leu Ala Lys Pro Gly Ala Asp Pro Cys Leu Tyr Gln Asn Gly Gly Cys
            740                 745                 750

Glu His Ile Cys Lys Lys Arg Leu Gly Thr Ala Trp Cys Ser Cys Arg
        755                 760                 765

Glu Gly Phe Met Lys Ala Ser Asp Gly Lys Thr Cys Leu Ala Leu Asp
    770                 775                 780

Gly His Gln Leu Leu Ala Gly Gly Val Asp Leu Lys Asn Gln Val
785                 790                 795                 800

Thr Pro Leu Asp Ile Leu Ser Lys Thr Arg Val Ser Glu Asp Asn Ile
            805                 810                 815

Thr Glu Ser Gln His Met Leu Val Ala Glu Ile Met Val Ser Asp Gln
        820                 825                 830

Asp Asp Cys Ala Pro Val Gly Cys Ser Met Tyr Ala Arg Cys Ile Ser
            835                 840                 845

Glu Gly Glu Asp Ala Thr Cys Gln Cys Leu Lys Gly Phe Ala Gly Asp
    850                 855                 860

Gly Lys Leu Cys Ser Asp Ile Asp Glu Cys Glu Met Gly Val Pro Val
865                 870                 875                 880

Cys Pro Pro Ala Ser Ser Lys Cys Ile Asn Thr Glu Gly Gly Tyr Val
            885                 890                 895

Cys Arg Cys Ser Glu Gly Tyr Gln Gly Asp Gly Ile His Cys Leu Asp
        900                 905                 910

Ile Asp Glu Cys Gln Leu Gly Glu His Ser Cys Gly Glu Asn Ala Ser
    915                 920                 925

Cys Thr Asn Thr Glu Gly Gly Tyr Thr Cys Met Cys Ala Gly Arg Leu
        930                 935                 940

Ser Glu Pro Gly Leu Ile Cys Pro Asp Ser Thr Pro Pro His Leu
945                 950                 955                 960

Arg Glu Asp Asp His His Tyr Ser Val Arg Asn Ser Asp Ser Glu Cys
            965                 970                 975

Pro Leu Ser His Asp Gly Tyr Cys Leu His Asp Gly Val Cys Met Tyr
        980                 985                 990

Ile Glu Ala Leu Asp Lys Tyr Ala Cys Asn Cys Val Val Gly Tyr Ile
        995                1000                1005

Gly Glu Arg Cys Gln Tyr Arg Asp Leu Lys Trp Trp Glu Leu Arg
       1010                1015                1020

His Ala Gly His Gly Gln Gln Gln Lys Val Ile Val Val Ala Val
       1025                1030                1035

Cys Val Val Val Leu Val Met Leu Leu Leu Leu Ser Leu Trp Gly
       1040                1045                1050

Ala His Tyr Tyr Arg Thr Gln Lys Leu Leu Ser Lys Asn Pro Lys
```

```
                1055                1060                1065

Asn Pro Tyr Glu Glu Ser Ser Arg Asp Val Arg Ser Arg Arg Pro
        1070                1075                1080

Ala Asp Thr Glu Asp Gly Met Ser Ser Cys Pro Gln Pro Trp Phe
        1085                1090                1095

Val Val Ile Lys Glu His Gln Asp Leu Lys Asn Gly Gly Gln Pro
        1100                1105                1110

Val Ala Gly Glu Asp Gly Gln Ala Ala Asp Gly Ser Met Gln Pro
        1115                1120                1125

Thr Ser Trp Arg Gln Glu Pro Gln Leu Cys Gly Met Gly Thr Glu
        1130                1135                1140

Gln Gly Cys Trp Ile Pro Val Ser Ser Asp Lys Gly Ser Cys Pro
        1145                1150                1155

Gln Val Met Glu Arg Ser Phe His Met Pro Ser Tyr Gly Thr Gln
        1160                1165                1170

Thr Leu Glu Gly Gly Val Glu Lys Pro His Ser Leu Leu Ser Ala
        1175                1180                1185

Asn Pro Leu Trp Gln Gln Arg Ala Leu Asp Pro His Gln Met
        1190                1195                1200

Glu Leu Thr Gln
        1205

<210> SEQ ID NO 3
<211> LENGTH: 177
<212> TYPE: PRT
<213> ORGANISM: Homo sapiens

<400> SEQUENCE: 3

Met Phe His Val Ser Phe Arg Tyr Ile Phe Gly Leu Pro Pro Leu Ile
1               5                   10                  15

Leu Val Leu Leu Pro Val Ala Ser Ser Asp Cys Asp Ile Glu Gly Lys
                20                  25                  30

Asp Gly Lys Gln Tyr Glu Ser Val Leu Met Val Ser Ile Asp Gln Leu
            35                  40                  45

Leu Asp Ser Met Lys Glu Ile Gly Ser Asn Cys Leu Asn Asn Glu Phe
        50                  55                  60

Asn Phe Phe Lys Arg His Ile Cys Asp Ala Asn Lys Glu Gly Met Phe
65                  70                  75                  80

Leu Phe Arg Ala Ala Arg Lys Leu Arg Gln Phe Leu Lys Met Asn Ser
                85                  90                  95

Thr Gly Asp Phe Asp Leu His Leu Leu Lys Val Ser Glu Gly Thr Thr
            100                 105                 110

Ile Leu Leu Asn Cys Thr Gly Gln Val Lys Gly Arg Lys Pro Ala Ala
        115                 120                 125

Leu Gly Glu Ala Gln Pro Thr Lys Ser Leu Glu Glu Asn Lys Ser Leu
    130                 135                 140

Lys Glu Gln Lys Lys Leu Asn Asp Leu Cys Phe Leu Lys Arg Leu Leu
145                 150                 155                 160

Gln Glu Ile Lys Thr Cys Trp Asn Lys Ile Leu Met Gly Thr Lys Glu
                165                 170                 175

His

<210> SEQ ID NO 4
<211> LENGTH: 370
<212> TYPE: PRT
```

-continued

<213> ORGANISM: Homo sapiens

<400> SEQUENCE: 4

Met Gly Arg Leu Val Leu Leu Trp Gly Ala Val Phe Leu Leu Gly
1               5                   10                  15

Gly Trp Met Ala Leu Gly Gln Gly Ala Ala Glu Gly Val Gln Ile
            20                  25                  30

Gln Ile Ile Tyr Phe Asn Leu Glu Thr Val Gln Val Thr Trp Asn Ala
        35                  40                  45

Ser Lys Tyr Ser Arg Thr Asn Leu Thr Phe His Tyr Arg Phe Asn Gly
    50                  55                  60

Asp Glu Ala Tyr Asp Gln Cys Thr Asn Tyr Leu Leu Gln Glu Gly His
65                  70                  75                  80

Thr Ser Gly Cys Leu Leu Asp Ala Glu Gln Arg Asp Asp Ile Leu Tyr
                85                  90                  95

Phe Ser Ile Arg Asn Gly Thr His Pro Val Phe Thr Ala Ser Arg Trp
            100                 105                 110

Met Val Tyr Tyr Leu Lys Pro Ser Pro Lys His Val Arg Phe Ser
            115                 120                 125

Trp His Gln Asp Ala Val Thr Val Thr Cys Ser Asp Leu Ser Tyr Gly
    130                 135                 140

Asp Leu Leu Tyr Glu Val Gln Tyr Arg Ser Pro Phe Asp Thr Glu Trp
145                 150                 155                 160

Gln Ser Lys Gln Glu Asn Thr Cys Asn Val Thr Ile Glu Gly Leu Asp
                165                 170                 175

Ala Glu Lys Cys Tyr Ser Phe Trp Val Arg Val Lys Ala Met Glu Asp
            180                 185                 190

Val Tyr Gly Pro Asp Thr Tyr Pro Ser Asp Trp Ser Glu Val Thr Cys
            195                 200                 205

Trp Gln Arg Gly Glu Ile Arg Asp Ala Cys Ala Glu Thr Pro Thr Pro
    210                 215                 220

Pro Lys Pro Lys Leu Ser Lys Phe Ile Leu Ile Ser Ser Leu Ala Ile
225                 230                 235                 240

Leu Leu Met Val Ser Leu Leu Leu Ser Leu Trp Lys Leu Trp Arg
                245                 250                 255

Val Lys Lys Phe Leu Ile Pro Ser Val Pro Asp Pro Lys Ser Ile Phe
            260                 265                 270

Pro Gly Leu Phe Glu Ile His Gln Gly Asn Phe Gln Glu Trp Ile Asp
            275                 280                 285

Thr Gln Asn Val Ala His Leu His Lys Met Ala Gly Ala Glu Gln Glu
    290                 295                 300

Ser Gly Pro Glu Glu Pro Leu Val Val Gln Leu Ala Lys Thr Glu Ala
305                 310                 315                 320

Glu Ser Pro Arg Met Leu Asp Pro Gln Thr Glu Glu Lys Glu Ala Ser
                325                 330                 335

Gly Gly Ser Leu Gln Leu Pro His Gln Pro Leu Gln Gly Gly Asp Val
            340                 345                 350

Val Thr Ile Gly Gly Phe Thr Phe Val Met Asn Asp Arg Ser Tyr Val
            355                 360                 365

Ala Leu
370

<210> SEQ ID NO 5
<211> LENGTH: 459

<212> TYPE: PRT
<213> ORGANISM: Homo sapiens

<400> SEQUENCE: 5

```
Met Thr Ile Leu Gly Thr Thr Phe Gly Met Val Phe Ser Leu Leu Gln
1               5                   10                  15

Val Val Ser Gly Glu Ser Gly Tyr Ala Gln Asn Gly Asp Leu Glu Asp
            20                  25                  30

Ala Glu Leu Asp Asp Tyr Ser Phe Ser Cys Tyr Ser Gln Leu Glu Val
        35                  40                  45

Asn Gly Ser Gln His Ser Leu Thr Cys Ala Phe Glu Asp Pro Asp Val
    50                  55                  60

Asn Ile Thr Asn Leu Glu Phe Glu Ile Cys Gly Ala Leu Val Glu Val
65                  70                  75                  80

Lys Cys Leu Asn Phe Arg Lys Leu Gln Glu Ile Tyr Phe Ile Glu Thr
                85                  90                  95

Lys Lys Phe Leu Leu Ile Gly Lys Ser Asn Ile Cys Val Lys Val Gly
            100                 105                 110

Glu Lys Ser Leu Thr Cys Lys Lys Ile Asp Leu Thr Thr Ile Val Lys
        115                 120                 125

Pro Glu Ala Pro Phe Asp Leu Ser Val Val Tyr Arg Glu Gly Ala Asn
130                 135                 140

Asp Phe Val Val Thr Phe Asn Thr Ser His Leu Gln Lys Lys Tyr Val
145                 150                 155                 160

Lys Val Leu Met His Asp Val Ala Tyr Arg Gln Glu Lys Asp Glu Asn
                165                 170                 175

Lys Trp Thr His Val Asn Leu Ser Ser Thr Lys Leu Thr Leu Leu Gln
            180                 185                 190

Arg Lys Leu Gln Pro Ala Ala Met Tyr Glu Ile Lys Val Arg Ser Ile
        195                 200                 205

Pro Asp His Tyr Phe Lys Gly Phe Trp Ser Glu Trp Ser Pro Ser Tyr
210                 215                 220

Tyr Phe Arg Thr Pro Glu Ile Asn Asn Ser Ser Gly Glu Met Asp Pro
225                 230                 235                 240

Ile Leu Leu Thr Ile Ser Ile Leu Ser Phe Phe Ser Val Ala Leu Leu
                245                 250                 255

Val Ile Leu Ala Cys Val Leu Trp Lys Lys Arg Ile Lys Pro Ile Val
            260                 265                 270

Trp Pro Ser Leu Pro Asp His Lys Lys Thr Leu Glu His Leu Cys Lys
        275                 280                 285

Lys Pro Arg Lys Asn Leu Asn Val Ser Phe Asn Pro Glu Ser Phe Leu
290                 295                 300

Asp Cys Gln Ile His Arg Val Asp Asp Ile Gln Ala Arg Asp Glu Val
305                 310                 315                 320

Glu Gly Phe Leu Gln Asp Thr Phe Pro Gln Gln Leu Glu Glu Ser Glu
                325                 330                 335

Lys Gln Arg Leu Gly Gly Asp Val Gln Ser Pro Asn Cys Pro Ser Glu
            340                 345                 350

Asp Val Val Ile Thr Pro Glu Ser Phe Gly Arg Asp Ser Ser Leu Thr
        355                 360                 365

Cys Leu Ala Gly Asn Val Ser Ala Cys Asp Ala Pro Ile Leu Ser Ser
370                 375                 380

Ser Arg Ser Leu Asp Cys Arg Glu Ser Gly Lys Asn Gly Pro His Val
385                 390                 395                 400
```

Tyr Gln Asp Leu Leu Leu Ser Leu Gly Thr Thr Asn Ser Thr Leu Pro
                405                 410                 415

Pro Pro Phe Ser Leu Gln Ser Gly Ile Leu Thr Leu Asn Pro Val Ala
            420                 425                 430

Gln Gly Gln Pro Ile Leu Thr Ser Leu Gly Ser Asn Gln Glu Glu Ala
        435                 440                 445

Tyr Val Thr Met Ser Ser Phe Tyr Gln Asn Gln
    450                 455

<210> SEQ ID NO 6
<211> LENGTH: 1210
<212> TYPE: PRT
<213> ORGANISM: Homo sapiens

<400> SEQUENCE: 6

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu

```
                305                 310                 315                 320
Asp Gly Val Arg Lys Cys Lys Cys Glu Gly Pro Cys Arg Lys Val
                325                 330                 335
Cys Asn Gly Ile Gly Ile Gly Glu Phe Lys Asp Ser Leu Ser Ile Asn
                340                 345                 350
Ala Thr Asn Ile Lys His Phe Lys Asn Cys Thr Ser Ile Ser Gly Asp
                355                 360                 365
Leu His Ile Leu Pro Val Ala Phe Arg Gly Asp Ser Phe Thr His Thr
                370                 375                 380
Pro Pro Leu Asp Pro Gln Glu Leu Asp Ile Leu Lys Thr Val Lys Glu
385                 390                 395                 400
Ile Thr Gly Phe Leu Leu Ile Gln Ala Trp Pro Glu Asn Arg Thr Asp
                405                 410                 415
Leu His Ala Phe Glu Asn Leu Glu Ile Ile Arg Gly Arg Thr Lys Gln
                420                 425                 430
His Gly Gln Phe Ser Leu Ala Val Val Ser Leu Asn Ile Thr Ser Leu
                435                 440                 445
Gly Leu Arg Ser Leu Lys Glu Ile Ser Asp Gly Asp Val Ile Ile Ser
                450                 455                 460
Gly Asn Lys Asn Leu Cys Tyr Ala Asn Thr Ile Asn Trp Lys Lys Leu
465                 470                 475                 480
Phe Gly Thr Ser Gly Gln Lys Thr Lys Ile Ile Ser Asn Arg Gly Glu
                485                 490                 495
Asn Ser Cys Lys Ala Thr Gly Gln Val Cys His Ala Leu Cys Ser Pro
                500                 505                 510
Glu Gly Cys Trp Gly Pro Glu Pro Arg Asp Cys Val Ser Cys Arg Asn
                515                 520                 525
Val Ser Arg Gly Arg Glu Cys Val Asp Lys Cys Asn Leu Leu Glu Gly
                530                 535                 540
Glu Pro Arg Glu Phe Val Glu Asn Ser Glu Cys Ile Gln Cys His Pro
545                 550                 555                 560
Glu Cys Leu Pro Gln Ala Met Asn Ile Thr Cys Thr Gly Arg Gly Pro
                565                 570                 575
Asp Asn Cys Ile Gln Cys Ala His Tyr Ile Asp Gly Pro His Cys Val
                580                 585                 590
Lys Thr Cys Pro Ala Gly Val Met Gly Glu Asn Asn Thr Leu Val Trp
                595                 600                 605
Lys Tyr Ala Asp Ala Gly His Val Cys His Leu Cys His Pro Asn Cys
                610                 615                 620
Thr Tyr Gly Cys Thr Gly Pro Gly Leu Glu Gly Cys Pro Thr Asn Gly
625                 630                 635                 640
Pro Lys Ile Pro Ser Ile Ala Thr Gly Met Val Gly Ala Leu Leu Leu
                645                 650                 655
Leu Leu Val Val Ala Leu Gly Ile Gly Leu Phe Met Arg Arg Arg His
                660                 665                 670
Ile Val Arg Lys Arg Thr Leu Arg Arg Leu Leu Gln Glu Arg Glu Leu
                675                 680                 685
Val Glu Pro Leu Thr Pro Ser Gly Glu Ala Pro Asn Gln Ala Leu Leu
                690                 695                 700
Arg Ile Leu Lys Glu Thr Glu Phe Lys Lys Ile Lys Val Leu Gly Ser
705                 710                 715                 720
Gly Ala Phe Gly Thr Val Tyr Lys Gly Leu Trp Ile Pro Glu Gly Glu
                725                 730                 735
```

```
Lys Val Lys Ile Pro Val Ala Ile Lys Glu Leu Arg Glu Ala Thr Ser
                740                 745                 750

Pro Lys Ala Asn Lys Glu Ile Leu Asp Glu Ala Tyr Val Met Ala Ser
                755                 760                 765

Val Asp Asn Pro His Val Cys Arg Leu Leu Gly Ile Cys Leu Thr Ser
                770                 775             780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
                820                 825                 830

Leu Val His Arg Asp Leu Ala Ala Arg Asn Val Leu Val Lys Thr Pro
                835                 840                 845

Gln His Val Lys Ile Thr Asp Phe Gly Leu Ala Lys Leu Leu Gly Ala
                850                 855             860

Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
                900                 905             910

Lys Pro Tyr Asp Gly Ile Pro Ala Ser Glu Ile Ser Ser Ile Leu Glu
                915                 920                 925

Lys Gly Glu Arg Leu Pro Gln Pro Pro Ile Cys Thr Ile Asp Val Tyr
                930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
                980                 985             990

Thr Asp Ser Asn Phe Tyr Arg Ala  Leu Met Asp Glu Glu  Asp Met Asp
                995                 1000                1005

Asp Val  Val Asp Ala Asp Glu  Tyr Leu Ile Pro Gln  Gln Gly Phe
    1010                1015                1020

Phe Ser  Ser Pro Ser Thr Ser  Arg Thr Pro Leu Leu  Ser Ser Leu
    1025                1030                1035

Ser Ala  Thr Ser Asn Asn Ser  Thr Val Ala Cys Ile  Asp Arg Asn
    1040                1045                1050

Gly Leu  Gln Ser Cys Pro Ile  Lys Glu Asp Ser Phe  Leu Gln Arg
    1055                1060                1065

Tyr Ser  Ser Asp Pro Thr Gly  Ala Leu Thr Glu Asp  Ser Ile Asp
    1070                1075                1080

Asp Thr  Phe Leu Pro Val Pro  Glu Tyr Ile Asn Gln  Ser Val Pro
    1085                1090                1095

Lys Arg  Pro Ala Gly Ser Val  Gln Asn Pro Val Tyr  His Asn Gln
    1100                1105                1110

Pro Leu  Asn Pro Ala Pro Ser  Arg Asp Pro His Tyr  Gln Asp Pro
    1115                1120                1125

His Ser  Thr Ala Val Gly Asn  Pro Glu Tyr Leu Asn  Thr Val Gln
    1130                1135                1140
```

```
Pro Thr Cys Val Asn Ser Thr Phe Asp Ser Pro Ala His Trp Ala
    1145                1150                1155

Gln Lys Gly Ser His Gln Ile Ser Leu Asp Asn Pro Asp Tyr Gln
    1160                1165                1170

Gln Asp Phe Phe Pro Lys Glu Ala Lys Pro Asn Gly Ile Phe Lys
    1175                1180                1185

Gly Ser Thr Ala Glu Asn Ala Glu Tyr Leu Arg Val Ala Pro Gln
    1190                1195                1200

Ser Ser Glu Phe Ile Gly Ala
    1205                1210

<210> SEQ ID NO 7
<211> LENGTH: 211
<212> TYPE: PRT
<213> ORGANISM: Homo sapiens

<400> SEQUENCE: 7

Met Val Ala His Asn Gln Val Ala Ala Asp Asn Ala Val Ser Thr Ala
1               5                   10                  15

Ala Glu Pro Arg Arg Pro Glu Pro Ser Ser Ser Ser Ser Ser
                20                  25                  30

Pro Ala Ala Pro Ala Arg Pro Arg Pro Cys Pro Ala Val Pro Ala Pro
            35                  40                  45

Ala Pro Gly Asp Thr His Phe Arg Thr Phe Arg Ser His Ala Asp Tyr
    50                  55                  60

Arg Arg Ile Thr Arg Ala Ser Ala Leu Leu Asp Ala Cys Gly Phe Tyr
65                  70                  75                  80

Trp Gly Pro Leu Ser Val His Gly Ala His Glu Arg Leu Arg Ala Glu
                85                  90                  95

Pro Val Gly Thr Phe Leu Val Arg Asp Ser Arg Gln Arg Asn Cys Phe
            100                 105                 110

Phe Ala Leu Ser Val Lys Met Ala Ser Gly Pro Thr Ser Ile Arg Val
        115                 120                 125

His Phe Gln Ala Gly Arg Phe His Leu Asp Gly Ser Arg Glu Ser Phe
    130                 135                 140

Asp Cys Leu Phe Glu Leu Leu Glu His Tyr Val Ala Ala Pro Arg Arg
145                 150                 155                 160

Met Leu Gly Ala Pro Leu Arg Gln Arg Arg Val Arg Pro Leu Gln Glu
                165                 170                 175

Leu Cys Arg Gln Arg Ile Val Ala Thr Val Gly Arg Glu Asn Leu Ala
            180                 185                 190

Arg Ile Pro Leu Asn Pro Val Leu Arg Asp Tyr Leu Ser Ser Phe Pro
        195                 200                 205

Phe Gln Ile
    210

<210> SEQ ID NO 8
<211> LENGTH: 198
<212> TYPE: PRT
<213> ORGANISM: Homo sapiens

<400> SEQUENCE: 8

Met Thr Leu Arg Cys Leu Glu Pro Ser Gly Asn Gly Gly Glu Gly Thr
1               5                   10                  15

Arg Ser Gln Trp Gly Thr Ala Ser Ala Glu Glu Pro Ser Pro Gln
                20                  25                  30
```

```
Ala Ala Arg Leu Ala Lys Ala Leu Arg Glu Leu Gly Gln Thr Gly Trp
         35                  40                  45

Tyr Trp Gly Ser Met Thr Val Asn Glu Ala Lys Glu Lys Leu Lys Glu
 50                  55                  60

Ala Pro Glu Gly Thr Phe Leu Ile Arg Asp Ser Ser His Ser Asp Tyr
 65                  70                  75                  80

Leu Leu Thr Ile Ser Val Lys Thr Ser Ala Gly Pro Thr Asn Leu Arg
                 85                  90                  95

Ile Glu Tyr Gln Asp Gly Lys Phe Arg Leu Asp Ser Ile Ile Cys Val
                100                 105                 110

Lys Ser Lys Leu Lys Gln Phe Asp Ser Val Val His Leu Ile Asp Tyr
             115                 120                 125

Tyr Val Gln Met Cys Lys Asp Lys Arg Thr Gly Pro Glu Ala Pro Arg
         130                 135                 140

Asn Gly Thr Val His Leu Tyr Leu Thr Lys Pro Leu Tyr Thr Ser Ala
145                 150                 155                 160

Pro Ser Leu Gln His Leu Cys Arg Leu Thr Ile Asn Lys Cys Thr Gly
                165                 170                 175

Ala Ile Trp Gly Leu Pro Leu Pro Thr Arg Leu Lys Asp Tyr Leu Glu
            180                 185                 190

Glu Tyr Lys Phe Gln Val
            195

<210> SEQ ID NO 9
<211> LENGTH: 225
<212> TYPE: PRT
<213> ORGANISM: Homo sapiens

<400> SEQUENCE: 9

Met Val Thr His Ser Lys Phe Pro Ala Ala Gly Met Ser Arg Pro Leu
 1               5                  10                  15

Asp Thr Ser Leu Arg Leu Lys Thr Phe Ser Ser Lys Ser Glu Tyr Gln
             20                  25                  30

Leu Val Val Asn Ala Val Arg Lys Leu Gln Glu Ser Gly Phe Tyr Trp
         35                  40                  45

Ser Ala Val Thr Gly Gly Glu Ala Asn Leu Leu Leu Ser Ala Glu Pro
 50                  55                  60

Ala Gly Thr Phe Leu Ile Arg Asp Ser Ser Asp Gln Arg His Phe Phe
 65                  70                  75                  80

Thr Leu Ser Val Lys Thr Gln Ser Gly Thr Lys Asn Leu Arg Ile Gln
                 85                  90                  95

Cys Glu Gly Gly Ser Phe Ser Leu Gln Ser Asp Pro Arg Ser Thr Gln
                100                 105                 110

Pro Val Pro Arg Phe Asp Cys Val Leu Lys Leu Val His His Tyr Met
             115                 120                 125

Pro Pro Pro Gly Ala Pro Ser Phe Pro Ser Pro Thr Glu Pro Ser
         130                 135                 140

Ser Glu Val Pro Glu Gln Pro Ser Ala Gln Pro Leu Pro Gly Ser Pro
145                 150                 155                 160

Pro Arg Arg Ala Tyr Tyr Ile Tyr Ser Gly Gly Glu Lys Ile Pro Leu
                165                 170                 175

Val Leu Ser Arg Pro Leu Ser Ser Asn Val Ala Thr Leu Gln His Leu
            180                 185                 190

Cys Arg Lys Thr Val Asn Gly His Leu Asp Ser Tyr Glu Lys Val Thr
        195                 200                 205
```

Gln Leu Pro Gly Pro Ile Arg Glu Phe Leu Asp Gln Tyr Asp Ala Pro
            210                 215                 220

Leu
225

<210> SEQ ID NO 10
<211> LENGTH: 258
<212> TYPE: PRT
<213> ORGANISM: Homo sapiens

<400> SEQUENCE: 10

Met Val Leu Cys Val Gln Gly Pro Arg Pro Leu Leu Ala Val Glu Arg
1               5                   10                  15

Thr Gly Gln Arg Pro Leu Trp Ala Pro Ser Leu Glu Leu Pro Lys Pro
            20                  25                  30

Val Met Gln Pro Leu Pro Ala Gly Ala Phe Leu Glu Val Ala Glu
        35                  40                  45

Gly Thr Pro Ala Gln Thr Glu Ser Glu Pro Lys Val Leu Asp Pro Glu
    50                  55                  60

Glu Asp Leu Leu Cys Ile Ala Lys Thr Phe Ser Tyr Leu Arg Glu Ser
65                  70                  75                  80

Gly Trp Tyr Trp Gly Ser Ile Thr Ala Ser Glu Ala Arg Gln His Leu
                85                  90                  95

Gln Lys Met Pro Glu Gly Thr Phe Leu Val Arg Asp Ser Thr His Pro
            100                 105                 110

Ser Tyr Leu Phe Thr Leu Ser Val Lys Thr Thr Arg Gly Pro Thr Asn
        115                 120                 125

Val Arg Ile Glu Tyr Ala Asp Ser Ser Phe Arg Leu Asp Ser Asn Cys
    130                 135                 140

Leu Ser Arg Pro Arg Ile Leu Ala Phe Pro Asp Val Val Ser Leu Val
145                 150                 155                 160

Gln His Tyr Val Ala Ser Cys Thr Ala Asp Thr Arg Ser Asp Ser Pro
                165                 170                 175

Asp Pro Ala Pro Thr Pro Ala Leu Pro Met Pro Lys Glu Asp Ala Pro
            180                 185                 190

Ser Asp Pro Ala Leu Pro Ala Pro Pro Ala Thr Ala Val His Leu
        195                 200                 205

Lys Leu Val Gln Pro Phe Val Arg Arg Ser Ser Ala Arg Ser Leu Gln
    210                 215                 220

His Leu Cys Arg Leu Val Ile Asn Arg Leu Val Ala Asp Val Asp Cys
225                 230                 235                 240

Leu Pro Leu Pro Arg Arg Met Ala Asp Tyr Leu Arg Gln Tyr Pro Phe
                245                 250                 255

Gln Leu